United States Patent [19]

Krantz et al.

[11] Patent Number: 4,657,893
[45] Date of Patent: Apr. 14, 1987

[54] 4H-3,1-BENZOXAZIN-4-ONES AND RELATED COMPOUNDS AND USE AS ENZYME INHIBITORS

[75] Inventors: Alexander Krantz, Toronto; Robin Spencer; Tim Tam, both of Mississauga, all of Canada

[73] Assignee: Syntex (U.S.A.) Inc., Palo Alto, Calif.

[21] Appl. No.: 673,996

[22] Filed: Nov. 26, 1984

Related U.S. Application Data

[63] Continuation-in-part of Ser. No. 608,609, May 9, 1984, abandoned, which is a continuation-in-part of Ser. No. 566,129, Dec. 27, 1983, abandoned.

[51] Int. Cl.$^4$ .................. A61K 37/02; A61K 31/535; C07D 265/06
[52] U.S. Cl. .......................... 514/18; 514/19; 514/232; 514/233; 514/234; 514/235; 514/236; 514/237; 530/331; 544/92
[58] Field of Search ............... 544/92; 260/112.5 R; 424/177, 248.52, 248.54, 248.56; 514/232, 234, 235, 233, 236, 237, 18, 19; 530/331

[56] References Cited

U.S. PATENT DOCUMENTS

| Re. 32,087 | 2/1986 | Hamprecht et al. | 71/88 |
| 3,450,700 | 6/1969 | Sayigh et al. | 544/92 X |
| 3,470,168 | 9/1969 | Wolf et al. | 260/243 |
| 4,315,766 | 2/1982 | Hamprecht et al. | 71/88 |

FOREIGN PATENT DOCUMENTS

| 2043665 | 9/1970 | Fed. Rep. of Germany. |
| 2218302 | 10/1973 | Fed. Rep. of Germany. |
| 2315303 | 10/1974 | Fed. Rep. of Germany. |
| 2121341 | 8/1972 | France. |
| 54-66687 | 5/1979 | Japan. |
| 55-76868 | 6/1980 | Japan. |

OTHER PUBLICATIONS

Perronnet et al, J. Heterocyclic Chemistry, vol. 17 (1980) pp. 673–678.
Hedstrom et al, Chemical Abstracts, vol. 100 (1984) 134,877h.
Sheehan et al, J. Org. Chem., vol. 29 (1964) pp. 3599–3601.
Papadopoulos et al, J. Het. Chem., vol. 19, No. 2 (1982) pp. 269–272.
Petridou-Fischer et al, J. Het. Chem., vol. 19, No. 1 (1982) pp. 123–126.
Perronnet et al, Chemical Abstracts, vol. 93 (1980) 203,550x.
J. Heterocycl. Chem., 1980, 17(7) 1553–8 (Eng.) Papadopoulos (Chem. Abstr., vol. 95, (1981) 156894K).
J. Org. Chem., 32(12), 4052–53 (1967)(Eng.) (Chem. Abstr., vol. 68, (1968) 21894p).
Tetrahedron Letters, 1965(30) 2597–606 (Eng.) (Chem. Abstr., vol. 63, (1965) 9773).
Bull. Chem. Soc. Jap., 39(9), 1942–8 (1966) (Eng.) (Chem. Abstr., vol. 663, (1967) 37877e).
Chem. Ber., 1976, 109(1), 200–11 (Ger.) (Chem. Abstr., vol. 84, (1976) 90111y).
Bul. Stiint, Teh. Inst. Politeh, 1982, 27(1), 131–6 (Rom.) (Chem. Abstr., vol. 99, (1983) 53707m).
J. Chem. Soc., Perkin Trans. 1, 1983, (4), 813–16 (Eng.) (Chem. Abstr., vol. 99, (1983) 88161f).
Synthesis 1983, (5), 406–8 (Eng.) (Chem. Abstr., vol. 99, (1983) 88143b).
Chem. Ber., 1982, 115(2), 475–82 (Ger.) (Chem. Abstr., vol. 96 (1982) 142613h).
J. Amer. Chem. Soc., 1970, 92(22) 6561–7, Bruice et al. (Chem. Abstr., vol. 74, (1971) 12333b).
Can. J. Chem., 1977, 55, 630–9 (Eng.) Ahern et al. (Chem. Abstr., vol. 88, (1978) 22841u).
J. Org. Chem., 1974, 39(13), 1931–5 (Eng.) Peet et al. (Chem. Abstr., vol. 81, (1974) 49386s).
Arch. Pharm., 1971, 304(10), 763–73, Neidlein et al. (Chem. Abstr., vol. 76, (1972) 126816h).
J. Heterocycl. Chem., 1981, 18(3), 515–18 (Eng.), Papadopoulos (Chem. Abstr., vol. 95, (1981) 97718n).
J. Org. Chem., 1977, 42(1), 12–18 (Eng.), Errede et al. (Chem. Abstr., vol. 86, (1977) 55375g).
Biochemistry 1984, 23, 1753–1759, Hedstrom et al.

*Primary Examiner*—Richard L. Raymond
*Attorney, Agent, or Firm*—Liza K. Toth; Tom M. Moran

[57] ABSTRACT

Novel 2-amino-4H-3,1-benzoxazin-4-ones represented by the formula

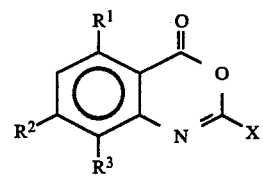

wherein $R^1$, $R^2$, $R^3$ and X are defined herein are useful as enzyme inhibitors in animals.

40 Claims, No Drawings

4H-3,1-BENZOXAZIN-4-ONES AND RELATED COMPOUNDS AND USE AS ENZYME INHIBITORS

This application is a continuation-in-part of copending U.S. application Ser. No. 608,609, filed May 9, 1984, now abandoned, which in turn is a continuation-in-part of U.S. application Ser. No. 566,129, filed Dec. 27, 1983, now abandoned.

BACKGROUND OF THE INVENTION

1. Field of the Invention

This invention relates to (i) novel 2-amino-4H-3,1-benzoxazin-4-ones and the pharmaceutically acceptable, non-toxic esters and salts thereof; (ii) the use of these compounds as enzyme inhibitors in animals; (iii) pharmaceutical compositions comprising a compound of this invention and at least one pharmaceutical excipient; and (iv) processes for preparing the compounds of this invention.

2. Related Art

The compounds of this invention are 2-amino-substituted derivatives of 4H-3,1-benzoxazinones having the following structure:

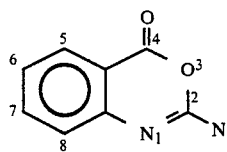

2-Amino-4H-3,1-benzoxazin-4-one, and the corresponding compounds in which both hydrogen atoms of the 2-amino group have been replaced by a substituent such as alkyl, have been described previously; see, for example, *Monatsch*, 95 (3) 950–960 and U.S. Pat. No. 3,450,700 assigned to The Upjohn Company. 2-Amino-4H-3,1-benzoxazin-4-ones in which only one hydrogen atom of the 2-amino group has been replaced with a phenyl substitutent are described by Sheehan et al., *J. Org. Chem.* 29, 3599–3601, 1964 and Herlinger, *Angew. Chem.* 76, 437, 1964. Corresponding compounds in which the 2-amino substituent is a mono- or di-methyl substituted morpholinyl group are disclosed in W. German Patent No. 29-14-915 to BASF. None of these compounds are reported to have activity as physiological enzyme inhibitors.

A few 4H-3,1-benzoxazin-4-ones are known to possess enzyme-inhibitory activity. Teshima et al. have disclosed various 2-alkyl-4H-3,1-benzoxazin-4-ones reported to be active as enzyme inhibitors (*J. Biol. Chem*, 257, 5085–5091, 1982), and 4H-3,1-benzoxazin-2,4-dione has been disclosed as having some enzyme inhibitory activity (Moorman, A. R., and Abeles, R. H. *J. Amer. Chem. Soc.* 104, 6785–6786, 1982).

SUMMARY

This invention relates to novel 2-amino-4H-3,1-benzoxzin-4-ones represented by the formula:

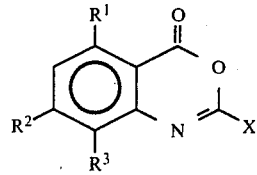

and the pharmaceutically acceptable esters and salts thereof, wherein:

$R^1$ is hydrogen or lower alkyl;

$R^2$ and $R^3$ are each independently hydrogen, halo, lower alkyl, hydroxy, lower alkoxy, lower thioalkyl, —NO$_2$, —N(R')$_2$, —NR'COR', —NHCON(R')$_2$ or —NHCOOR', with the proviso that at least one of $R^1$, $R^2$ and $R^3$ is not hydrogen when X is NHR or NR'COR''; and X is a radical chosen from the group consisting of:

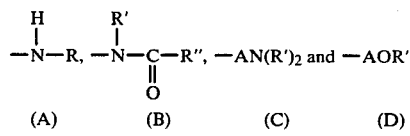

in which:

R is lower alkyl, lower alkenyl, lower alkynyl, optionally substituted lower cycloalkyl or optionally substituted phenyl lower alkyl;

each R' is independently hydrogen or lower alkyl, or lower alkenyl or lower alkynyl where the unsaturated bond is at least one carbon removed from the O or N atom;

each R'' is independently R, lower alkoxy, NHR' or AOR'; and

A is an amino acid residue, or a peptide of 2 to 3 amino acid residues.

In a second aspect, this invention relates to a pharmaceutical composition comprising a compound of Formula I and at least one pharmaceutically acceptable excipient.

A third aspect of the invention concerns methods of using compounds of Formula I, or pharmaceutical compositions thereof, as inhibitors of enzymes in animals.

A fourth aspect of the invention concerns processes for the preparation of compounds of Formula I, and the pharmaceutically acceptable non-toxic esters and salts thereof which comprise:

1. A process for the preparation of compounds of the formula:

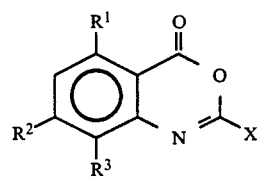

and the pharmaceutically acceptable esters and salts thereof, wherein, $R^1$ is hydrogen or lower alkyl;

$R^2$ and $R^3$ are each independently hydrogen, halo, lower alkyl, hydroxy, lower alkoxy, lower thioalkyl, —NO$_2$, —N(R')$_2$, —NR'COR', —NHCON(R')$_2$ or —NHCOOR', with the proviso that at least one of $R^1$, $R^2$ and $R^3$ is not hydrogen when X is NHR or NR'COR''; and X is a radical chosen from the group consisting of:

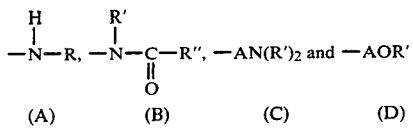

in which:

R is lower alkyl, lower alkenyl, lower alkynyl, optionally substituted lower cycloalkyl or optionally substituted phenyl lower alkyl;

each R' is independently hydrogen or lower alkyl, or lower alkenyl or lower alkynyl where the unsaturated bond is at least one carbon removed from the O or N atom;

each R'' is independently R, lower alkoxy, NHR' or AOR'; and

A is an amino acid residue, or a peptide of 2 to 3 amino acid residues, which comprises cyclizing a compound of the formula:

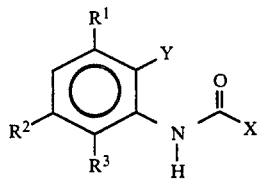

wherein $R^1$, $R^2$, $R^3$ and X are as defined above and Y is —C(O)OCH$_3$, —C(O)OC$_2$H$_5$, —C(O)OH, or Tl(OC(O)CF$_3$)$_2$; optionally followed by (a) converting a compound of formula (I) to its salt; or (b) converting a salt of the compound of formula (I) to the corresponding free compound of formula (I); or (c) converting a salt of the compound of formula (I) to another salt of the compound of formula (I); or (d) converting a compound of formula (I) to its pharmaceutically acceptable ester; or (e) converting a pharmaceutically acceptable ester of the compound of formula (I) to the free compound of formula (I).

2. A process for the preparation of compounds of the formula:

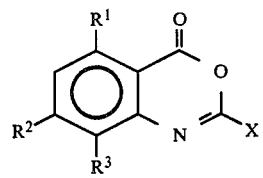

and the pharmaceutically acceptable esters and salts thereof, wherein $R^1$ is hydrogen or lower alkyl;

$R^2$ and $R^3$ are each independently hydrogen, halo, lower alkyl, hydroxy, lower alkoxy, lower thioalkyl, —NO$_2$, —N(R')$_2$, —NR'COR', —NHCON(R')$_2$ or —NHCOOR', with the proviso that at least one of $R^1$, $R^2$ and $R^3$ is not hydrogen when X is NHR or NR'COR''; and X is a radical chosen from the group consisting of:

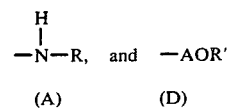

in which:

R is lower alkyl, lower alkenyl, lower alkynyl, optionally substituted lower cycloalkyl or optionally substituted phenyl lower alkyl;

each R' is independently hydrogen or lower alkyl, or lower alkenyl or lower alkynyl where the unsaturated bond is at least one carbon removed from the O or N atom;

each R'' is independently R, lower alkoxy, NHR' or AOR'; and

A is an amino acid residue, or a peptide of 2 to 3 amino acid residues, which comprises reacting a compound of the formula:

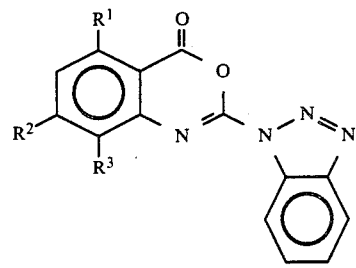

wherein $R^1$, $R^2$ and $R^3$ are as defined above, with a compound of the formula RNH$_2$ or AOR$^1$ wherein R and $R^1$ are as defined above followed by separation of the resulting mixture to obtain a compound of formula (I); optionally followed by (a) reaction of a compound of formula (I) wherein X is

with a compound of the formula R'—N=C=O wherein R' is as defined above to form a compound of formula (I) wherein

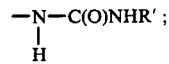

or (b) reacting a compound of formula (I) wherein X is

with a compound of the formula O=C=AOR' wherein R' is as defined above to form a compound of formula (I) wherein X is

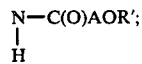

or (c) converting a compound of formula (I) to its salt; or (d) converting a salt of the compound of formula (I) to the corresponding free compound of formula (I); or (e) converting an acid addition salt of the compound of formula (I) to another salt of the compound of formula (I); or (f) converting a compound of formula (I) to its pharmaceutically acceptable ester; or (g) converting a pharmaceutically acceptable ester of the compound of formula (I) to the free compound of formula (I).

DETAILED DESCRIPTION OF THE INVENTION

Definitions

As used herein:

"Lower alkyl" means a branched or unbranched hydrocarbon chain containing 1 to 8 carbon atoms, including but not limited to methyl, ethyl, propyl, isopropyl, n-propyl, butyl, n-butyl sec-butyl, isobutyl, pentyl, hexyl, octyl and the like.

"Lower alkoxy" means the group —O—lower alkyl where lower alkyl has the definition given above.

"Lower thioalkyl" means the group —S—lower alkyl, where lower alkyl has the definition given above.

"Lower alkenyl" means a branched or unbranched unsaturated hydrocarbon chain of 2 to 8 carbon atoms, including but not limited to ethylene, propylene, 1-butene, 2-butene, isobutylene, 1-pentene, 1-hexene, cis-2-butene, trans 2-butene, cis-2-pentene, trans-2-pentene, 3-methyl-1-butene, 2-methyl-2-butene and 2,3-dimethyl-2-butene.

"Lower alkynyl" means a branched or unbranched unsaturated hydrocarbon chain of 2 to 8 carbon atoms which contains a carbon-carbon triple bond, including but not limited to acetylene, propyne, 1-butyne, 1-pentyne, 1-hexyne, 2-butyne, 2-pentyne, 3-methyl-1-butyne, -2-hexyne, 3-hexyne, and 3,3-dimethyl-1-butyne.

"Optionally substituted lower cycloalkyl" means a saturated hydrocarbon ring of 3 to 6 carbon atoms, optionally substituted with 1 to 5 substituents selected independently from the group consisting of lower alkyl, lower alkenyl, lower alkoxy, amino, halo, nitro, lower alkyl amino, or lower dialkylamino. Examples of lower cycloalkyl groups are cyclopropyl, cyclobutyl, cyclohexyl, methyl cyclohexyl, chloro cyclobutyl.

"Optionally substituted phenyl lower alkyl" refers to a phenyl ring attached to an alkyl chain of one to six carbon atoms and optionally substituted with one to three substituents selected independently from the group consisting of lower alkyl, lower alkenyl, lower alkoxy, amino, halo, nitro, lower alkyl amino, or lower dialkylamino.

"Halo" refers to fluoro, chloro, bromo and iodo.

"Amino" refers to the group —$NH_2$.

"Lower alkylamino" refers to an amino group substituted by lower alkyl as is defined above. Examples of lower alkylamino are methylamino, ethylamino and n-butylamino.

"Lower dialkylamino" refers to an amino group substituted by two lower alkyl groups. Examples of "lower dialkylamino" are dimethylamino, dipropylamino and methylethylamino.

"Pharmaceutically acceptable non-toxic alkyl esters" refers to alkyl esters formed from free acids of Formulas IB and ID of this invention. They are derived from branched or straight chain hydrocarbons having from one to twelve carbon atoms, and are formed at the carboxylic acid terminus of the 2-amino substituent.

Typical pharmaceutically acceptable, non-toxic alkyl ester groups are, for example, methyl, ethyl, propyl, isopropyl, butyl, t-butyl, isoamyl, pentyl, isopentyl, hexyl, octyl, nonyl, isodecyl, 6-methyldecyl and dodecyl esters.

"Pharmaceutically acceptable, non-toxic salts" refers to pharmaceutically acceptable salts of the compounds of this invention which retain the biological activity of the parent compounds and are not biologically or otherwise undesirable (e.g. the salts are stable). Salts of two types may be formed from the compounds of this invention: (1) Salts of inorganic and organic bases may be formed from compounds of Formulas IB and ID which have a carboxylic acid functional group. (2) Acid addition salts may be formed at the amine functional group of many of the compounds of this invention.

Pharmaceutically acceptable salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Pharmaceutically acceptable, non-toxic salts derived from organic bases include salts of primary, secondary, and tertiary amines and substituted amines including naturally occurring substituted amines, cyclic amines and basic ion exchange resins. Such salts are exemplified by, for example, isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabramine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, dicyclohexylamine, choline and caffeine.

Pharmaceutically acceptable acid addition salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Amino acid residue" means any of the naturally occurring alpha-, beta- and gamma-amino carboxylic acids, including their D and L optical isomers and racemic mixtures thereof, and N-lower alkyl- and N-phenyl lower alkyl-derivatives of these amino acids. The amino acid residue is bonded through a nitrogen of the amino acid. The naturally occurring amino acids which can be incorporated in the present invention include, but are not limited to, alanine, arginine, asparagine, aspartic acid, cysteine, cystine, glutamic acid, glutamine, glycine, histidine, isoleucine, leucine, lysine, methionine, ornithine, phenylalanine, proline, serine, threonine, thyroxine, tryptophane, tyrosine, valine, beta-alanine, and gamma-aminobutyric acid. N-lower alkyl- and N-phenyl lower alkyl-substituted amino acids which can be incorporated in the present invention include, but are not limited to N-methyl leucine, N-benzyl glycine, and N-ethyl glycine. Preferred amino acid residues include proline, leucine, phenylalanine, isoleucine, alanine, γ-amino butyric acid, valine, glycine, and phenylglycine.

The "X" moiety of compounds of Formula I may include a peptide of 2 to 3 amino acid residues. Preferred peptides include, but are not limited to, -prolyl-phenylalanine, -prolyl-leucine, -prolyl-isoleucine, leucyl glycine, isoleucyl glycine, -leucyl-leucine, -leucyl-phenylalanine, leucyl valine, their corresponding N-methyl derivatives, and other combinations of the preferred amino acid residues described above including their N-methyl derivatives.

All alpha-amino acids except glycine contain at least one asymmetric carbon atom. As a result, they are optically active, existing in either a D or L form, or as a racemic mixture. Accordingly, some of the compounds of the present invention may be prepared in optically active form, or as racemic mixtures. The present invention includes all optical isomers, as well as racemic mixtures of the compounds claimed herein.

The term "animal(s)" refers to humans as well as all other animal species, particularly mammals (e.g. dogs, cats, horses, cattle, pigs, etc.), reptiles, fish, insects and helminths.

The compounds of this invention are named as 4H-3,1-benzoxazin-4-ones using the numbering system set forth in the "Background of the Invention."

For example, the compound of Formula I where X is isopropylamino, $R^1$ is methyl, and $R^2$ and $R^3$ are hydrogen, is named 2-isopropylamino-5-methyl-4H-3,1-benzoxazin-4-one.

The compound of Formula I in which X has the formula —NR'COR" where R' and R" are each methyl, $R^1$ is methyl, and $R^2$ and $R^3$ are hydrogen is named 2-(N-methylacetylamino)-5-methyl-4H-3,1-benzoxazin-4-one.

The compound of Formula I where $R^1$, $R^2$ and $R^3$ are each hydrogen, and X has the formula —AN(R')$_2$ in which A is leucyl and each R' is hydrogen, is named N-(4H-3,1-benzoxazin-4-on-2-yl)-leucinamide.

The compound of Formula I where $R^1$ is ethyl, $R^2$ and $R^3$ are hydrogen, and X has the formula —AOR' in which A is L-leucyl and R' is methyl, is named N-(5-ethyl-4H-3,1-benzoxazin-4-on-2-yl)-L-leucine methyl ester.

Preferred Compounds

A preferred subclass of the invention includes compounds of Formula I in which $R^1$ is lower alkyl, most preferably methyl or ethyl. $R^2$ and $R^3$ may or may not be hydrogen.

Another preferred subclass of the invention are compounds of Formula I in which $R^2$ is not hydrogen. Of these, more preferred are compounds in which $R^2$ is lower alkyl, most preferably methyl or ethyl, lower alkoxy, most preferably methoxy, hydroxy, lower thioalkyl, or —N(R')$_2$. Among these, most preferred $R^2$ substituents are methyl, ethyl, methoxy and amino. $R^1$ and $R^3$ may or may not be hydrogen.

Yet another preferred subclass of the invention includes compounds of Formula I in which both $R^1$ and $R^2$ are not hydrogen. Of these, more preferred are compounds in which $R^1$ is lower alkyl and $R^2$ is lower alkyl, lower alkoxy, hydroxy, lower thioalkyl or —N(R')$_2$. Among these, most preferred are compounds of Formula I in which $R^1$ is methyl or ethyl and $R^2$ is methyl, ethyl, methoxy or amino. In this subclass, $R^3$ is preferably hydrogen.

At the present time, the most preferred compounds of this invention are:
2-isopropylamino-5-methyl-4H-3,1-benzoxazin-4-one;
5-ethyl-2-isopropylamino-4H-3,1-benzoxazin-4-one;
7-acetylamino-2-isopropylamino-4H-3,1-benzoxazin-4-one;
7-amino-2-isopropylamino-4H-3,1-benzoxazin-4-one;
2-isopropylamino-5-methoxy-4H-3,1-benzoxazin-4-one;
2-isopropylamino-8-methyl-4H-3,1-benzoxazin-4-one;
7-ethyl-2-isopropylamino-4H-3,1-benzoxazin-4-one;
7-(3-isopropylureido)-2-isopropylamino-4H-3,1-benzoxazin-4-one;
7,8-dimethyl-2-isopropylalmino-4H-3,1-benzoxazin-4-one;
5,8-dimethyl-2-isopropylamino-4H-3,1-benzoxazin-4-one;
5,7-dimethyl-2-isopropylamino-4H-3,1-benzoxazin-4-one;
2-n-butylamino-5-ethyl-4H-3,1-benzoxazin-4-one;
2-n-butylamino-5-methyl-4H-3,1-benzoxazin-4-one;
2-n-butylamino-8-methyl-4H-3,1-benzoxazin-4-one;
2-n-butylamino-5,7-dimethyl-4H-3,1-benzoxazin-4-one;
2-n-butylamino-8-methyl-4H-3,1-benzoxazin-4-one;
7-amino-2-n-butylamino-4H-3,1-benzoxazin-4-one;
2-benzylamino-8-methyl-4H-3,1-benzoxazin-4-one;
2-n-benzylamino-6,7-dimethoxy-4H-3,1-benzoxazin-4-one;
N-(5-methyl-4H-3,1-benzoxazin-4-on-2-yl)-L-leucine methyl ester;
N-(5,7-dimethyl-4H-3,1-benzoxazin-4-on-2-yl)-L-leucine methyl ester; and
N-(5-ethyl-4H-3,1-benzoxazin-4-on-2-yl)-L-leucine methyl ester;
2-isopropylamino-5-methyl-7-methoxy-4H-3,1-benzoxazin-4-one;
5-ethyl-2-isopropylamino-7-methoxy-4H-3,1-benzoxazin-4-one;
2-isopropylamino-5-methyl-7-amino-4H-3,1-benzoxazin-4-one;
7-amino-5-ethyl-2-isopropylamino-4H-3,1-benzoxazin-4-one;
N-(6,7-dimethoxy-4H-3,1-benzoxazin-4-on-2-yl)-D-phenylglycine methyl ester;
N-(5-ethyl-4H-3,1-benzoxazin-4-on-2-yl)-D-phenylglycine methyl ester;
N-(4H-3,1-benzoxazin-4-on-2-yl)-4-aminobutyric acid;
N-(4H-3,1-benzoxazin-4-on-2-yl)-D-phenylglycine methyl ester;
N-(4H-3,1-benzoxazin-4-on-2-yl)-L-prolyl-L-leucyl glycinamide;
N-(4H-3,1-benzoxazin-4-on-2-yl)-L-prlyl-L-leucinamide;
N-(4H-3,1-benzoxazin-4-on-2-yl)-D-leucine methyl ester;
N-(4H-3,1-benzoxazin-4-on-2-yl)-D,L-phenylglycine methyl ester.

Method of Preparation

The novel compounds of the present invention are represented by the formula:

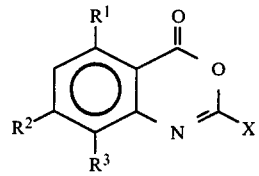

and the pharmaceutically acceptable esters and salts thereof, wherein:

$R^1$ is hydrogen or lower alkyl;

$R^2$ and $R^3$ are each independently hydrogen, halo, lower alkyl, hydroxy, lower alkoxy, lower thioalkyl, —$NO_2$, —N(R')$_2$, —NR'COR', —NHCON(R')$_2$ or —NHCOOR', with the proviso that at least one of $R^1$, $R^2$ and $R^3$ is not hydrogen when X is NHR or NR'COR''; and X is a radical chosen from the group consisting of:

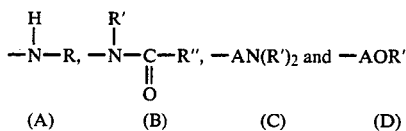

in which:

R is lower alkyl, lower alkenyl, lower alkynyl, optionally substituted lower cycloalkyl, optionally substituted phenyl lower alkyl;

each R' is independently hydrogen or lower alkyl, or lower alkenyl or lower alkynyl where the unsaturated bond is at least one carbon removed from the O or N atom;

each R'' is independently R, lower alkoxy, NHR' or AOR'; and

A is an amino acid residue, or a peptide of 2 to 3 amino acid residues.

A. Compounds in which X is NHR (Formula IA).

Compounds of the invention in which X is —NHR (compounds of Formula IA) may be prepared by any of three procedures which are outlined in Reaction Schemes I and II. The choice between these methods is readily made by one of ordinary skill in the art, and is usually based on availability of the starting materials.

REACTION SCHEME I

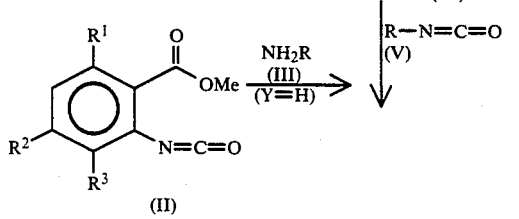

-continued
REACTION SCHEME I

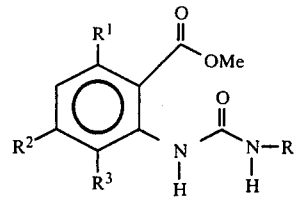

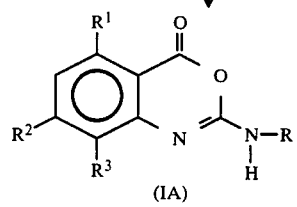

As outlined in Reaction Scheme I, the compounds of Formula IA are prepared by cyclization of the corresponding ureido-benzoate of Formula VI with sulfuric acid. The ureido-benzoate may be prepared by either of two methods, depending upon the availability of starting materials.

1. When each of $R^1$, $R^2$ and $R^3$ is hydrogen, Compound VI is readily prepared by condensation of 2-carbomethoxyphenyl isocyanate (Formula II in which Y is hydrogen) with the appropriate amine of Formula III. The 2-carbomethoxyphenyl isocyanate is readily commercially available, as are most mono-alkyl amines of Formula III.

The condensation of compounds II and III is carried out conveniently by bringing the reactants together in the presence of an inert organic solvent such as ether, tetrahydrofuran, pentane, hexane and like aliphatic hydrocarbons, benzene, and toluene. A preferred solvent is tetrahydrofuran. The reaction takes place at room temperature over a period of about 3 to 48 hours, usually about 6 hours. The resulting solid is then isolated and purified by conventional means.

In carrying out the above reaction and those described below, isolation and purification of the final compounds and intermediates caan be effected by any suitable separation or purification means known in the art such as, for example, filtration, extraction, crystallization, column chromatography, thin-layer chromatography or thick layer chromatography, high performance liquid chromatography, or a combination of these procedures. Specific illustration of suitable separation and isolation procedures can be had by reference to the examples hereinbelow. However, other equivalent separation or isolation procedures can be used.

The above-described process may also be used to prepare compounds of Formula VI bearing $R^1$, $R^2$ and $R^3$-substituents other than hydrogen. Variously substituted 2-carbomethoxyphenyl isocyanate starting materials can be prepared by reacting the correspondingly substituted methyl anthranilate with phosgene or trichloromethyl chloroformate, according to literature methods such as that reported by N. P. Peet and S. Sunder (J. Org. Chem., 39, 1931 (1974). An example of the synthesis of a substituted 2-carbomethoxyphenyl isocyanate of Formula II is given in Preparation I, below.

2. Alternatively, the ureido-benzoate of Formula VI can be made by reacting a methyl 2-aminobenzoate (Formula IV) with the isocyanate compound of Formula V, employing the method described by E. P. Papadopoulos et al (*Journal of Heterocyclic Chemistry*, 298, 1982), and illustrated in Preparation V, below. Variously substituted methyl 2-amino benzoates (methyl anthranilates) are commercially available, or can be prepared by treating the corresponding anthranilic acid with diazomethane in an inert organic solvent such as tetrahydrofuran or, preferably, either at about 0° C., a method that is standard for the formation of methyl esters. An example of the preparation of a compound of Formula IV by this method is described in Preparation II, below. Alternatively, variously substituted methyl 2-amino benzoates can be prepared by treating the corresponding isatoic anhydride with methanol in the presence of base such as sodium methoxide or dimethylaminopyridine, preferably dimethylaminopyridine, according to the literature methods such as that reported by M. C. Venuti, *Synthesis*, 266 (1982), R. P. Straiger and E. B. Miller, *J. Org. Chem.*, 24, 1214 (1959). The isocyanate of Formula V is either commercially available or can be prepared by reacting the corresponding amine with phosgene or trichloromethyl chloroformate, using standard methods such as that detailed in Preparation III, below.

The ureido-benzoate of Formula VI, prepared by either of the above methods, is subsequently cyclized in concentrated sulfuric acid to give the compounds of Formula IA. The reaction takes place at room temperature, with stirring, and is completed within about 1 to 12 hours, usually about 2-½ hours. The reaction solution is then poured into an ice-cold basic solution such as sodium bicarbonate or potassium bicarbonate, preferably sodium bicarbonate solution. The final product, a compound of Formula IA, is then isolated by conventional means.

3. Alternatively, the compounds of Formula IA can be made by the process shown in Reaction Scheme II.

REACTION SCHEME II

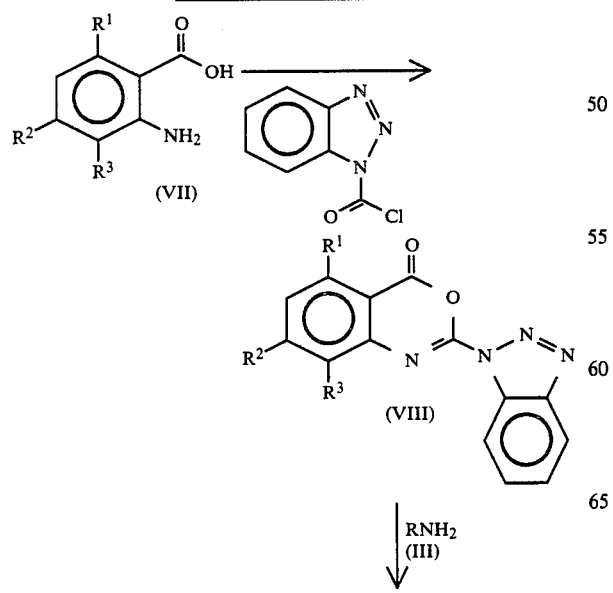

-continued
REACTION SCHEME II

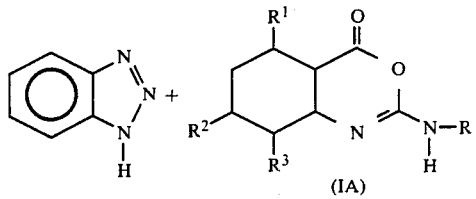

In Reaction Scheme II, the Compound VIII, an optionally substituted 2-(1-benzotriazolyl)-4H-3,1-benzoxazin-4-one is first prepared by treating an appropriately substituted anthranilic acid (Compound VII) with about two molar equivalents of 1-benzotriazolecarboxylic acid chloride in the presence of about two molar equivalents of triethylamine in an inert solvent such as benzene, tetrahydrofuran or, preferably, toluene, at about −10° to 10° C., preferably 0° C., for a period of about 2 to 8 hours, preferably about 4 hours. The reaction is carried out advantageously in accordance with the procedure described by I. Butala et al., in *Croatica Chemica Acta*, 54:1, pp. 105–108, (1981), and illustrated in Preparation VII, below.

The substituted anthranilic acids (Formula VII) used in preparing the compounds of this invention are either commercially available, or can be prepared by methods well known in the art. The commercially available anthranilic acids include, but are not limited to, 3-methylanthranilic acid, 4-methyl anthranilic acid, 5-methylanthranilic acid, 6-methyl-anthranilic acid, 5-iodoanthranilic acid, 4-nitro-anthranilic acid, 4,5-dimethoxy-anthranilic acid. A list of commercially available anthranilic acids is available in *Chem. Sources*-U.S.A., 24th Ed., 1983, Directories Publishing Company, Inc., Ormond Beach, Fla. Anthranilic acids which are not commercially available can be readily prepared by methods known in the art. Suitable methods include those of B. R. Baker, et al., *J. Org. Chem.*, 17, 141, (1952) and of L. A. Paquette, et al., *J. Am. Chem. Soc.* 99, 3734, (1981). The former method involves the preparation of an isatin from a substituted aniline derivative. Subsequent oxidation of the isatin gives the anthranilic acid. The latter procedure employs the reduction of the corresponding aromatic nitro-derivative to the anthranilic acid. These methods are further illustrated in Preparation VI below.

The reaction of an appropriate amine of Formula III with an appropriately substituted 2-(1-benzotriazolyl)-4H-3,1-benzoxazin-4-one of Formula VIII is carried out conveniently by combining approximately equi-molar amounts of the reactants in the presence of an inert inorganic solvent such as chloroform, toluene, or, preferably, methylene chloride. Removal of the benzotriazole created in this reaction yields the substituted 4H-3,1-benzoxazin-4-one of Formula IA.

B. Compounds in which X is

  (Formula IB)

As illustrated in Reaction Scheme III, below, compounds of the invention in which X is —NR'COR" (compounds of Formula IB) are prepared from the corresponding compounds of Formula IA by one of two methods, depending on the definition of R". Compounds of Formula IB in which R" is equal to R are designated by Formula IB-1, and Compounds of Formula IB in which R" is NHR' and AOR' are designated by Formula IB-2 and Formula IB-3 respectively.

REACTION SCHEME III

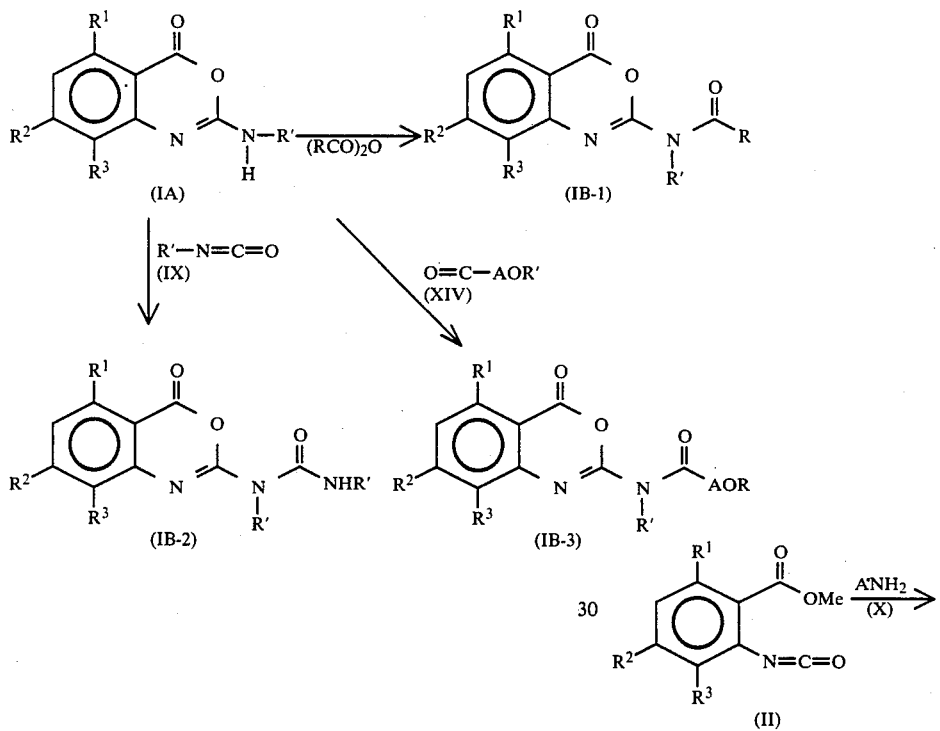

In the above reaction scheme, the desired compound of Formula IA is prepared according to the methods described in Section A above or any other method which may be apparent from the disclosure herein. When treated with an appropriate anhydride and pyridine in the presence of a catalytic amount of dimethylaminopryidine, the compound of Formula IA is converted to its corresponding amido derivative of Formula IB-1. Alternatively when a compound of Formula IA is refluxed in an inert organic solvent such as benzene, tetrahydrofuran, or for example, toluene, with an isocyanate of Formula IX (in which R" is NHR'), the corresponding urea derivative, a compound of Formula IB-2, (in which R" is NHR') is formed. Similarly, when a compound of Formula IA is refluxed in an inert organic solvent such as benzene, tetrahydrofuran, or preferably toluene, with an isocyanate of Formula XIV, the corresponding urea derivative of compound IA, a compound of Formula IB-3 is formed. Isocyanates of Formula IX and Formula XIV are readily commercially available, or may be prepared by treating the corresponding amine hydrochloride with trichloromethyl chloroformate in dioxane at approximately 50°-70° C., preferably 60° C. for a period of about 4 to 10, usually, 6 hours. This procedure is carried out in accordance with the method reported by K. Kurita, T. Matsmura and Y. Iwakuren, *J. Org. Chem.* 41, 2070, (1976), and is further described in Preparations III and XI, below.

C. Compounds in which X is —AN(R')₂ (Formula IC).

Compounds of the invention in which X has the formula —AN(R')₂ (compounds of Formula IC) are prepared from the corresponding appropriately substituted 2-carbomethoxyphenyl isocyanate of Formula II, as illustrated by Reaction Scheme IV, below:

REACTION SCHEME IV

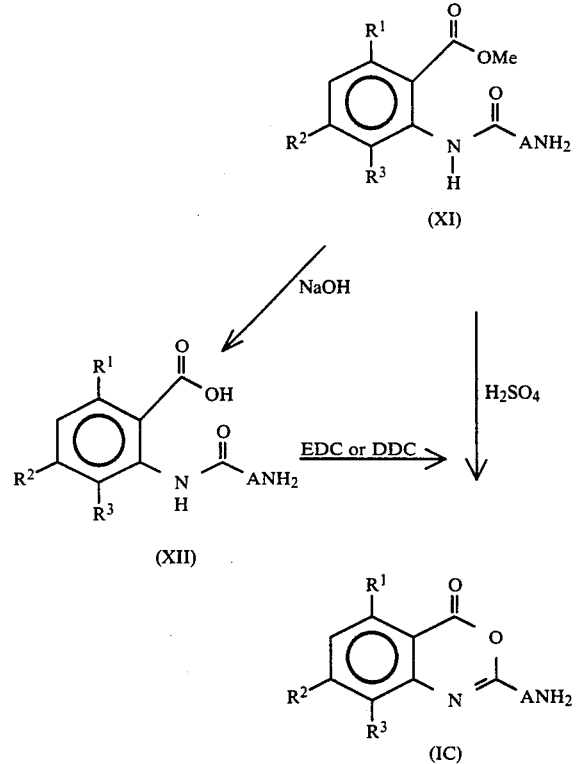

In the above reaction scheme, the compounds of Formula XI are prepared by condensation of an optionally substituted 2-carbomethoxyphenyl isocyanate of Formula II and an amino acid amide of Formula X or peptide amide in an inert organic solvent such as, for example, tetrahydrofuran, dimethylformamide, or a tetrahydrofuran:dimethylformamide cosolvent system. The amino acid amides of Formula X are commercially available. Dipeptide amides can easily be prepared by treating the carbobenzyloxy derivative of an amino acid with one molar equivalent of 1,1-carbonylidiimidazole at room temperature for 1 to 6 hours, preferably 2 hours at room temperature. The resulting acyl imidazole derivative is then reacted with a desired amino acid amide to give the carbobenzyloxy derivative of the dipeptide amide. Subsequent hydrogenation of the carbobenzyloxy derivative of the dipeptide amide over 5% palladium hydroxide on charcoal at about 30 to 40 psi hydrogen, followed by isolation and recrystallization, affords the corresponding dipeptide amide. This method of synthesizing dipeptide amides is described in the literature by Gross and Meienhofer in the *The Peptides, Analysis, Synthesis and Biology*, Academic Press, New York, 1981. The synthesis of dipeptides of Formula X is further illustrated in Preparation VIII, below.

Many tripeptides are commercially available and can be readily converted to their corresponding peptide amides by methods known in the art. Representative procedures for such conversions are documented in Greenstein and Winitz, *Chemistry of Amino Acids*, Vol 2, p 1110 & p 1187 (John Wiley & Sons, Inc., N.Y., 1961). Tetrapeptides and pentapeptides can be synthesized by standard methods known in the art. The synthesis of peptides are best described in Greenstein & Winitz, ibid. A detailed list of n-carbobenzoxy-protected peptides can be found on pp 1112–1148 in the reference cited above. These synthetic n-carbobenzoxy-protected peptides can readily be converted to the free amino terminal peptide amides and esters by catalytic hydrogenation with palladium hydroxide on charcoal. The deprotection of N-carbobenzoxy protected peptides by catalytic hydrogenation has been illustrated in Preparation VIII.

Once obtained, the compound of Formula XI, a 1-N-(2-carbomethoxyphenyl)-carbamoyl-amino acid amide, is then converted to the corresponding compound of Formula IC by one of two methods which are described below.

When the amino-terminal of the amino acid or peptidyl functional group (defined herein by "A") is an N-disubstituted amino acid derivative, the compound of Formula IC is preferably prepared by hydrolysis of the corresponding compound of Formula XI followed by dehydration and cyclization of the resulting Compound of Formula XII. Examples of N-disubstituted amino acid derivatives are proline and N-methyl leucine. These are amino acid derivatives in which the N-terminal of the amino acid carries a secondary amine functional group. The synthesis of various N-disubstituted amino acids may be accomplished by any of several methods known in the art. See for example, N. L. Benoiton et al., *Can. J. Chem.*, 1915 (1973); 1968 (1971); 2562 (1973), 916 (1977), and Greenstein and Winitz, *Chemistry of the Amino Acids*, Vol 3, p. 2751. (John Wiley and Sons, New York, 1961)

The hydrolysis of a compound of Formula XI is achieved by reaction with about one molar equivalent of sodium hydroxide, at room temperature, for about 4 hours to 3 days, normally about 6 hours, thereby yielding the corresponding 1-N-(2-carboxyphenyl)-carbamoyl amide of Formula XII. The acid derivative of Formula XII then reacts with a dehydrating agent such as N,N-dicyclohexylcarbodiimide (DDC) or, preferably, 1-(3-dimethylaminopropyl)-3-ethyl carbodiimide (EDC), to give the 4H-3,1-benzoxazin-4-one of Formula IC. This reaction is carried out in an inert organic solvent such as dry tetrahydrofuran at about 15° to 40° C. for a period of about 3 to 24 hours, usually about 6 hours, and the final product is isolated by conventional means.

Alternatively, when the amino-terminal of the "A" moiety is a primary amine, as is usually the case, the compound of Formula XI is preferably cyclized in concentrated sulfuric acid to give the corresponding 4H-3,1-benzoxazin-4-one of Formula IC. The reaction takes place in concentrated sulfuric acid at about 0° to 30° C., preferably around 25° C., over a period of about 2 to 12, usually about 3 hours. The final compound of Formula IC is then isolated by conventional means.

Compounds of this invention in which X is $ANH_2$ can also be prepared by reacting an amino acid amide or peptidyl amide of Formula X with a compound of Formula VIII, as illustrated in Reaction Scheme VI for AOR'. The details of this reaction are described in Section D, and in Example VIII below.

D. Compounds in which X is AOR' (Formula ID).

Compounds of the invention in which X is AOR' can be prepared by either of two methods, as illustrated by Reaction Schemes V and VI, below.

REACTION SCHEME V

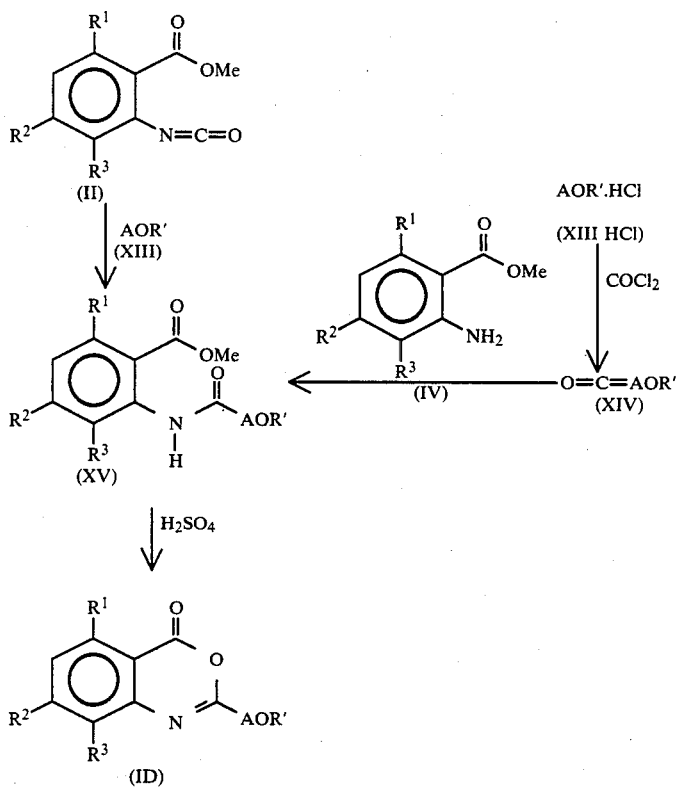

As illustrated above, compounds of Formula ID are prepared by condensation of the appropriately substituted 2-carbomethoxyphenyl isocyanate of Formula II with a salt of an amino acid ester or peptide ester of Formula XIII, followed by cyclization with sulfuric acid. The amino acid esters of Formula XIII are commercially available, as are many di- and tripeptide esters. Those which are not, as well as longer tetra- and pentamino acid esters, can be readily prepared by well known established methods such as those described by Greenstein and Winitz, in *Chemistry of the Amino Acids,* Vol. 1, 2 & 3, John Wiley and Sons Inc., New York, 1961; and by Gross and Meienhofer in *The Peptides, Analysis, Synthesis and Biology,* Academic Press, New York, 1981. For example, di-, tri, tetra- and pentapeptides can be synthesized by standard techniques, and subsequently converted to esters. As set out in the above discussion of the synthesis of peptide amides of Formula X, synthetic N-carbobenzoxy-protected peptides can be readily converted to the free amino-terminal esters by catalytic hydrogenation with palladium hydroxide on charcoal. The amino acid and peptide esters which are commercally available are usually available as hydrochloride salts, and are used as such to prepare the corresponding isocyanates of Formula XIV. These salts are easily converted to free amino acid esters with one molar equivalent of a base such as triethylamine.

The reaction of Compounds II and XIII is carried out in an inert organic solvent such as N,N-dimethylformamide, or preferably, tetrahydrofuran, at room temperature, over a period of 3 to 16 hours, usually about 6 hours, until completed. The resulting 1-N-(2-carbomethoxyphenyl)-carbamoyl-amino acid- or-peptidyl-ester of Formula XV is then isolated by conventional means.

Alternatively, an amino acid or peptidyl ester of Formula XIII can be converted to its isocyanate (Compound XIV), and then reacted with an appropriately substituted methyl anthranilate of Formula IV to give the compound of Formula XV. The conversion of Compound XIII to the corresponding isocyanate of Formula XIV is accomplished by reacting an amino acid ester with phosgene or diphosgene, according to methods well known in the art, such as that described by Patai in [The Chemistry of Cyanates and their Thiol Derivatives, Parts I and II, John Wiley and Sons, New York, 1977. This method is illustrated by way of example in Preparation XI, below. Additionally, some of the isocyanates of Formula XIV, such as the isocyanate of glycine ethyl ester, are commercially available. Subsequent reaction of Compound XIV with an appropriately substituted methyl anthranilate of Formula IV, at reflux temperature in toluene or another inert organic solvent such as benzene or tetrahydrofuran over a period of about 10 to 40 hours, affords the ureido-benzoate of Formula XV. Subsequent cyclization of Compound XV in concentrated sulfuric acid affords the corresponding 4H-3,1-benzoxazin-4-one of Formula ID. The reaction takes place in concentrated sulfuric acid, at about 0° to 30° C., preferably around 25° C. over a period of about 2 to 12 hours, usually about 3 hours. The final compound of Formula ID is then isolated by conventional means.

Compounds of the invention in which X is AOR' can also be prepared by reacting an amino acid ester or peptidyl ester of Formula XIII with a compound of Formula VIII, as illustrated in Reaction Scheme VI, below:

REACTION SCHEME VI

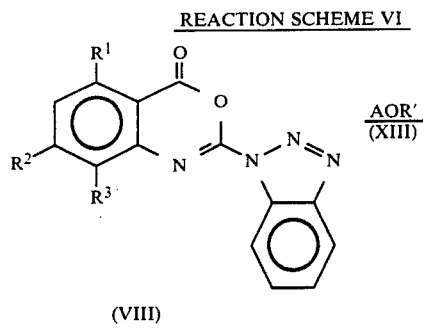

(VIII)

$\xrightarrow{\text{AOR'}}_{(XIII)}$

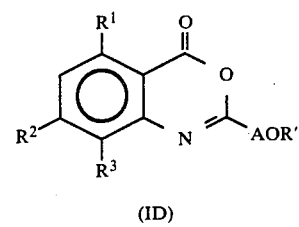

(ID)

REACTION SCHEME VII

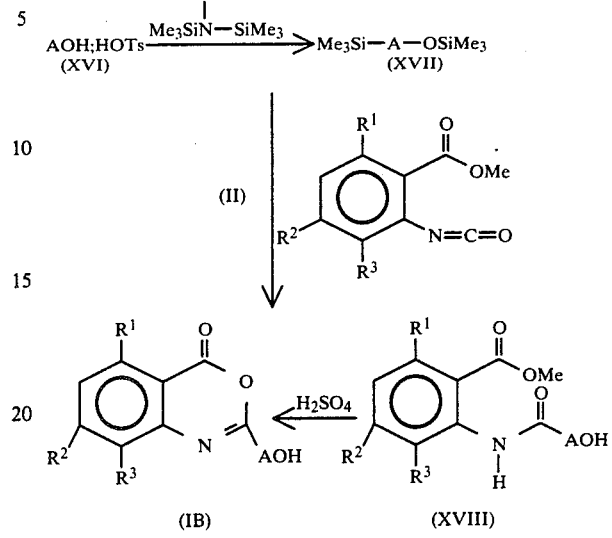

The compound of Formula VIII, an optionally substituted 2-(1-benzotriazolyl)-4H-3,1-benzoxazin-4-one, is prepared as described above in Section A. The reaction of Compounds VIII and XIII takes place in an inert solvent, preferably methylene chloride, at about 0° to 10° C., until completed, over a period of about 3 to 6, usually about 3 hours. The benzotriazole eliminated during the reaction is removed by selective recrystallization from toluene or flash chromatography over silica gel using ethyl acetate-hexane as an eluant or by conventional thick layer chromatography on silica gel. This method of making compounds of Formula ID is further illustrated by Example VIII.

Compounds of Formula ID in which R' is hydrogen may be prepared as described in the preceding paragraphs, but are preferably prepared by the method shown below in Reaction Scheme VII.

In the above Reaction Scheme VII, a compound of Formula XVI, a paratoluenesulfonic acid (HOTs) salt of an amino acid or peptide, is reacted with a silylating agent, such as trimethylsilylchloride or, prefererably, hexamethyldisilizane. The paratoluenesulfonic acid salt may be prepared by reacting an appropriate acid or peptide with p-toluenesulfonic acid in a solvent such as dimethoxyethane, according to the method of A. Anieta and C. Paloma, *Synthesis,* 1050, (1982). This method is illustrated by way of example in Preparation XV, below. The reaction of compounds XVI and hexamethyldisilizane takes place in an inert organic solvent such as methylene chloride at about 20°-30° C. over a period of about 1-3 hours. The resulting disilylated amino acid or peptide (Compound XVII) is then reacted with a 2-carbomethoxyphenyl isocyanate of Formula II to give the compound of Formula XVIII. Subsequent cyclization of Compound XVIII in concentrated sulfuric acid yields the corresponding compound of Formula ID in which R' is hydrogen.

E. Alternative Method of Preparing Compounds in which X is NHR, AN(R'), and AOR'₂ (Formulas IA, IC and ID).

Compounds of this invention in which X is NHR, AN(R')₂ or AOR' can alternatively be prepared by the method shown in Reaction Scheme VIII below:

REACTION SCHEME VIII

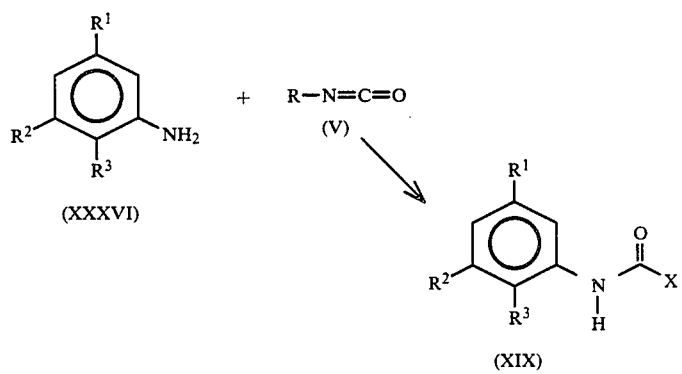

REACTION SCHEME VIII

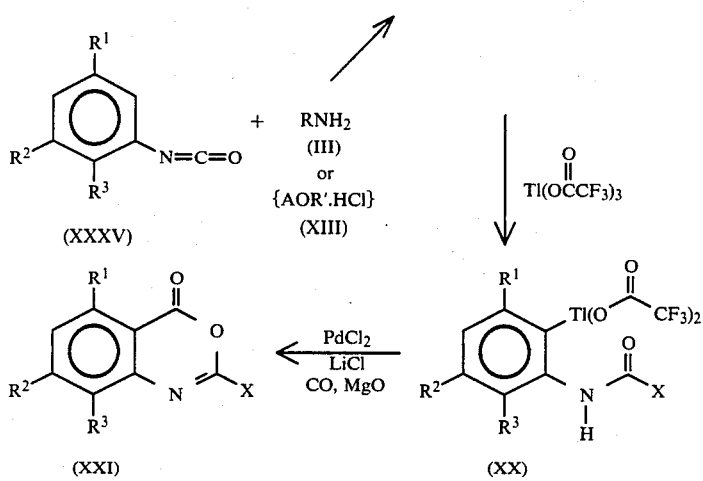

In this method, phenyl urea of Formula XIX is thallated with thallium trifluoroacetate in trifluoroacetic acid and an inert solvent such as tetrahydrofuran or methanol. The thallation reaction is normally carried out at room temperature with one equivalent of thallium trifluoroacetate in a 20% solution of trifluoroacetic acid in tetrahydrofuran from 4 hours to 2 days in the dark. The normal reaction time is about 10 to 12 hours. The phenyl urea of Formula XIX is readily prepared by reaction of an isocyanate of Formula V or XXXV with an amine of Formula III or XXXVI. The choice of reagents is readily made by one of ordinary skill in the art and is usually based on the availability of starting materials at the time. More detailed descriptions of the synthesis of phenyl ureas of Formula XIX are given in Preparation XVI hereinbelow.

After the thallation reaction is completed, the intermediate of Formula XX is isolated by solvent evaporation. Residual trifluoroacetic acid is removed by azeotroping with dichloroethane under reduced pressure. The crude thallated compound of Formula XX is carbonylated in tetrahydrofuran in the presence of about 2 to 2.5, preferably 2.2, equivalents of lithium chloride, about 1-1.5, preferably 1.2, equivalents of magnesium oxide and about 0.1 equivalents of palladium chloride under about 0.5 to 1.5, preferably 1, atmospheres of carbon monoxide. The reaction normally takes 8 to 16 hours, preferably 12 hours. The compound of Formula XXI is purified by conventional column chromatography and recrystallization.

While thallation of other aromatic compounds is known in the art, (see, for example, R. C. Larock and C. A. Fellows, *J. Am. Chem. Soc.* 1980, 104, 1900–1907, 1982 and *J. Org. Chem.* 45, 363–365, 1980). The above-described conversion of a phenyl urea to a benzoxazinone by thallation and subsequent carbonylation is a novel synthetic procedure.

F. Compounds of Formula I(A), I(C) and I(D) in which $R^2$ or $R^3$ is $NH_2$, NHCOR', or NHCON(R')$_2$.

Compounds of Formula I(A), I(C) and I(D) in which either $R^2$ or $R^3$ is —$NH_2$, —NHCOR' or —NHCON(R')$_2$ can, in addition to previously described methods, be prepared as shown in Reaction Scheme IX, below, in which X is —NHR, —AN(R')$_2$ or —AOR'.

REACTION SCHEME IX

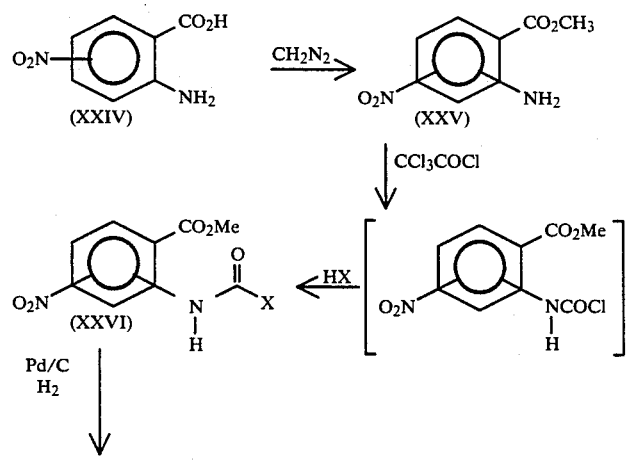

REACTION SCHEME IX

-continued

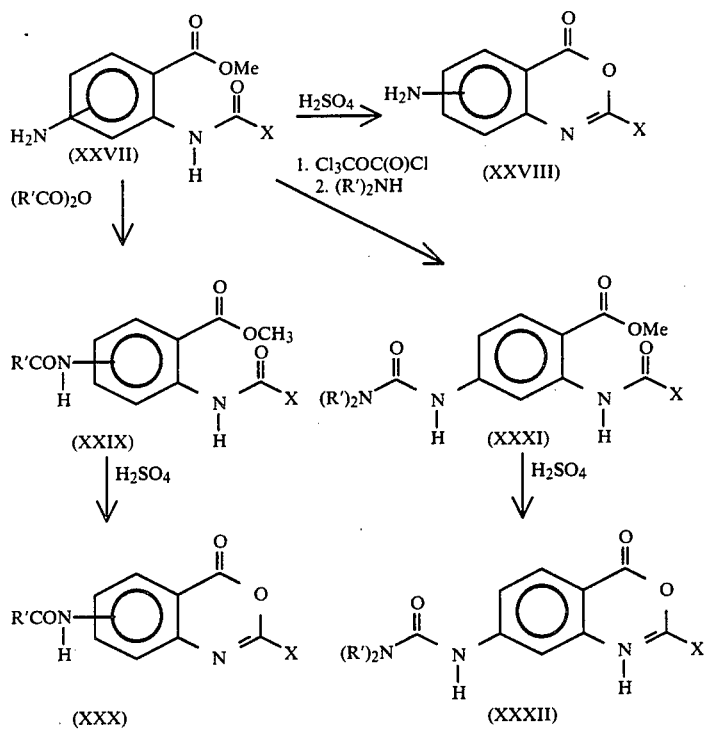

As shown above, a nitro substituted anthranilic acid of Formula XXIV can be converted to its corresponding methyl ester with diazomethane. The resulting compound of Formula XXV reacts with about 0.6 to 0.8 equivalents of trichloromethyl chloroformate in ethyl acetate to give the corresponding carbamoyl chloride derivative. The reaction is carried out at room temperature for a period of about 2 to 4 hours. Reactions of this type are known and described in the chemical literature (see M. Takaski, T. Junzo, Jpn. Kokai Tokyo Koho, 79 05, 942, Jan. 17, 1979, CA. 91, 56666t). The carbamoyl chloride is quenched with a 3-fold excess amine to give the urea of Formula XXVI after conventional purification procedures.

The resulting nitro compound (Formula XXVI) is then hydrogenated over 10% palladium on charcoal at room temperature at about 35–50 psi hydrogen to give the corresponding amino compound of Formula XXVII. The solvent for hydrogenation is normally ethyl acetate or absolute ethanol. In the case where the urea is ortho to the carbomethoxy group (see Formula XXVII), the compound is cyclized in concentrated sulfuric acid to give the benzoxazinone of Formula XXXVIII. The conditions for the cyclization are similar to those described in Section A, above. The amino compound of Formula XXVII can be acylated with an acid anhydride to give compounds of Formula XXIX. This compound is similarly cyclized in concentrated sulphuric acid to give the benzoxazinone of Formula XXX.

In a manner similar to the conversion of compound Formula XXV to compound Formula XXVI, the amino compound of Formula XXVII is converted to the diurea of Formula XXXI. The resulting diurea is then converted to the benzoxazinone of (Formula XXXII) in sulphuric acid in the usual manner.

G. Compounds of the Invention in which $R^1$ is alkyl (particularly methyl), $R^2$ is lower alkoxy, $R^3$ is hydrogen and X is —NHR, AN($R'$)$_2$ or —AOR$'$.

Compounds of Formulas I(A), I(C) or I(D) in which $R^1$ is alkyl (particularly methyl), $R^2$ is lower alkoxy and $R^3$ is H, can in addition to any previously described methods, be prepared as shown in Reaction Scheme X, below (R is methyl or ethyl). In Formulas 1 to 4,

REACTION SCHEME X

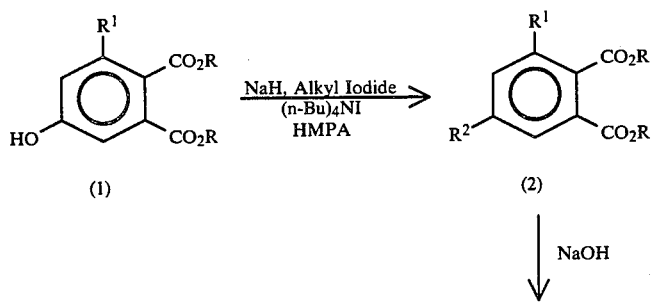

REACTION SCHEME X

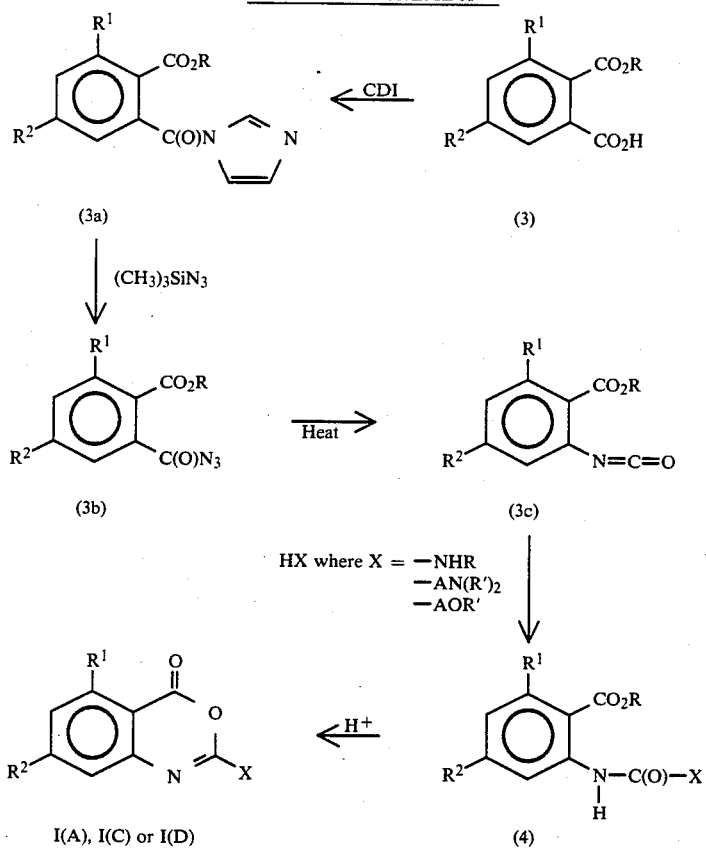

Compound 1 (where $R^1$ is alkyl) is prepared by the Diels-Alder reaction between 4-hydroxy-6-alkyl-2-pyrone and dimethyl acetylene dicarboxylate at 170° C. (see Alder, Rickert, Bento, 1354 [1937]). Alternatively (1) is also prepared by the Diels-Alder reaction between (E)- and (Z)-2,4-bis(trimethylsiloxy)-penta-1,3-diene and diethyl acetylene decarboxylate at the refluxing temperature of toluene. The compound is isolated by standard means. Compound (1) is converted to the corresponding alkoxy (particularly methoxy) ether by treating with about 1 equivalent of sodium hydride, alkyl (esp. methyl)iodide (about 5 equivalents), and tetra-n-butylammonium iodide (0.2 eq. to 2 eq.) in a mixture of tetrahydrofuran and HMPA for a period of 2 to 4 hours. The resulting ether (2) is isolated by standard methods in the art. Compound (2) is selectively hydrolyzed to the monoacid (3) with 2% sodium hydroxide in a 1:1 mixture of water and alcohol for a period of 3 hours. The resulting acid (3) is further purified by recrystallization and is dried at about 40°-80° C., preferably about 60° C., preferably about 8 hours under high vacuum. The monoacid is treated with about 1 equivalent of 1,1-carbonyl-diimidazole (CDI) at room temperature for about 30 minutes under argon. A 10-fold excess of trimethylsilyl azide is added and the resulting solution refluxed for about 2 hours. The material is evaporated to dryness. Toluene is added and the resulting mixture is refluxed for 12 hours. The solution is cooled and about 2 equivalents of $NH_2R$, $HAN(R')_2$ or $HAOR'$, wherein R, R' and A are as defined in the broadest aspect of the invention, are added. The resulting product (4) is isolated by standard chromatographic techniques. Compound (4) is converted to I(A), I(C) or I(D) by stirring (4) in a concentrated acid (e.g. sulphuric acid) for about 3 hours and isolating the product by standard means.

H. Compounds of Formula IA, IC or ID in which $R^1$ is alkyl, $R^3$ is hydrogen and $R^2$ is $NH_2$, NHCOR' or $NHCON(R')_2$.

Compounds of Formula I(A), IC and I(D) in which $R^1$ is alkyl, $R^3$ is hydrogen and $R^2$ is —$NH_2$, —NHCOR' or —$NHCON(R')_2$ can, in addition to any appropriate previously described methods, be prepared as shown in Reaction Scheme XI, below:

REACTION SCHEME XI

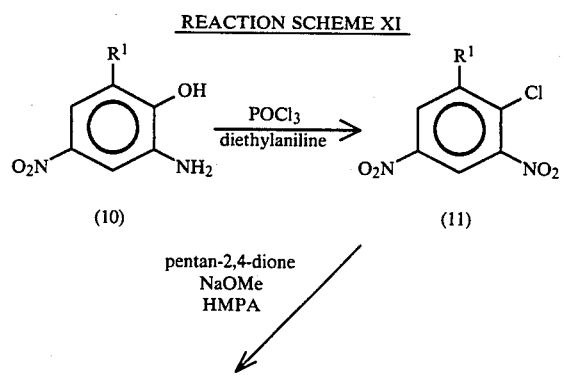

-continued
REACTION SCHEME XI

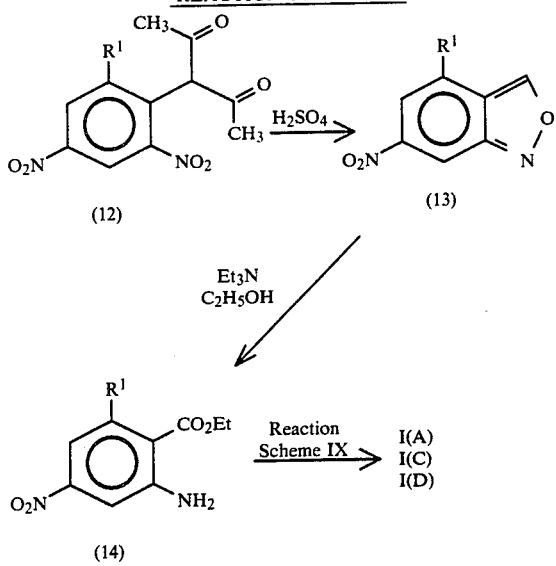

As shown above, the phenol derivative of Formula 10, which is either commercially available or readily prepared by standard known methods, is converted to the corresponding chloro-compound of Formula 11 according to the procedure described by B. Boothroyd and E. R. Clark, *J. Chem. Soc.*, p. 1504, London (1953). The compound of Formula 11 is then reacted at room temperature with about a 10 fold excess of pentan-2,4-dione and about a 3–4 fold excess of sodium methoxide in the presence of HMPA as a solvent, to give the (2-alkyl-4,6-dinitrophenyl)-diacetylmethane of Formula 12. The compound of Formula 12 is then cyclized in concentrated sulphuric acid at about 100°-120° C., preferably 110° C., for a period of 1–5, preferably 3 hours, to give the 4-alkyl6-nitro anthranil of Formula 13. This procedure is described in greater detail by I. R. Gambir and S. S. Joshi in the *Indian Chem. Soc. Journal*, 41, pp. 43-46 (1964). Subsequent ring opening by treating the anthranil of Formula 13 with triethylamine and ethanol at reflux temperature gives the ethyl 4-nitro-6-alkyl-2-amino benzoate of Formula 14.

Compounds of Formulas I(A), I(C) and I(D) are prepared from the compound of Formula 14 by the procedures shown in Reaction Scheme IX, substituting the compound of Formula 14 for the compound of Formula XXVII.

Certain compounds of this invention form acid addition salts, i.e., those wherein X contains a basic group such as a dialkylamino, an arginine, substituted arginine, guanidine or substituted guanidine, or wherein Y is dialkylamino. In these compounds, the free base form may be converted to various acid addition salts by treating with a stoichiometric excess of the appropriate organic or inorganic acid, such as, for example, phosphoric, pyruvic, hydrochloric or sulfuric acid and the like. Typically, the free base is dissolved in a polar organic solvent such as p-dioxane or dimethoxyethane, and the acid added thereto. The temperature is maintained between about 0° C. and 50° C. The resulting acid addition salt precipitates spontaneously or may be brought out of solution with a less polar solvent.

The acid addition salts of the compounds of Formulas IA-ID may be decomposed to the corresponding free base by treating with a stoichiometric amount of a suitable base, such as potassium carbonate or sodium hydroxide, typically in the presence of aqueous solvent, and at a temperature of between about 0° C. and 50° C. The free base form is isolated by conventional means, such as extraction with an organic solvent.

Acid addition salts of the compounds of the invention may be interchanged by taking advantage of differential solubilties of the salts, volatilities or acidities of the acids, or by treating with an appropriately loaded ion exchange resin. For example, the interchange is effected by the reaction of a salt of the compounds of Formula I with a slight stoichiometric excess of an acid of a lower pKa than the acid component of the starting salt. This conversion is carried out at a temperature between about 0° C. and the boiling point of the solvent being used as the medium for the procedure.

In summary, then, the compounds of Formula I can be prepared by the following last-step procedures:

I. Cyclization of a compound of Formula VI with concentrated sulfuric acid to give a compound of Formula IA;

II. Reaction of a compound of Formula III with a compound of Formula VIII to give a compound of Formula IA;

III. Derivatization of a compound of Formula IA to give a compound of Formula IB-1;

IV. Reaction of a compound of Formula IA with a compound of Formula IX to give a compound of Formula IB-2;

V. Dehydration of a compound of Formula XII with a dehydrating agent such as EDC or DDC to give a compound of Formula IC;

VI. Cyclization of a compound of Formula XI with concentrated sulfuric acid to give a compound of Formula IC;

VII. Cyclization of a compound of Formula XV in concentrated sulfuric acid to give a compound of Formula ID;

XVIII. Reaction of a compound of Formula VIII with a compound of Formula XIII to give a compound of Formula ID; and IX. Cyclization of a compound of Formula XVIII with concentrated sulfuric acid to give a compound of Formula ID.

X. Reaction of a compound of Formula I with a stoichiometric excess of an acid to give a pharmaceutically acceptable non-toxic acid addition salt.

XI. Thallation and subsequent carbonylation of a compound of Formula XIX to give a compound of Formula XXI.

XII. Cyclization of a compound of Formula XXIX or Formula XXXI with concentrated sulfuric acid to give a compound of Formula XXX or Formula XXXII.

XIII. Cyclization of a compound of Formula 4 with concentrated sulfuric acid to give a compound of Formula IA, IC or ID.

Utility and Administration

The 2-amino-4H-3,1-benzoxazin-4-ones disclosed herein have been discovered to be active inhibitors of a variety of serine protease enzymes, including human leukocyte elastase, human thrombin, human urokinase, porcine acrosin, porcine pancreatic elastase, bovine chymotrypsin and human and bovine trypsin. Because these compounds function as slow-deacylating alternate substrates they are expected to be useful inhibitors of many other types of physiologic enzymes such as kallikreins, plasmin, and various plasminogen activators.

Because enzyme pathways are implicated in a wide variety of physiologic conditions and disease states, the compounds of this invention have many potential therapeutic utilities. For example, because they are highly active inhibitors of human leukocyte elastase, they may be used to treat and control emphysema, adult respiratory distress syndrome and rheumatoid arthritis. Because they are active inhibitors of human and bovine trypsin, the 2-amino-4H-3,1-benzoxazinones of this invention may be used in the treatment of pancreatitis.

Generally, when treating disease states by enzyme inhibition, it is desirable that the enzyme inhibitor be selective for the particular enzyme, or class of enzymes, involved in propagating the disease. Accordingly, an important aspect of this invention involves the discovery that the compounds of Formula I are strongly selective for serine proteases over thiol proteases. Routinely, differences of five orders of magnitude are observed between the inhibitory activity of compounds of Formula I against serine proteases and their inhibitory activity against thiol proteases. This is a very important advantage of the invention, which would not have been expected due to the fact that thiol proteases catalyze hydrolysis of esters and amides via mechanisms very similar to those of serine proteases.

Also, when treating disease states by enzyme inhibition, it is desirable that the enzyme inhibitors be stable in the blood. Accordingly, another important aspect of this invention involves the discovery that enhanced stability of the compounds of Formula I can be achieved by appropriate combination of substituents at positions 2-, 5-, 7- and/or -8.

The compounds of Formulas IA, IB, IC, and ID have been shown in standard laboratory tests to inhibit a variety of serine protease enzymes, including human leukocyte elastase, human thrombin, human urokinase, porcine acrosin, porcine pancreatic elastase, bovine chymotrypsin, and human and bovine trypsin. Accordingly, the compounds of the invention, their salts, esters, and/or pharmaceutical compositions thereof, may be used in inhibiting, preventing, or controlling physiologic conditions and disease states in animals which are known to involve serine proteases, or may be used as contraceptives.

Knowledge of the roles of enzymes in a wide variety of diseases is constantly growing. Recent reviews of the state of the art include "Protein Degradation in Health and Disease", Ciba Foundation Symposium 75, Excerpta Medica, Amsterdam, 1980; "Proteinases in Mammalian Cells and Tissues", A. J. Barrett, ed., North Holland Publishing Company, Amsterdam, 1977; and "Proteases and Biological Control", E. Reich, D. B. Rifkin and E. Shaw, eds., Cold Spring Harbor Laboratory, 1975.

Experimental evidence has revealed the roles of many enzymatic pathways in various physiologic conditions and disease states. Plasminogen activator (PA), a serine protease, causes the conversion of plasminogen to plasmin which in turn is responsible for fibrinolysis. This process is implicated in a number of systems requiring controlled local proteolysis, including inflammation (J. D. Vassalli, et al. *Cell*, 8, 271 [1976]), and cell migration and tissue remodeling, J. E. Valinski, *Cell*, 25, 471 (1981). The production and secretion of PA is also correlated with certain human disorders such as arthritis (Neats, et al., *Nature* [London], 286, 891, 1980; Hamilton, et al., *J. Exp. Med.*, 155, 1702 [1982]) and the expression of transformed phenotypes, D. B. Rifkin, et al., in *Proteases and Biological Control*, D. Rifkin, E. Reich, E. Shaw, eds., Cold Spring Harbor, 1975, pp. 841–847.

There is considerable evidence that plasminogen activator (such as urokinase), leukocyte elastase, and/or related enzymes play a role in tumor cell metastasis (Salo, et al., *Int. J. Cancer*, 30, 669–673, 1973; Kao, et al., *Biochem. Biophys., Res. Comm.*, 105, 383–389, 1982; Powers, J. C., in *Modification of Proteins*, R. E. Feeney and J. R. Whitaker, eds., Adv. Chem. Ser. 198, Amer. Chem. Soc., Wash., D.C., pp. 347–367, 1982), suggesting that compounds of this invention may have antimetastatic activity.

Other evidence suggests an antiparasitic role for the compounds of this invention (Aoki, T., et al., *Mol. Biochem., Parasitol*, 8, 89–97, 1983).

Pulmonary emphysema is a disease characterized by a progressive loss of lung elasticity due to the destruction of lung elastin and alveoli. It is widely held that the destructive changes in lung parenchyma associated with pulmonary emphysema are mediated in large part by unrestrained proteolytic activity in lung connective tissue. (A. Janoff, *Chest*, 83, 54–58 [1983]). A number of proteases have been shown to induce emphysematous lesions in animals when instilled in lungs (V. Marco, et al., Am. Rev. Respir. Dis., 104, 595–8, 1971; P. D. Kaplan, *J. Lab. Clin. Med.*, 82, 349–56 (1973)). In particular, human leukocyte elastase has been shown to produce emphysema in animals (A. Janoff, ibid, 115, 461–78 (1977)). Prophylactic administration of an inhibitor of elastase significantly diminishes the extent of elastase induced emphysema in hamsters (J. Kleinerman, et al., ibid, *Am. Rev. Respir. Dis.*, 121, 381–7, 1980).

Leukocyte elastase and other mediators of inflammation appear to play a role in such acute and high-risk diseases as mucocutaneous lymph node syndrome (Reiger, et al, *Eur. J. Pediatr.*, 140, 92–97, 1983), and adult respiratory distress syndrome (Stockley, R. A., *Clinical Science*, 64, 119–126, 1983; Lee, et al., *N. Eng. J. Med.*, 304, 192–196, 1981; Rinaldo, ibid, 301, 900–909, 1982.

Oral anticoagulants are some of the most important drugs for the prevention and treatment of a variety of venous and, to a lesser extent, arterial thromboembolic disorders (R. A. O'Reilly in "The Pharmacological Basis of Therapeutics", 6th Ed., A. G. Goodman, L. S. Goodman, A. Gilman, eds., 1980). The enzymes that participate in the cascade leading to blood coagulation are proteases. The coagulation of blood entails the formation of fibrin by the interaction of more than a dozen proteins in a cascading series of proteolytic reactions. Inhibition of these proteinases should block fibrin formation and hence inhibit coagulation. For example, inhibition of thrombin limits the formation of fibrin and is regarded as an approach to thromboembolic therapy.

However, anticoagulants that are in current use and that affect clotting factors do not have a direct onset of action. Consequently, prothombin time must be monitored, as the degree of Vitamin K antagonism varies from individual to individual.

Thus there is a critical need for new anticoagulants which have a direct onset of action. Pulmonary embolism (PE), for example, is a common complication that usually affects patients who are hospitalized for other medical or surgical problems (A. A. Sasahara, et al., JAMA, 249, 2945 (1983) and references therein). The mortality of undiagnosed and therefore untreated PE is relatively high, ranging from about 18% to 35%. Patients undergoing total hip or knee replacement are at extremely high risk for development of deep vein thrombosis, with a reported incidence of 45% to 70% in untreated patients S. Sagar, et al., *Lancet,* 1, 1151 (1978)).

Pancreatitis is a disease which affects large numbers of people including patients having acute alcoholic, acute biliary traumatic and post-operative pancreatitis. Furthermore, with the high incidence of alcoholism, 10,000,000 alcoholics in the U.S. alone, acute and chronic relapsing pancreatitis are seen with increasing frequency. Geokes, et al. has proposed that an effective therapy for acute pancreatitis might be achieved by the use of "a combination of low molecular weight specific active-site inhibitors for trypsin, chymotrypsin, and elastase", (*Am J. Pathol.,* 1981, 105, 31–39).

Proteolytic cleavage of precursors is an essential step in the replication of many animal viruses, and there is considerable evidence that protease inhibitors can be effective anti-viral agents (Korant, B. D., (1975) in "Proteases and Biological Control"). Such viruses include influenza (Chirov, O. P. et al. (1981) *Vopr. Virusol.,* 6, 677–687). In Sendai virus, for example, a host trypsin-like protease is essential for infectivity (Scheid, A., and Choppin, P. (1975) in "Proteases and Biological Control"). It is reasonable then that compounds of this invention could play a role in amelioration of viral diseases.

Acrosin is a unique serine proteinase which is present in mammalian sperm acrosomes (L. J. D. Zaneveld (1975) in "Proteases and Biological Control", pp. 683–706; R. F. Parrish, *Int. J. Biochem.,* 10, 391–395 (1979)). Since acrosin activity is required for fertilization, it is a rational target for birth control. Further, the inhibition of acrosin is known to prevent fertilization (Zaneveld, L. J. D., et al., (1979), Biol. Repr. 20, 1045–1054), supporting a role for acrosin inhibitors as contraceptives.

Initial screening tests to determine enzyme-inhibitory potential can be performed with commercially available enzyme substrates such as peptidyl amides of 4-methyl-7-amino coumarin or 4-nitroaniline. The assays are performed by mixing the substrate and enzyme of interest in an appropriate buffer, and monitoring the rate of enzyme inhibition spectrophotometrically. The reaction rate is monitored continuously either by fluorescence (for coumarin substrates) or absorbance (for nitroanilide substrates) until a constant reaction rate is established. A solution of the compound to be tested in an appropriate solvent, such as a 5 to 20 millimolar solution in dimethyl sulfoxide, is then added, and the increase in fluorescence or absorbance is monitored until a new stable rate is achieved. This is repeated for several concentrations of test compound solution, and the inhibition constant is calculated by non-linear multiple regression fit to the appropriate equation. The compounds of Formula I have been tested in assays of this type and have demonstrated marked inhibitory activity against human leukocyte elastase, human thrombin, human urokinase, porcine acrosin, porcine pancreatic elastase, bovine chymotrypsin and bovine trypsin. Some of the compounds of Formula I have also been tested and shown to be active in inhibiting the degradation of basement membrane by macrophages, tumor cells, and elastase. More detailed descriptions of several of these assays may be found in the Examples, below.

Administration of the active compounds and salts described herein can be via any of the accepted modes of administration for systemically active therapeutic medicaments. These methods include oral, parenteral and otherwise systemic, aerosol or topical forms.

Depending on the intended mode of administration, the compositions used may be in the form of solid, semisolid or liquid dosage forms, such as, for example, tablets, suppositories, pills, capsules, powders, liquids, aerosols, suspensions, or the like, preferably in unit dosage forms suitable for single administration of precise dosages. The compositions will include a conventional pharmaceutical carrier or excipient and an active compound of Formula IA-D or the pharmaceutically acceptable salts thereof and, in addition, may include other medicinal agents, pharmaceutical agents, carriers, adjuvants, etc.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* Mack Publishing Company, Easton, Pa., 15th Edition, 1975. The composition or formulation to be administered will, in any event, contain a quantity of the active compound(s) in an amount effective to alleviate the symptoms of the subject being treated.

For the compounds of Formula I, either oral or nasal (bronchial) administration is preferred, depending on the nature of the disorder being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 1%–95% active ingredient, preferably 25–70%.

Oral and nasal administration to the lungs can also be effected by aerosol delivery forms. For aerosol administration, the active ingredient is preferably supplied in finely divided form along with a surfactant and a propellent. Typical percentages of active ingredients are 0.01 to 20% by weight, preferably 0.04 to 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates or sorbitan, e.g., those sold under the trademarks "Arlacel C" (Sorbitan sesquioleate), "Span 80" (sorbitan monooleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the trademark "Freon." Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

For topical administration, these compositions comprise an effective amount of a compound of this class in admixture with a pharmaceutically acceptable non-toxic carrier. A suitable range of composition would be 0.1%–10% active ingredient, and the balance carrier, preferably 1–2% active ingredient. The concentration of active ingredient in pharmaceutical compositions suitable for topical application will vary depending upon the particular activity of the compound used in conjunction with the condition and subject to be treated. Suitable carriers or medicament vehicles for topical application of these compounds include creams, ointments, lotions, emulsions, solutions and the like.

For example, a suitable ointment for topical application of compounds of the invention contains 15 to 45 percent of a saturated fatty alcohol having 16 to 24 carbon atoms such as cetyl alcohol, stearyl alcohol, behenyl alcohol, and the like and 45 to 85 wt. percent of a glycol solvent such as propylene glycol, polyethylene glycol, dipropylene glycol, and mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms, e.g., stearic acid, palmitic acid, behenic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding monoester of other fatty acids such as oleic acid and plamitic acid; and 0 to 20 wt. percent of a penetrant such as dimethyl sulfoxide or dimethylacetamide.

The amount of active compound administered will of course, be dependent on the subject being treated, the severity of the affliction, the manner of administration and the judgment of the prescribing physician. However, an effective dosage is in the range of 1–100 mg/kg/day, preferably about 25 mg/kg/day. For an average 70 kg human, this would amount to 70 mg–7 g per day, or preferably about 1.5 g/day.

The following examples serve to illustrate the invention. They should not be construed as narrowing or limiting its scope.

PREPARATION I

A. Preparation of 6-Methyl-2-Carbomethoxyphenyl Isocyanate and Related Compounds of Formula II.

To 11 ml of condensed phosgene in 50 ml of ethyl acetate, was added 5 gm of methyl 2-amino-3-methyl benzoate at $-78°$ C. in 10 ml ethyl acetate. The mixture was warmed up to room temperature and then refluxed at 60° C. for about 1 hour. The solution was left at room temperature for 20 hours at which time white crystals had formed. The solution was filtered and the filtrate evaporated to give, as a brown solid, 6-methyl-2-carbomethoxyphenyl isocyanate.

NMR: (delta $CDCl_3$): 2.3 (s, 3H, Ar—$CH_3$), 3.95 (s, 3H, $OCH_3$), 7.0–7.4, 7.8 (m, 3H, ArH). IR: 2250, 1705 $cm^{-1}$, m.p. 55°–58° C.

B. In a similar manner, but replacing the methyl 2-amino-3-methyl benzoate with other appropriately substituted methyl anthranilates, the following compounds of Formula II. are prepared:
2-carbomethoxy-3-methyl-phenyl isocyanate;
2-carbomethoxy-4-methyl-phenyl isocyanate;
2-carbomethoxy-5-ethyl-phenyl isocyanate;
2-carbomethoxy-3-ethyl-phenyl isocyanate;
2-carbomethoxy-6-ethyl-phenyl isocyanate;
2-carbomethoxy-6-propyl-phenyl isocyanate;
2-carbomethoxy-6-hexyl-phenyl isocyanate;
2-carbomethoxy-3-methoxy-phenyl isocyanate;
2-carbomethoxy-4-ethoxy-phenyl isocyanate;
2-carbomethoxy-3-nitro-phenyl isocyanate;
2-carbomethoxy-3-dimethylamino-phenyl isocyanate;
6-acetamido-2-carbomethoxy-phenyl isocyanate;
2-carbomethoxy-6-(N-methyl-hexanamido)-phenyl isocyanate;
4-bromo-2-carbomethoxy-phenyl isocyanate;
2-carbomethoxy-5-chloro-phenyl isocyanate;
2-carbomethoxy-6-fluoro-phenyl isocyanate;
2-carbomethoxy-3,6-dimethyl-phenyl isocyanate;
2-carbomethoxy-4,5-dimethoxy-phenyl isocyanate;
2-carbomethoxy-3,4,5-trifluoro-phenyl isocyanate;
2-carbomethoxy-3-chloro-6-iodo-phenyl isocyanate; and
2-carbomethoxy-5-ethyl-3-methyl-phenyl isocyanate.

PREPARATION II

A. Preparation of Methyl-2-amino-6-methyl benzoate and related compounds of Formula IV.

To a solution of 1.5 gm of 2-amino-6-methyl benzoic acid in ether, was added a solution of diazomethane in ether dropwise at 0° C. The addition was continued until TLC analysis (40% ethyl acetate:petroleum ether) indicated that the reaction was completed ($R_f=0.7$). The excess diazomethane was destroyed by adding a small amount of silica gel to the solution. The solution was suction filtered through sintered glass. The silica gel was well washed with ether. The combined ethereal extract was evaporated to an oil. NMR(delta $CDCl_3$): 2.42 (s, 3H, $CH_3$), 3.88 (s, 3H, $OCH_3$), 5.08 (br, 2H, $NH_2$), 6.6–7.3 (m, 3H, Ar—H). IR: 3479, 3370, 1675, 1603, 1460, 1438 $cm^{-1}$.

B. In a similar manner, but replacing the 2-amino-6-methyl benzoic acid with other substituted anthranilic acids, the following compounds of Formula IV were prepared:
methyl 2-amino-3-methyl benzoate, as an oil;
methyl 2-amino-4,5-dimethoxy benzoate, as a semisolid;
methyl 2-amino-5-iodo benzoate, m.p. 84°–86° C.;
methyl 2-amino-4-nitro benzoate, 155°–157° C.; and
methyl 2-amino-6-methoxy benzoate, as an oil.

C. In like manner, the following compounds of Formula IV are prepared:
methyl 2-amino-6-ethyl benzoate;
methyl 2-amino-6-propyl benzoate;
methyl 2-amino-6-hexyl benzoate;
methyl 2-amino-3-methoxy benzoate;
methyl 2-amino-4-ethoxy benzoate;
methyl 2-amino-3-nitro benzoate;
methyl 2-amino-6-ethylamino benzoate;
methyl 2-amino-3-dimethylamino benzoate;
methyl 6-acetamido-2-amino benzoate;
methyl 2-amino-6-(N-methyl-hexanamido)benzoate;
methyl 2-amino-4-bromo benzoate;
methyl 2-amino-5-chloro benzoate;
methyl 2-amino-6-fluoro benzoate;
methyl 2-amino-3,6-dimethyl benzoate;
methyl 2-amino-4,5-dimethoxy benzoate;
methyl 2-amino-3,4,5-trifluoro benzoate;
methyl 2-amino-3-chloro-6-iodo benzoate; and
methyl 2-amino-6-bromo-5-ethyl-3-methyl benzoate.

PREPARATION III

A. Preparation of Benzyl Isocyanate and Related Compounds of Formula V and Formula IX.

To a suspension of 12 gm of benzylamine hydrochloride in dioxane, was added 8.3 gm of trichloromethyl chloroformate dropwise. The mixture was heated at 60° C. for 8 hours and cooled. The dioxane was removed under reduced pressure. The product isocyanate was isolated by vacuum distillation b.p. 60°–64° C. (1 mm Hg). IR: 2260 cm$^{-1}$; yield: 6 gm.

B. In a similar manner, but replacing the benzylamine hydrochloride with other appropriate primary amines, the following compounds of Formula V are prepared:
2-phenylethylisocyanate;
3-phenylpropyl isocyanate;
4-phenylbutyl isocyanate;
n-butyl isocyanate;
isopropyl isocyanate;
hexyl isocyanate;
octyl isocyanate;
2-propenyl isocyanate;
2-penten-4-ynyl isocyanate;
cyclopropyl isocyanate;
4-methyl-cyclohexyl isocyanate;
4-dimethylaminobenzyl isocyanate.

PREPARATION IV

A. Preparation of Methyl 2-(3-sec-butylureido)-Benzoate and Related Compounds of Formula VI.

250 mg of 2-carbomethoxyphenylisocyanate (Compound II), prepared as described in Preparation I above, and 0.145 ml of sec-butylamine in dry tetrahydrofuran were stirred at room temperature for about 8 hours. The solvent was removed under reduced pressure and the resulting solid was recrystallized from ether and petroleum ether to give methyl 2-(3-sec-butylureido)-benzoate, m.p. 124°–124° C.; $^1$H NMR:(delta CDCl$_3$); 0.95 (s, 3H, C$\underline{H}_3$ CH$_2$), 1,2(d, 3H, C$\underline{H}_3$CH), 1,5(m, 2H, CH$_3$C$\underline{H}_2$), 3.8 (m, 1H, C$\underline{H}$—N), 3.9 (s, 3H, OCH$_3$), 4.6 (broad s, 1H, CON$\underline{H}$—sec—Bu), 6.8, 7.2 (2 m, 2H, Ar—H), 8.0, 8.6 (2 dd, 2H, Ar—H), 10.3 (broad, 1H, ArNHCO).

The infrared spectrum of this material showed maxima at 3280, 1700, 1650, 1600 and 1585 cm$^{-1}$.

B. Similarily, but replacing the 3-sec-butylamine with another amine of Formula III, the following compounds of Formula VI are prepared:
methyl-2-(3-methylureido)-benzoate;
methyl-2-(3-n-hexylureido)-benzoate;
methyl-2-(3-n-octylureido)-benzoate;
methyl-2-(3-benzylureido)-benzoate;
methyl-2-(3-cyclohexylureido)-benzoate;
methyl-2-[3-(4-dimethylaminobenzyl)ureido]-benzoate;
methyl-2-(3-cyclohexylureido)-benzoate;
methyl 2-[3-(2-phenylethyl)-ureido]-benzoate;
methyl 2-[3-(3-phenylpropyl)-ureido]-benzoate;
methyl 2-[3-(4-phenylbutyl)-ureido]-benzoate;
methyl 2-[3-(5-phenylpentyl)-ureido]-benzoate;
methyl 2-[3-(1-phenylethyl)-ureido]-benzoate;
3-(2-[3-(2-carbomethoxyphenyl)-ureido]-ethyl)-indole;
4-(2-[3-(2-carbomethoxyphenyl)-ureido]-ethyl)-imidazole;
5-benzyloxy-3-(2-[3-(2-carbomethoxyphenyl)-ureido]-ethyl)-indole;
2-(2-[3-(2-carbomethoxyphenyl)-ureido]-ethyl)-pyridine;
3-(2-[3-(2-carbomethoxyphenyl)-ureido]-ethyl)-pyridine;
N-(2-[3-(2-carbomethoxyphenyl)-ureido]-ethyl)-morpholine;
N-(2-[3-(2-carbomethoxyphenyl)-ureido]-ethyl)-pyrrolidine;
1-N-(2-carbomethoxyphenyl)-carbamoyl-piperonylamine;
methyl 2-[3-(2-methylbenzyl)-ureido]-benzoate;
methyl 2-[3-(4-methylbenzyl)-ureido]-benzoate;
methyl 2-(3-propargylureido)-benzoate;
methyl 2-(3-furfurylureido)-benzoate; and
methyl 2-(3-n-butylureido)-benzoate.

C. In like manner, but replacing the 2-carbomethoxyphenylisocyanate with a substituted derivative prepared as described in Preparation I.B, and using the same or another appropriate amine, the following compounds of Formula VI are prepared:
methyl 2-[3-(4-dimethylaminobenzyl)-ureido]-benzoate;
methyl 6-methyl-2-(3-vinylureido)-benzoate;
methyl 6-methyl-2-(3-methylureido)-benzoate;
methyl 2-(3-isopropylureido)-6-methyl-benzoate;
methyl 2-(3-isopropylureido)-3-methyl-benzoate;
methyl 2-(3-n-butylureido)-6-methoxy-benzoate;
methyl 2-(3-n-butylureido)-6-methyl-benzoate;
methyl 2-(3-n-butylureido)-6-ethyl-benzoate;
methyl 2-(3-ethylureido)-5-chloro-benzoate;
methyl 2-(3-cyclohexylureido)-6-fluoro-benzoate;
methyl 2-(3-hexylureido)-3-nitro-benzoate;
methyl 4,5-dimethoxy-2-(3-n-propylureido)-benzoate;
methyl 2-(3-sec-butylamino)-3,6-dimethyl-benzoate;
methyl 3-chloro-2-(3-ethylureido)-4-iodo-benzoate;
methyl 2-(3-pentylureido)-3,4,5-trifluoro-benzoate;
methyl 6-bromo-5-ethyl-2-(3-isopropylureido)-3-methyl-benzoate; and
methyl 2-(3-benzylureido)-benzoate.

PREPARATION V

A. Alternate Preparation of Compounds of Formula VI.

Preparation of Methyl 2-(3-n-butylureido)-benzoate.

To a solution of 13.55 gm of methyl anthranilate in 12 ml dry tetrahydrofuran, was added 8.9 ml of n-butyl isocyanate dropwise. The solution was stirred for 5½ days and filtered. The filtrate was reduced to half of its original volume and further precipitated with hexane and filtered. The two residues were combined to yield the title compound as a white solid, m.p. 84°–85° C.; NMR(delta $CDCl_3$): 0.79, 1.02 (m, 3H, $CH_3$), 1.16–1.76 (m, 4H, $CH_2CH_2$), 3.27 (t, 2H, $NCH_2$), 3.87 (s, 3H, $OCH_3$), 4.82 (br, 1H, NH), 6.81–8.59 (m, 4H, ArH), 11.09 (s, 1H, NH). IR: 3305, 3260, 1708, 1642, 1560 $cm^{-1}$.

B. In a similar manner, but replacing the n-butyl isocyanate with other alkyl isocyanates prepared as described in Preparation III above, the following compounds of Formula VI were prepared:
methyl 2-(3-methylureido)-benzoate;
methyl 2-(3-ethylureido)-benzoate;
methyl 2-(3-propylureido)-benzoate;
methyl 2-(3-isopropylureido)-benzoate;
methyl 2-(3-benzylureido)-4-ethyl-benzoate;
methyl 2-(3-n-butylureido)-4-ethyl-benzoate;
methyl 2-(3-isopropylureido)-4-amino-benzoate;
methyl 2-(3-n-butylureido)-3-methyl-benzoate; and
methyl 2-(3-isopropylureido)-6-methoxy-benzoate.

C. Similarly, but replacing the methyl anthranilate with another appropriately substituted methyl 2-aminobenzoate, prepared as described in Preparation II above, and using the same or another appropriate isocyanates, prepared as described in Preparation III above, the following compounds of Formula VI were prepared:
methyl 2-(3-isopropylureido)-3-methyl-benzoate;
methyl 2-(3-isopropylureido)-6-methyl-benzoate;
methyl 2-(3-n-butylureido)-6-methoxy-benzoate;
methyl 2-(3-n-butylureido)-6-methylbenzoate;
methyl 2-(3-benzylureido)-3-methyl-benzoate; and
methyl 2-(3-benzylureido)-4,5-dimethoxy-benzoate.

D. In like manner, the following compounds of Formula VI are prepared:
methyl 6-acetamido-2-(3-benzylureido)-benzoate;
methyl 6-acetamido-2-(3-n-butylureido)-benzoate;
methyl 6-acetamido-2-(3-isopropylureido)-benzoate;
methyl 2-(3-benzylureido)-5-iodo-benzoate;
methyl 2-(3-n-butylureido)-5-iodo-benzoate;
methyl 2-(3-isopropylureido)-5-iodo-benzoate;
methyl 2-(3-benzylureido)-5-n-butyl-benzoate;
methyl 2-(3-n-butylureido)-5-n-butyl-benzoate;
methyl 5-n-butyl-2-(3-isopropylureido)-benzoate;
methyl 2-(3-benzylureido)-4-chloro-benzoate;
methyl 2-(3-n-butylureido)-4-chloro-benzoate;
methyl 4-chloro-2-(3-isopropylureido)-benzoate;
methyl 2-(3-benzylureido)-3,5-di-iodo-benzoate;
methyl 2-(3-n-butylureido)-3,5-di-iodo-benzoate;
methyl 3,5-di-iodo-2-(3-isopropylureido)-benzoate;
methyl 2-(3-n-butylureido)-4-ethyl-benzoate;
methyl 2-3-(benzylureido)-4-ethyl-benzoate;
methyl 4-ethyl-2-(3-isopropylureido)-benzoate;
methyl 2-(3-n-butylureido)-5-methyl-benzoate;
methyl 2-(3-isopropylureido)-5-methyl-benzoate;
methyl 2-(3-benzylureido)-5-methyl-benzoate;
methyl 2-(3-n-butylureido)-4-methyl-benzoate;
methyl 2-(3-benzylureido)-4-methyl-benzoate;
methyl 2-(3-isopropylureido)-4-methyl-benzoate;
methyl 5-acetamido-2-(3-benzylureido)-benzoate;
methyl 5-acetamido-2-(3-n-butylureido)-benzoate;
methyl 5-acetamido-2-(3-isopropylureido)-benzoate;
methyl 2-(3-benzylureido)-5,6-dimethyl-benzoate;
methyl 2-(3-benzylureido)-4,6-dimethyl-benzoate;
methyl 2-(3-benzylureido)-3,6-dimethyl-benzoate;
methyl 2-(3-benzylureido)-4,5-dimethyl-benzoate;
methyl 2-(3-benzylureido)-3,5-dimethyl-benzoate;
methyl 2-(3-benzylureido)-3,4-dimethyl-benzoate;
methyl 2-(3-n-butylureido)-5,6-dimethyl-benzoate;
methyl 2-(3-n-butylureido)-4,6-dimethyl-benzoate;
methyl 2-(3-n-butylureido)-3,6-dimethyl-benzoate;
methyl 2-(3-n-butylureido)-4,5-dimethyl-benzoate;
methyl 2-(3-n-butylureido)-3,5-dimethyl-benzoate;
methyl 2-(3-n-butylureido)-3,4-dimethyl-benzoate;
methyl 5,6-dimethyl-2-(3-isopropylureido)-benzoate;
methyl 4,6-dimethyl-2-(3-isopropylureido)-benzoate;
methyl 3,6-dimethyl-2-(3-isopropylureido)-benzoate;
methyl 4,5-dimethyl-2-(3-isopropylureido)-benzoate;
methyl 3,5-dimethyl-2-(3-isopropylureido)-benzoate;
methyl 3,4-diemthyl-2-(3-isopropylureido)-benzoate;
methyl 2-(3-n-butylureido)-6-ethyl-benzoate;
methyl 2-(3-methylureido)-3-methyl benzoate;
methyl 2-(3-ethylureido)-5-ethyl benzoate;
methyl 2-(3-n-propylureido)-6-propyl benzoate;
methyl 6-hexyl-2-(3-isopropylureido)benzoate;
methyl 2-(3-hexylureido)-3-methoxy benzoate;
methyl 4-ethoxy-2-[3-(2-propenylureido)]-benzoate;
methyl 2-(3-cyclopropylureido)-3-dimethylamino benzoate;
methyl 5-acetamido-2-[3-(4-methylcyclohexyl)ureido]-benzoate;
methyl 2-[3-(4-dimethylaminobenzyl)ureido]-6-fluoro benzoate;
methyl 2-(3-n-butylureido)-3,6-dimethyl benzoate;
methyl 4,5-dimethoxy-2-(3-methylureido)-benzoate;
methyl 2-(3-ethylureido)-3,4,5-trifluoro benzoate;
methyl 3-chloro-6-iodo-2-(3-n-propylureido)-benzoate; and
methyl 5-ethyl-2-(3-isopropylureido)-3-methyl-benzoate.

PREPARATION VI

Prepartion of Substituted anthranilic acids of Formula VII.

A. Preparation of 4-ethyl anthranilic acid and 6-ethyl-anthranilic acid.

4-ethyl anthranilic acid and 6-ethyl anthranilic acid were prepared according to Baker's procedure, as described in *J. Org. Chem.*, 17, 141, (1952) and further detailed below.

(i) Preparation of m-ethyl-alpha-isonitrosoacetanilide.

In a 5 liter round-bottom flask equipped with overhead stirrer and condensers were placed 74.2 gm. of chloral dihydrate and 900 ml of water. To this solution was then added, sequentially, 107.2 gm of anhydrous sodium sulfate, a solution of 50 gm of m-ethyl aniline dissolved in 248 ml of water and 42 ml of concentrated hydrochloric acid, and lastly, a solution of 90.8 gm of hydroxylamine hydrochloride in 412 ml of water. The mixture was slowly heated over a period of 45 minutes to a temperature of 95° C. The heating mantle was then removed and the flask rapidly cooled to room temperature by immersion in an ice-bath. The crude isonitrosoacetanilide was collected by suction filtration and washed with water. The produce was then further purified by the following procedure: The crude isonitrosoacetanilide was dissolved in 500 ml of a 4M sodium hydroxide solution, transferred to a separatory funnel and washed with ether (3×300 ml). The alkaline phase was then treated with charcoal, filtered through Celite and strongly acidified with concentrated hydrochloric acid. The precipitated m-ethyl-alpha-isonitrosoacetanilide was collected by filtration and dried under vacuum, m.p. 140°–142° C.

(ii) Preparation of 4-ethyl and 6-ethyl isatin.

A 1 liter round-bottom flask containing 370 ml of concentrated sulfuric acid and 30 ml of water was heated to 60° C.

m-Ethyl-alpha-isonitrosoacetanilide (64 gm) was added at such a rate as to maintain the temperature between 60° and 65° C. After the addition was completed, the mixture was heated to 80° C. for 10 minutes. The flask was then cooled to room temperature and poured onto 8 to 10 times its volume of ice. After standing for one-half hour, the crude isatin mixture was collected by filtration and washed well with water. The crude extract was then dissolved in about 300 ml of a 3M sodium hydroxide solution by heating on a steam bath, treated with charcoal and filtered through Celite. On acidification to pH 6–7 with concentrated hydrochloric acid, a gummy material appeared and was removed by filtration through Celite. The solution was then acidified to pH 4 and the 4-ethyl isatin was collected by filtration and washed with water: Yield 14.6 gm, m.p. 128°–136° C. The cooled filtrate was then strongly acidified with concentrated hydrochloric acid and collected by filtration to give the 6-ethyl isatin: Yield 16.4 gm (28%), m.p. 171°–173° C.

(iii) Preparation of 2-amino-4-ethyl-benzoic acid.

In a 500 ml flask, was placed 16.84 gm of 6-ethyl isatin which was covered with 216 ml of 1.5M sodium hydroxide solution. With stirring, the mixture was warmed to 50° C. Heating was discontinued and the solution was treated with a 30% solution of hydrogen peroxide (24 ml) which was added at such a rate to maintain the temperature at between 50° to 65° C. The mixture was left to slowly cool to room temperature and was then acidified to pH 4 with concentrated hydrochloric acid. The precipitated product was then collected by filtration: m.p. 117°–120° C.; yield 8.93 gm.

(iv) Preparation of 2-amino-6-ethyl-benzoic acid.

Oxidation of 9.6 gm of 4-ethyl isatin according to the method described in (iii), above, gave 7.3 gm of the title compound: m.p. 99°–104° C.

B. In a similar manner, but replacing m-ethyl aniline with other analines, the following exemplary compounds of Formula VII are prepared.
5-n-butyl-anthranilic acid;
4-iodo-anthranilic acid; and
6-iodo-anthranilic acid.

C. Preparation of 6-methoxyanthranilic acid by reduction of the corresponding aromatic nitro compounds was carried out in accordance with Paquette's procedure, *J. Am. Chem. Soc.*, 99, 3734, (1984), m.p. 71°–75° C.

D. In a similar manner, but replacing the starting m-dinitro-benzene in Paragraph C, above, with other aromatic nitro compounds, the following compounds are prepared:
6-acetylamino-anthranilic acid;
5-amino-anthranilic acid; and
6-amino-anthranilic acid.

PREPARATION VII

A. Preparation of 2-(1-Benzotriazolyl)-5-Methyl-4H-3,1-Benzoxazin-4-One, and Related Compounds of Formula VIII.

A solution of 960 mg of 6-methyl anthranilic acid in 30 ml of dry toluene containing 1.77 ml of dry triethylamine, which had been stirred for 30 minutes, was added to a solution of 2.1 gm of 1-benzotriazole carboxylic acid chloride in 30 ml toluene over a period of 30 minutes, and stirred for 12 hours. The resulting precipitate was filtered. The filtrate was reduced to one-half of its initial volume, and the resulting solids isolated by filtration. The combined residues were washed with water, dried under high vacuum and recrystallized from chloroform, giving 400 mg of 2-(1-benzotriazolyl)-5-methyl-4H-3,1-benzoxazin-4-one, m.p. 214°–215° C. (decomp.).

B. In like manner, but replacing the 6-methylanthranilic acid with other appropriately substituted anthranilic acids, prepared as described in Preparation VI above, or with unsubstituted anthranilic acid, the following compounds of Formula VIII were also obtained:
2-(1-benzotriazolyl)-4H-3,1-benzoxazin-4-one, m.p. 195°–198° C.; and
2-(1-benzotriazolyl)-5-ethyl-4H-3,1-benzoxazin-4-one m.p. 115°–116° C.

C. Similarly, the following compounds of Formula VIII are obtained:
2-(1-benzotriazolyl)-7-ethyl-4H-3,1-benzoxazin-4-one;
2-(1-benzotriazolyl)-7-iodo-4H-3,1-benzoxazin-4-one;
2-(1-benzotriazolyl)-5-iodo-4H-3,1-benzoxazin-4-one; and
2-(1-benzotriazolyl)-5-methoxy-4H-3,1-benzoxazin-4-one.

PREPARATION VIII

A. Preparation of N-Methyl-L-Leucyl-L-Phenylalaninamide and Related Dipeptides of Formula X and XIII.

To a solution of 1.28 gm of CBZ-N-methyl leucine in 25 ml of dry tetrahydrofuran, was added 0.743 gm 1,1-carbonyldiimidazole and the solution was stirred for 3 hours at room temperature. A solution of 0.75 gm of phenylalanine amide in 25 ml of dry tetrahydrofuran was added and the mixture was stirred at room temperature for 8 hours.

Solvent evaporation gave a solid which was partitioned between ethyl acetate (100 ml×2) and 5% hydrochloric acid (60 ml). The organic layer was washed with sodium bicarbonate solution and dried over magnesium sulfate. Solvent evaporation gave a solid which was hydrogenated over palladium hydroxide on charcoal in ethanol at 35 psi hydrogen for 12 hours. The solution was filtered, evaporated to a solid, and recrystallized from chloroform:hexane to give 800 mg of N-methyl-L-leucyl-L-phenylalaninamide, m.p. 136°–138° C.; NMR(delta CDCl$_3$): 0.8 (2d, 6H, 2CH$_3$), 1.2 (m, 3H, CH$_2$CH), 2.3 (s, 3H, NCH$_3$), 3.0 (m, 3H, PhCH$_2$, MeNCH), 4.7 (m, 1H, NCH of Phe). IR: 3300, 3350, 1675, 1625, 1540 cm$^{-1}$.

B. Proceeding in a similar manner, but replacing CBZ-N-methyl leucine and L-phenylalanine amide by other appropriately protected amino acid amides or esters, the following dipeptides were prepared:
N-methyl-leucyl-leucine amide, m.p. 141°–145° C.;
Leucyl-leucine amide m.p. 103°–106° C.;

N-methyl leucyl leucine methyl ester, m.p. 188°–189° C.;

Prolyl-leucinamide, m.p. 121°–125° C.

C. In like manner, the following peptide amides of Formula X are prepared:
L-propyl-L-phenylalanine amide;
valyl-beta-alanine amide; and
L-leucyl-glycinamide.

D. Similarly, but substituting an appropriate amino acid ester in place of the phenylalanine amide, the following compounds of Formula XIII are prepared:
leucyl-leucine methyl ester;
propyl-leucine ethyl ester;
glycyl-glycine methyl ester; and
valyl-3-amino butyric acid ethyl ester.

PREPARATION IX

A. Preparation of 1-N-(2-carbomethoxyphenyl)-carbamoyl-L-prolyl-L-leucylglycinamide and Related Compounds of Formula XI.

To a solution of 142 mg of L-prolyl-L-leucylglycinamide, in 2 ml dry tetrahydrofuran and 2 ml dry dimethylformamide was added a solution of 80 mg of 2-carbomethoxyphenyl isocyanate. The solution was stirred for 3 days whereupon the solvent was removed under reduced pressure. The residue was treated with 10 ml of hot ethyl acetate and filtered to give 150 mg of an insoluble residue characterized as 1-N-(2-carbomethoxyphenyl)-carbamoyl-L-prolyl-L-prolyl-L-leucyl-glycinamide: m.p. 196°–198° C., IR: 3280–3420 (broad), 1655, 1640, 1610, 1590 cm$^{-1}$; $^1$H NMR(delta DMSO-d$_6$); 0.85 (dd, 6H, [CH$_3$]$_2$CH); 1.4–1.7 (m, 3H, CHCH$_2$—CH[CH$_3$]$_2$); 1.78–2.09 (M, 4H, [Pro]CH$_2$—CH$_2$); 3,49–3.71 (m, 5H, [Pro]N—CH$_2$+[Leu]N—CH+[Gly]N—CH$_2$); 3.90 (s, 3H, COOMe); 4.1–4.43 (m, 1H, [Pro]N—CH); 6.89–7.25 (m, 2H Leu—NH, Gly NH); 7.4–8.55 (m, 4H, Ar—H); 10.38 (s, 1H, Ar—NH).

B. Similarly, but replacing the L-propyl-L-leucyl-glycinamide with other N-disubstituted amino acid, peptide amides or amino acid amides, the following compounds of Formula XI were prepared:
1-N-(2-carbomethoxyphenyl)-carbamoyl-L-prolinamide, m.p. 136°–138° C.;
1-N-(2-carbomethoxyphenyl)carbamoyl-L-prolyl-L-phenylalaninamide, m.p. 75°–78° C.;
1-N-(2-carbomethoxyphenyl)-carbamoyl-L-phenylalanine amide, m.p. 173°–174° C.;
1-N-(2-carbomethoxyphenyl)-carbamoyl-L-leucinamide, m.p. 145°–147° C.;
1-N-(2-carbomethoxyphenyl)-carbamoyl-L-prolyl-L-leucinamide, m.p. 157°–160° C.; and
1-N-(2-carbomethoxyphenyl)-carbamoyl-N-methyl-L-leucyl-L-leucinamide, m.p. 72°–75° C.

C. In like manner, the following compounds of Formula XI are prepared:
1-N-(2-carbomethoxy-3-methyl-phenyl)-carbamoyl-L-tyrosinamide;
1-N-(2-carbomethoxyphenyl)-carbamoyl-L-valine amide;
1-N-(2-carbomethoxy-6-methyl-phenyl)-carbamoyl-L-alanine amide;
1-N-(2-carbomethoxy-3-ethyl-phenyl)-carbamoyl-glycinamide;
1-N-(2-carbomethoxyphenyl)-carbamoyl-N-methyl-L-leucyl-L-prolyl-L-leucyl-glycinamide; and
1-N-(2-carbomethoxyphenyl)-carbamoyl-N-methyl-L-leucyl-L-alaninyl-L-prolyl-L-leucyl-glycinamide.

PREPARATION X

A. Preparation of 1-N-(2-Carboxyphenyl-carbamoyl-L-propyl-L-leucyl-glycinamide and Related Compounds of Formula XII.

1-N-(2-carbomethoxyphenyl)-carbamoyl-L-prolyl-L-leucyl-glycinamide (145 mg), prepared as described in Preparation IX above, was dissolved in 10 ml methanol. To this solution was added 0.33 ml of 1N sodium hydroxide, followed by stirring for 90 hours at room temperature. The methanol was evaporated and the residual solution was then partitioned between ethyl acetate and water. After acidification of the aqueous layer (pH 2) with 6M hydrochloric acid, a white precipitate was formed and isolated by filtration, to give 96 mg of 1-N-(2-carboxy-phenyl)-carbamoyl-L-prolyl-L-leucyl-glycinamide, m.p. 197°–198° C.; $^1$H NMR(delta DMSO-d$_6$); 0.88 (dd, 6H, [CH$_3$]$_2$); 1.35–1.71 (m, 3H, CH—CH$_2$—CH[CH$_3$]$_2$); 1.74–2.12 (M, 4H, [Pro]CH$_2$—CH$_2$); 3.43–3.75 (m, 5H, [Pro]N—CH$_2$+[Leu]N—CH+[Gly]—N—CH$_2$); 4.1–4.45 (m, 1H, [Pro]N—CH); 6.90–7.12 (m, 2H, [Leu]NH, [Gly]NH); 7,38–8.54 (m, 4H, ArH); 10.82 (s, 1H, CO$_2$H); IR: 1662, 1638 cm$^{-1}$.

B. Similarily, other 1-N-(2-carbomethoxyphenyl)-carbamoyl-amino acid or peptide amides prepared according to the method of Preparation IX, above, were converted to the following compounds of Formula XII:
1-N-(2-carboxyphenyl)-carbamoyl-L-prolinamide, m.p. 187°–188° C. (decomp);
1-N-(2-carboxyphenyl)-carbamoyl-L-prolyl-L-phenylalaninamide, m.p. 191°–192° C.;
1-N-(2-carboxyphenyl)-carbamoyl-L-prolyl-L-leucinamide, m.p. 126°–130° C.; and
1-N-(2-carboxyphenyl)-carbamoyl-N-methyl-L-leucyl-L-leucinamide, m.p. 108°–112° C.

C. In like manner, the following compounds of Formula XII are prepared:
1-N-(2-carboxy-3-methyl-phenyl)-carbamoyl-L-tyrosinamide;
1-N-(2-carboxyphenyl)-carbamoyl-L-valine amide;
1-N-(2-carboxy-6-methyl-phenyl)-carbamoyl-L-alanine amide;
1-N-(2-carboxy-3-ethyl-phenyl)-carbamoyl-glycinamide;
1-N-(2-carboxyphenyl)-carbamoyl-N-methyl-L-leucyl-L-propyl-L-leucyl-glycinamide;
1-N-(2-carboxyphenyl)-carbamoyl-N-methyl-L-leucyl-L-alaninyl-L-prolyl-L-leucyl-glycinamide.

PREPARATION XI

A. Preparation of D,L-leucine methyl ester isocyanate, and related compounds of Formula XIV.

5.03 gm of L-leucine methyl ester hydrochloride, and 2.8 gm of trichloromethyl chloroformate were added to 50 ml of dry p-dioxane. The mixture was heated at 60° C. for 8 hours and cooled. A clear solution was formed at this stage. The dioxane was removed under reduced pressure. The product isocyanate was isolated by vacuum distillation; yield 3:14 gm; bp. 88°–94° C. (1 mm Hg); $^1$H NMR; (delta CDCl$_3$); 0.9–1.0 (2d, 6H, 2CH$_3$), 1.5–1.8 (m, 3H, CHCH$_2$); 3.8 (s, 3H, OCH$_3$), 4.1 (t, 1H, CH—N=C=O). The IR spectrum of this material showed the following maxima: 2260, 1745 cm$^{-1}$.

B. Using the procedure above, but replacing leucine methyl ester hydrochloride with phenylalanine ethyl ester hydrochloride or valine ethyl ester hydrochloride, the following compounds of Formula XIV were obtained:
  phenylalanine ethyl ester isocyanate; and
  valine ethyl ester isocyanate.

PREPARATION XII

A. Synthesis of 1-N-(2-carbomethoxyphenyl)-carbamoyl-DL-leucine methyl ester and Related Compounds of Formula XV.

To a solution of 1.65 gm of methyl anthranilate in 100 ml toluene, was added 1.86 gm of the isocyanate of D,L-leucine methyl ester, prepared as described in Preparation XI above. The solution was refluxed for 24 hours. A small fraction of the reaction mixture was removed every 6 hours, evaporated to an oil, and monitored for residual isocyanate absorption at 2280 cm$^{-1}$.

After refluxing for 12 hours, an additional 0.85 ml of methyl anthranilate was added. Reflux was continued for another 12 hours after which the toluene was evaporated to an oil. The residue was dissolved in 100 ml of ethyl acetate and washed with 3N hydrochloric acid solution (200 ml). The ethyl acetate layer was dried over magnesium sulfate and then evaporated to an oil which was crystallized from ether and petroleum ether (30:60). Recrystallization yielded 1.02 gm of 1-N-(2-carbomethoxyphenyl)-carbamoyl-DL-leucine methyl ester, m.p. 86°-88° C. $^1$H NMR: (delta CDCl$_3$); 1.0 (d, 6H, 2CH$_3$), 1.6 (m, 3H [CH$_3$]$_2$CHCH$_2$); 3.8, 3.95 (2s, 6H, 2, OCH$_3$), 4.6 (m, 1H, N—CH), 5.1 (broad, 1H, CONHCH), 7.0, 7.5 (2m, 2H, ArH), 8.0, 8.5 (2dd, 2H, ArH), 10.5 (d, 1H, ArNH). The infrared absorption of the above material showed maxima at 3300, 1730, 1680, 1590 cm$^{-1}$.

B. In like manner, but substituting the isocyanate of phenylalanine ethyl ester, there was prepared:
  1-N-(2-carbomethoxyphenyl)-carbamoyl-phenylalanine ethyl ester, m.p. 104°-106° C; $^1$H NMR: (delta CDCl$_3$); 1.2 (t, 3H, CH$_3$), 3.2 (d, 2H, PhCH$_2$), 3.9 (s, 3H, OCH$_3$), 4.2 (q, 2H, OCH$_2$CH$_3$), 4.7 (m, 1H, NCHCO$_2$Et), 5.2 (broad d, 1H, CONHCH), 7.1, 7.5 (2m, 2H, ArH), 7.3 (m, 5H, PhCH$_2$), 8.0, 8.5 (2dd, 2H, ArH). The infrared spectrum exhibited the following characteristics 3310, 1740, 1605, 1665 cm$^{-1}$.

C. Proceeding in the same manner, but substituting other amino acid isocyanates, prepared according to the method of Preparation XI, the following compounds of Formula XV are prepared:
  1-N-(2-carbomethoxyphenyl)-carbamoyl glycine ethyl ester;
  1-N-(2-carbomethoxyphenyl)-carbamoyl alanine ethyl ester;
  1-N-(2-carbomethoxyphenyl)-carbamoyl arginine methyl ester;
  1-N-(2-carbomethoxyphenyl)-carbamoyl glutamic acid dimethyl ester;
  1-N-(2-carbomethoxyphenyl)-carbamoyl tyrosine methyl ester.

PREPARATION XIII

A. Preparation of 1-N-(2-Carbomethoxyphenyl)-Carbamoyl-L-Isoleucine Methyl Ester, and Related Compounds of Formula XV.

To a suspension of 0.74 gm of L-isoleucine methyl ester hydrochloride salt, in 25 ml of dry tetrahydrofuran, was added 0.58 ml of triethylamine. The suspension was stirred for 30 minutes at 0° to 5° C. A white precipitate was formed. A solution of 0.72 gm of 2-carbomethoxyphenyl isocyanate in 200 ml of dry tetrahydrofuran was then added. The solution was stirred at room temperature for 6 hours, whereupon TLC analysis (30% ethyl acetate in petroleum ether) indicated that the reaction was complete. Following evaporation of the solution under reduced pressure, the solid residue was partitioned between ethyl acetate (3×100 ml) and water (100 ml). The combined ethyl acetate extract was dried over magnesium sulfate and evaporated to a solid which recrystallized from ethyl acetate and petroleum ether to give 1-N-(2-carbomethoxyphenyl)-carbamoyl-L-isoleucine methyl ester, m.p. 72°-74° C. Yield: 720 mg; $^1$H NMR: (delta CDCl$_3$); 0.9 (d, overlapping peaks, 6H, 2CH$_3$); 1.1-1.5 (m, 3H, CH$_2$CH); 3.8, 3.95 (2s, 6H, 2CH$_3$); 4.5 (dd, 1H, CHCO$_2$CH$_3$); 5.2 (broad d, 1H, CoNHCH); 7.0, 7.5 (2m, 2H, ArH); 8.0, 8.5 (2dd, 2H, ArH); 10.4 (broad s, 1H, ArNHCO). The infrared absorption spectrum of the above material exhibited maxima 3340, 1725, 1690, 1590 cm$^{-1}$.

B. Proceeding in a similar manner, but replacing L-isoleucine methyl ester with other amino acid ester hydrochlorides, the following compounds of Formula XV were prepared:
  1-N-(2-carbomethoxyphenyl)-carbamoyl-L-valine methyl ester: m.p. 88°-90° C.; IR: 3340, 1725, 1690, 1590 cm$^{-1}$; $^1$H NMR: (delta CDCl$_3$): 1.0 (2d, 6H, 2CH$_3$); 2.2 (m, 1H, CH); 3.8-3.95 (2s, 6H, 2CH$_3$), 4.5 (dd, 1H, CHCO$_2$CH$_3$); 5.3 (broad d, 1H, CONHCH); 7.0, 7.5 1 (2m, 2H, ArH); 8.0, 8.5 (2dd, 2H, ArH); 10.5 (broad s, 1H, Ar—NHCO).
  1-N-(2-carbomethoxyphenyl)-carbamoyl-L-alanine ethyl ester: m.p. 115°-116° C.; IR: 3320, 1730, 1705, 1645 cm$^{-1}$; $^1$H NMR: (delta CDCl$_3$): 1.3 (d, 3H, OCH$_2$CH$_3$); 1.5 (d, 3H, CH$_3$); 4.25 (q, 2H, CO$_2$CH$_2$CH$_3$); 4.4 (q, 1H, CH$_3$CH); 5.3 (m, 1H, CONHCH); 7.0, 7.5 (2m, 2H, ArH); 8.0, 8.5 (2dd, 2H, ArH); 11.3 (m, 1H, Ar—NH).
  1-N-(2-carbomethoxyphenyl)-carbamoyl glycine ethyl ester: m.p. 119°-121° C.; IR: 3300, 1730, 1700, 1650 cm$^{-1}$; $^1$H NMR: (delta CHCl$_3$): 1.3 (t, 3H, CO$_2$CH$_2$CH$_3$); 3.9 (s, 3H, OCH$_3$); 4.1 (d, 2H, NCH$_2$CO$_2$Et); 4.25 (q, 2H, CO$_2$CH$_2$CH$_3$); 5.3 (m, 1H, CONHCH$_2$); 7.0, 7.5 (2m, 2H, ArH); 8.0, 8.5 (2dd, 2H, ArH); 10.5 (m, 1H, ArNH).
  Ethyl 1-N-(2-carbomethoxyphenyl)-carbamoyl-4-amino butyrate: m.p. 88°-90° C.; IR: 3300, 1720, 1700, 1650 cm$^{-1}$; $^1$H NMR: (delta CDCl$_3$): 1.3 (t, 3H, OCH$_2$CH$_3$); 1.9 (m, 2H, CH$_2$); 2.4 (t, 2H, CH$_2$CO$_2$Et); 3.4 (q, 2H, N—CH$_2$); 3.9 (s, 3H, OCH$_3$); 4.2 (q, 2H, OCH$_2$CH$_3$); 4.8 (m, 1H, CONH—CH$_2$); 7.0, 7.5 (2m, 2H, ArH); 8.0, 8.5 (2dd, 2H, ArH); 10.4 (broad s, 1H, ArNH).

C. Similarly, the following representative compounds of Formula XV are prepared:
  1N-(2-carbomethoxyphenyl)-carbamoyl beta-alanine methyl ester; and
  3-N-benzyl-5-N-(2-carbomethoxyphenyl)-hydantoic acid ethyl ester.

PREPARATION XIV

A. Preparation of L-Alanine p-toluene Sulfonic Acid Salt, and Related Compounds of Formula XVI.

L-alanine (3 gm) was added portionwise to a stirred solution of 9.6 gm of p-toluene sulfonic acid in dimethoxyethane during 20 min. at room temperature. The resulting mixture was stirred at room temperature for 30 min. and heated to 50° C. for 2 hours. Upon cooling, a precipitate was formed and was filtered to give 6 gm of L-alanine p-toluene-sulfonic acid salt, m.p. 192°–193° C. (recrystallization from methanol/DME); IR: 1750 cm$^{-1}$, 'HNMR (delta D$_2$O): 1.52 (d, 3H, CH$_3$); 2.35 (s, 3H, CH$_3$), 4.1 (m, 1H, CH), 7.5 (m, 4H, ArH).

B. In a similar manner, the p-toluene sulfonic acid salts of the following compounds are prepared:
Beta-alanine;
Valine;
Leucine;
Phenylalanine;
4-Amino butyric acid;
Glycyl-glycine; and
L-Leucyl-4-aminobutyric acid.

PREPARATION XV

A. Preparation of N-(2-carbomethoxyphenyl)-carbamoyl-4-amino butyric acid, and Related Compounds of Formula XVIII.

To a suspension of 1.24 gm of 4-aminobutyric acid p-toluene sulfonic acid salt, prepared according to the method of Preparation XIV above, in 25 ml dry methylene chloride was added 0.89 ml of hexamethyldisilazane. The solution was stirred for 1 hour. A solution of 0.748 gm of 2-carbomethoxyphenyl isocyanate in 10 ml dry methylene chloride was added to the above suspension and the resulting mixture was stirred for 5 hours. Evaporation of the solvent under reduced pressure followed by the addition of 100 ml of water and filtration gave a solid that was recrystallized from ethyl acetate, yielding 620 mg of N-(2-carbomethoxyphenyl)-carbamoyl-4-aminobutyric acid, m.p. 159°–160° C.

B. In like manner, but substituting other amino acid or peptidyl p-toluene sulfonic acid salts, prepared as described in Preparation XIV above, for the 4-aminobutyric acid p-toluene sulfonic acid salt, the following representative compounds of Formula XVIII are prepared:
N-(2-carbomethoxyphenyl)-carbamoyl-beta-alanine;
N-(2-carbomethoxyphenyl)-carbamoyl-valine;
N-(2-carbomethoxyphenyl-carbamoyl)-leucine;
N-(2-carbomethoxyphenyl-carbamoyl)-phenylalanine; and
N-(2-carbomethoxyphenyl-carbamoyl)-L-leucine-(4-aminobutyric acid).

PREPARATION XVI

A. Preparation of 3,5-dimethyl-(3-isopropylureido)-benzene and related Phenyl Ureas of Formula XIX.

To a solution of isopropylamine (5 ml) in dry tetrahydrofuran (25 ml) at 0° C., was added, dropwise, a solution of 3,5-dimethyl-phenyl isocyanate (6.4 ml) in 25 ml of dry tetrahydrofuran. The solution was stirred for 16 hours and evaporated to an oily solid. The solid was recrystallized from ethyl acetate, m.p. 207°–208° C.

B. Proceeding in a similar manner, but replacing the 3,5-dimethyl isocyanate with other appropriately substituted isocyanates, and the isopropylamine with other appropriate amines of Formula V, the following compounds were prepared:
3,5-dimethyl-(3-n-butylureido)-benzene, m.p. 137° C.;
2,3-dimethyl-(3-isopropylureido)-benzene, m.p. 195°–196° C.;
2,5-dimethyl-(3-isopropylureido)-benzene, m.p. 212°–213° C.;
2,4-dimethyl-(3-isopropylureido)-benzene, m.p. 187°–188° C.;
4-n-butyl-(3-isopropylureido)-benzene, m.p. 120°–122° C.; and
3-ethyl-(3-isopropylureido)-benzene, m.p. 118°–119° C.

C. Preparation of (3,5-dimethylphenyl-carbamoyl)-2-leucine methyl ester and related compounds of Formula XIX.

To a solution of L-leucine methyl ester hydrochloride (2 gm) in dry tetrahydrofuran, was added 1.54 ml of triethylamine. A white solid was formed and the mixture was stirred for ½ hour. A solution of 3,5-dimethylphenyl isocyanate (1.35 ml) in 10 ml tetrahydrofuran was added, dropwise, with cooling. The solution was stirred at room temperature for 16 hours and evaporated to a solid. The solid was partitioned with methylene chloride and water. The methylene chloride layer was dried over magnesium sulphate and evaporated to an oil which was recrystallized from methylene chloride and ether to give (3,5-dimethylphenyl-carbamoyl)-2-leucine methyl ester, m.p. 103°–106° C.

D. Proceeding as described in Section C., above but replacing the 3,5-dimethyl-phenyl isocyanate, where appropriate, with other appropriately substituted isocyanates of Formula XXXV, and replacing the L-leucine methyl ester hydrochloride of Formula XIII which other amino acid methyl ester salts of Formula XIII, the following compounds of Formula XIX are prepared:
(2,3-dimethylphenyl-carbamoyl)-L-Leucine methyl ester;
(2,5-dimethylphenyl-carbamoyl)-phenylalanine ethyl ester;
(3,5-dimethoxyphenyl-carbamoyl)-L-isoleucine methyl ester;
(3-methylphenyl-carbamoyl)-valine methyl ester;
(3-ethylphenyl-carbamoyl)-glycine ethyl ester;
(2,3-dimethoxy-carbamoyl)-alanine ethyl ester;
(2,5-dimethyl-carbamoyl)-phenylglycine methyl ester; and
(3,5-dimethyl-carbamoyl)-L-leucine methyl ester.

PREPARATION XVII

A. Preparation of Methyl 4-nitro-2-(3-isopropylureido)-benzoate and related compounds of Formula XXVI.

A solution of methyl-4-nitro-2-amino-benzoate (205 mg) in ethyl acetate (15 ml) was added to a solution of trichloromethyl chloroformate (103 mg) in 10 ml ethyl acetate. The solution was stirred for 1½ hours and quenched with 0.4 ml of isopropylamine. The reaction mixture was partitioned between ethyl acetate and 5% hydrochloric acid solution. The ethyl acetate layer was dried over magnesium sulphate and evaporated to a solid. The solid was freed from impurities by recrystallization from ether to give 4-nitro-2-isopropylureido-benzoate, 197°–198° C.

B. In like manner, but substituting other appropriate amines for the isopropylamine, the following compounds of Formula XXVI are prepared:
methyl 4-nitro-2-(3-n-butylureido)benzoate;
ethyl 4-nitro-2-(3-isopropylureido)-6-methylbenzoate; and
ethyl 4-nitro-2-(3-isopropylureido)-6-ethylbenzoate.

PREPARATION XVIII

A. Preparation of methyl-4-amino-2-(3-isopropylureido)-benzoate and related compounds of Formula XXVII To a solution of the methyl-4-nitro-2-isopropylureido-benzoate (98 mg), prepared as described in Preparation XVII-A, above, in ethanol under argon, was added a spatula tip of 10% palladium on charcoal. The solution was hydrogenated on a parr hydrogenator at 35 psi hydrogen for 4 hours, filtered through celite and evaporated to a solid. The solid was recrystallized from acetone/hexane to yield 4-amino-2-isopropylureido benzoate, m.p. 133°–135° C. Conversion to the corresponding 7-amino-2-isopropylamino-4H-3,1-benzoxazin-4-one was preformed as described in Example I-A and B, below.

B. In like manner, but starting instead with other appropriate compounds of Formula XXVI, prepared as described in Preparation XVII-B, above, the following compounds of Formula XXVII are prepared:
methyl 4-amino-2-(3-n-butylureido)benzoate;
ethyl 4-amino-6-methyl-2-(3-isopropylureido)benzoate; and
ethyl 4-amino-6-ethyl-2-(3-isopropylureido)benzoate.

PREPARATION XIX

A. Preparation of Methyl-4-acetylamino-2-(3-isopropylureido)-benzoate, and related compounds of Formula XXIX Methyl-4-amino-2-isopropylureido benzoate (15 mg) prepared as describe in Preparation XVIII, above, was added to a mixture of 3 ml acetic anhydride and 3 drops of pyridine. The solution was stirred for 2 days at room temperature. The solvent was removed under reduced pressure. The residue was partitioned between ethyl acetate, water and then 6M hydrochloric acid. The organic layer was dried and evaporated to an oily solid. The solid was recrystallized from ether to yield methyl-4-acetylamino-2(3-isopropylureido)-benzoate, m.p. 153°–155° C.

B. Similarly, but starting instead with other appropriate compounds of Formula XXVII, prepared as described in Preparation XVIII-B, or compounds of Formula 14, prepared as described in Preparation XXI, below and optionally substituting other alkyl anydrides, above, the following compounds of Formula XXIX are prepared:
methyl 4-acetylamino-2-(3-n-butylureido)benzoate;
methyl 4-butanamido-2-(3-isopropylureido)benzoate;
methyl 4-acetylamino-6-methyl-2-(3-isopropylureido)benzoate; and
methyl 4-acetylamino-6-ethyl-4-nitro-2-(3-isopropylureido)benzoate.

PREPARATION XX

A. Preparation of 4-Methyl-4-(3-isopropylureido)-2-(3-isopropylureido)-benzoate and related compounds of Formula XXXI A solution of methyl-4-amino-2-(3-isopropylureido)-benzoate (500 mg), prepared as described in Preparation XVIII, above, in ethyl acetate (10 ml) was added to a solution of trichloromethylchloroformate (0.157 gm) in 5 ml ethyl acetate. After 1½ hours, 5 ml of n-propylamine was added. The solution was diluted with ethyl acetate, extracted with water, 5% hydrochloric acid and washed with saturated sodium bicarbonate solution. The ethyl acetate layer was dried over magnesium sulphate and evaporated to yield methyl-4-(3-propylureido)-2-(3-isopropylureido)benzoate, as a solid, m.p. 94°–95° C.

B. Proceeding in a similar manner, the following compound was prepared:
methyl 2-(3-isopropylureido)-4-([pyrrolidinocarbamoyl]-amino)benzoate, m.p. 203.5–204.5° C.

C. In a similar manner, but replacing the methyl-4-amino-2-(3-isopropylureido)-benzoate with other appropriate compounds of Formula XXVII, prepared as described in Preparation XVIII, above the following compounds of Formula XXXI are prepared:
methyl 4-(3-n-butylureido)-2-(3-isopropylureido)benzoate;
methyl 4-(3-diethylureido)-2-(3-n-butylureido)benzoate;
methyl 4-(3-isopropylureido)-6-methyl-2-(3-isopropylureido)benzoate; and
methyl 4-(3-isopropylureido)-6-ethyl-2-(3-isopropylureido)-benzoate.

D. Similarly, but starting instead with appropriate compounds of Formula 14, prepared as described in Preparation XXI, below, the following compounds of Formula XXXI are prepared:
ethyl 4-(3-isopropylureido)-6-methyl-4-nitro-2-(3-isopropylureido)-benzoate; and
ethyl 4-(3-isopropylureido)-6-ethyl-4-nitro-2-(3-isopropylureido)-benzoate.

PREPARATION XXI

A. Preparation of Ethyl 2-amino-6-methyl-4-nitro benzoate and Related Compounds of Formula 14.

2-chloro-3,5-dinitro toluene was prepared according to the procedure described by B. Boothroyd and E. R. Clark, J. Chem. Soc., p. 1504, London (1953) from 2-hydroxy-3,5-dinitro toluene. The resulting chlorocompound was reacted with pentan-2,4-dione (10 fold excess) and sodium methoxide (3.5 fold excess) in HMPA at room temperature to give (2-methyl-4,6-dinitrophenyl)diacetylmethane, m.p. 145°–147° C. The product was isolated by conventional means and then cyclized with concentrated sulphuric acid over a period of 3 hours at 110° C., to give 4-methyl-6-nitro-anthranilic m.p. 158°–160° C. Subsequent refluxing with triethylamine and ethanol yielded ethyl 2-amino-6-methyl-4-nitro benzoate; IR: 3500, 3490, 1690 cm$^{-1}$.

B. In a similar manner, but starting with other appropriately substituted 1-alkyl-2-chloro-3,5-dinitrobenzenes, the following compounds of Formula 14 are prepared:
ethyl 2-amino-6-methyl-4-nitrobenzoate;
ethyl 2-amino-6-isopropyl-4-nitrobenzoate; and
ethyl 2-amino-6-n-butyl-4-nitro benzoate.

C. Compounds of Formula 14 are converted to compounds of Formula I, IC and ID according to the procedures of Preparations XIX and XX and Examples XI and XII.

EXAMPLE I

A. Synthesis of 2-sec-Butylamino-4H-3,1-Benzoxazin-4-One and Related Compounds of Formula IA.

Methyl 2-(3-sec-butyl-ureido)benzoate (90 mg) was dissolved in 2 ml of concentrated sulfuric acid. The solution was stirred for 2½ hours and poured onto ice. The ice-quenched mixture was rapidly neutralized with saturated sodium bicarbonate solution. The resulting white precipitate was filtered, dried and recrystallized from ether and petroleum ether, to yield 2-secbutylamino-4H-3,1-benzoxazin-4-one, m.p. 122°–123° C.; 'H NMR (delta CDCl$_3$): 1.0 (t, 3H, CH$_3$CH$_2$); 1.3 (d, 3H, CH$_3$CH); 1.6 (m, 2H, CH$_2$); 4.0 (m, 1H, CH—N); 7.2, 7.6 8.0 (3m, 4H, ArH). The infrared spectrum of this compound showed maxima at 3290, 1740, 1635 and 1600 cm$^{-1}$.

B. In like manner, but substituting for the methyl 2-(3-sec-butyl-ureido)benzoate other ureido benzoates prepared as described in Preparation IV and V above, the following compounds of Formula IA were prepared:

2-methylamino-4H-3,1-benzoxazin-4-one, m.p. 203°–204° C.;
2-ethylamino-4H-3,1-benzoxazin-4-one, m.p. 169°–170° C.;
2-propylamino-4H-3,1-benzoxazin-4-one; m.p. 170°–172° C.;
2-isopropylamino-4H-3,1-benzoxazin-4one; m.p. 151°–152° C.;
2n-butylamino-4H-3,1-benzoxazin-4one, m.p. 127°–129° C.;
2-hexylamino-4H-3,1-benzoxazin-4-one, m.p. 133°–135° C.;
2-octylamino-4H-3,1-benzoxazin-4-one, m.p. 117°–120° C.;
2-benzylamino-4H-3,1-benzoxazin-4-one, m.p. 177°–179° C.;
2-methylamino-5-methyl-4H-3,1-benzoxazin-4-one, m.p. 192°–193° C.;
2-isopropylamino-8-methyl-4H-3,1-benzoxazin-4-one, m.p. 185°–187° C.;
2-isopropylamino-5-methyl-4H-3,1-benzoxazin-4-one, m.p. 197°–199° C.;
2-n-butylamino-5-methoxy-4H-3,1-benzoxazin-4-one, m.p. 129°–131° C.;
2-n-butylamino-5-methyl-4H-3,1-benzoxazin-4-one, m.p. 130°–132° C.;
2-benzylamino-8-methyl-4H-3,1-benzoxazin-4-one, m.p. 164°–165° C.;
2-benzylamino-6,7-dimethoxy-4H-3,1-benzoxazin-4-one, m.p. 214°–215° C.;
2-benzylamino-7-ethyl-4H-3,1-benzoxazin-4-one, m.p. 139°–141° C.;
2-n-butylamino-7-ethyl-4H-3,1-benzoxazin-4-one, m.p. 121°–123° C.;
2-isopropylamino-7-ethyl-4H-3,1-benzoxazin-4one, m.p. 149°–150° C.;
2-isopropylamino-7-amino-4H-3,1-benoxazin-4-one, m.p. 144°–145° C.;
2-n-butylamino-8-methyl-4H-3,1-benzoxazin-4-one, m.p. 107°–109° C.; and
2-isopropylamino-5-methoxy-4H-3,1-benzoxazin-4-one, m.p. 131°–132° C.

C. In a similar manner, the following compounds of Formula IA are prepared:

2-(4-dimethylaminobenzylamino)-4H-3,1-benzoxaxin-4-one;
2-(2-phenylethylamino)-4H-3,2-benzoxazin-4-one;
2-(3-phenylpropylamino)-4H-3,1-benzoxazin-4-one;
2-(4-phenylbutylamino)-4H-3,1-benzoxazin-4-one;
2-(5-phenylpentylamino)-4H-3,1-benzoxazin-4-one;
2-(1-phenylethylamino)-4H-3,1-benzoxazin-4-one;
N-(2-[N-(4H-3,1-benzoxazin-4-on-2-yl)-amino]-ethyl)pyrrolidine;
N-(2-[N-(4H-3,1-benzoxazin-4-on-2-yl)-amino]-ethyl)morpholine;
2-[2-(3-indolyl)-ethyl]-amino-4H-3,1-benzoxazin-4-one;
2-[2-(5-benzyloxy-3-indolyl)-ethyl]-amino-4H-3,1-benzoxazin-4-one;
2-[2-(4-imidazolyl)-ethyl]-amino]-4H-3,1-benzoxazin-4-one;
2-([2-(2-pyridyl)-ethyl]-amino)-4H-3,1-benzoxazin-4-one;
2-([2-(3-pyridyl)-ethyl]-amino)-4H-3,1-benzoxazin-4-one;
N-(4H-3,1-benzoxazin-4-on-2-yl)-piperonylamine;
2-(2-methylbenzylamino)-4H-3,1-benzoxazin-4-one;
2-(4-methylbenzylamino)-4H-3,1-benzoxazin-4-one;
5-acetamido-2-benzylamino-4H-3,1-benzoxazin-4-one;
5-acetamido-2-isopropylamino-4H-3,1-benzoxazin-4-one;
5-acetamido-2-n-butylamino-4H-3,1-benzoxazin-4-one;
2-benzylamino-6-iodo-4H-3,1-benzoxazin-4-one;
2-isopropylamino-6-iodo-4H-3,1-benzoxazin-4-one;
2-n-butylamino-6-iodo-4H-3,1-benzoxazin-4-one;
2-benzylamino-6-n-butyl-4H-3,1-benzoxazin-4-one;
6-butyl-2-isopropylamino-4H-3,1-benzoxazin-4-one;
2-n-butylamino-6-n-butyl-4H-3,1-benzoxazin-4-one;
2-n-butylamino-7-chloro-4H-3,1-benzoxazin-4-one;
7-chloro-2-isopropylamino-4H-3,1-benzoxazin-4-one;
2-n-butylamino-6,8-di-iodo-4H-3,1-benzoxazin-4-one;
2-n-butylamino-7-ethyl-4H-3,1-benzoxazin-4-one;
2-isopropylamino-7-ethyl-4H-3,1-benzoxazin-4-one;
2-benzylamino-7-ethyl-4H-3,1-benzoxazin-4-one;
2-benzylamino-6-methyl-4H-3,1-benzoxazin-4-one;
2-n-butylamino-6-methyl-4H-3,1-benzoxazin-4-one;
2-isopropylamino-6-methyl-4H-3,1-benzoxazin-4-one;
2-n-butylamino-7-methyl-4H-3,1-benzoxazin-4-one;
2-isopropylamino-7-methyl-4H-3,1-benzoxazin-4-one;
2-benzylamino-7-methyl-4H-3,1-benzoxazin-4-one;
6-acetamido-2-n-butylamino-4H-3,1-benzoxazin-4-one;
6-acetamido-2-isopropylamino-4H-3,1-benzoxazin-4-one;
6-acetamido-2-benzylamino-4H-3,1-benzoxazin-4-one;
2-benzylamino-5,6-dimethyl-4H-3,1-benzoxazin-4-one;
2-benzylamino-5,7-dimethyl-4H-3,1-benzoxazin-4-one;
2-benzylamino-5,8-dimethyl-4H-3,1-benzoxazin-4-one;
2-benzylamino-6,7-dimethyl-4H-3,1-benzoxazin-4-one;
2-benzylamino-6,8-dimethyl-4H-3,1-benzoxazin-4-one;
2-benzylamino-7,8-dimethyl-4H-3,1-benzoxazin-4-one;
2-n-butylamino-5,6-dimethyl-4H-3,1-benzoxazin-4-one;
2-n-butylamino-5,7-dimethyl-4H-3,1-benzoxazin-4-one;
2n-butylamino-5,8-dimethyl-4H-3,1benzoxazin-4-one;
2-n-butylamino-6,7-dimethyl-4H-3,1-benzoxazin-4-one;
2-n-butylamino-6,8-dimethyl-4H-3,1-benzoxazin-4-one;
2-n-butylamino-7,8-dimethyl-4H-3,1-benzoxazin-4-one;
5,6-dimethyl-2-isopropylamino-4H-3,1-benzoxazin-4-one;

5,7-dimethyl-2-isopropylamino-4H-3,1-benzoxazin-4-one;
5,8-dimethyl-2-isopropylamino-4H-3,1-benzoxazin-4-one;
6,7-dimethyl-2-isopropylamino-4H-3,1-benzoxazin-4-one;
6,8-dimethyl-2-isopropylamino-4H-3,1-benzoxazin-4-one;
7,8-dimethyl-2-isopropylamino-4H-3,1-benzoxazin-4-one;
2-n-butylamino-5-ethyl-4H-3,1-benzoxazin-4-one;
2-ethylamino-6-chloro-4H-3,1-benzoxazin-4-one;
2-cyclohexylamino-5-fluoro-4H-3,1-benzoxazin-4-one;
2-hexylamino-8-nitro-4H-3,1-benzoxazin-4-one;
6,7-dimethoxy-2-n-propylamino-4H-3,1-benzoxazin-4-one;
2-sec-butylamino-5,8-dimethyl-4H-3,1-benzoxazin-4-one;
6-chloro-2-ethylamino-7-iodo-4H-3,1-benzoxazin-4-one;
2-pentylamino-6,7,8-trifluoro-4H-3,1-benzoxazin-4-one;
7-ethoxy-2-(2-propenylamino)-4H-3,1-benzoxazin-4-one;
6-bromo-5-ethyl-2-isopropylamino-8-methyl-4H,3,1-benzoxazin-4-one;
2-cyclopropylamino-8-dimethylamino-4H-3,1-benzoxazin-4-one;
2-n-butylamino-5,8-dimethyl-4H-3,1-benzoxazin-4-one;
2-ethylamino-6,7,8-trifluoro-4H-3,1-benzoxazin-4-one; and
5-ethyl-2-isopropylamino-3-methyl-4H-3,1-benzoxazin-4-one.

EXAMPLE II

Preparation of 2-n-Butylamino-5-Ethyl-4H-3,1-Benzoxazin-4-one and Related Compounds of Formula IA.

A standard solution of n-butylamine was prepared by adding 0.5 ml of n-butylamine to a 10 ml volumetric flask containing 10 ml dry methylene chloride. The n-butylamine solution (0.85 ml) was then added to 2-(1-benzotriazolyl)-5-ethyl-4H-3,1-benzoxazin-4-one (150 mg), prepared as described in Preparation VII above, in 21 mg of dry methylene chloride, and the mixture was stirred for 20 minutes. Analysis by TLC (20% ethyl acetate in toluene) indicated that the reaction was complete. The methylene chloride was then removed under reduced pressure and the remaining residue chromatographed over silica gel (10% ethyl acetate in toluene, flash column chromatography). All product fractions were combined and evaporated to give a solid that was recrystallized from pentane, yielding 40 mg of 2-n-butylamino-5-ethyl-4H-3,1-benzoxazin-4-one, m.p. 136°–137° C., IR: 330, 1725–1740 (broad), 1635, 1590, 1570 cm$^{-1}$); $^1$H NMR(delta CDCl$_3$): 1.0 (t, 3H, CH$_3$); 1.3 (t, 3H, CH$_3$); 1.5 (m, 4H, CH$_2$CH$_2$); 3.2 (q, 2H, PhCH$_2$); 3.4 (q, 2H, CH$_2$NH); 4.8 (broad, s, 1H, NH); 6.9–7.6 (m, 3H, ArH).

B. Proceeding in the same manner, but replacing n-butylamine with isopropylamine, the following compound of Formula IA was prepared:
5-ethyl-2-isopropylamino-4H-3,1-benzoxazin-4-one, m.p. 138°–139° C.; IR: 3300, 1725–1750, 1630, 1590, 1570 cm$^{-1}$); $^1$H NMR(delta CDCL$_3$): 1.1 (t, 3H, CH$_3$); 1.2 (d, 6H, 2CH$_3$); 3.2 (q, 2H, CH$_2$); 4.2 (m, 1H, NCH); 4.6 (m, 1H, NH), 6.9–7.6 (m, 3H, ArH).

C. In like manner, but replacing the 2-(1-benzotriazolyl)-5-ethyl-4H-3,1-benzoxazin-4-one with other appropriately substituted compounds of Formula VIII, prepared as described above in Preparation VII, and replacing the n-butylamine with other amines of Formula III, the following compounds of Formula IA are prepared:
2-octylamino-7-ethyl-4H-3,1-benzoxazin-4-one;
5-iodo-2-(2-penten-4-ynylamino)-4H-3,1-benzoxazin-4-one;
2-cyclopropylamino-5-methoxy-4H-3,1-benzoxazin-4-one;
2-allylamino-4H-3,1-benzoxazin-4-one;
2-propargylamino-4H-3,1-benzoxazin-4-one;
2-cyclopropylmethylamino-4H-3,1-benzoxazin-4-one; and
2-allylamino-6-n-butyl-4H-3,1-benzoxazin-4-one.

EXAMPLE III

A. Synthesis of 2-(N-Methylacetylamino)-5-Methyl-4H-3,1-Benzoxazin-4-one and Related Compounds of Formula IB-1.

To a solution of 200 mg 2-methylamino-5-methyl-4H-3,1-benzoxazin-4-one, prepared as described in Example I, above, in 20 ml of dry tetrahydrofuran, was added 3 ml of acetic anhydride, 3 ml of pyridine and 25 mg of dimethylaminopyridine. The solution was stirred at room temperature for 3 days. The solvent was removed under reduced pressure, and remaining trace amounts of acetic anhydride and pyridine were removed by azeotroping with toluene. The residue was purified by column chromatography over silica gel (10% ethyl acetate:petroleum ether, 30°–60° C.) to yield 210 mg of 2-(N-methylacetylamino)-5-methyl-4H-3,1-benzoxazin-4-one, m.p. 108°–109° C., $^1$H NMR: (delta CDCl$_3$); 2.6 (s, 3H, CH$_3$-Ar), 2.8 (s, 3H, CH$_3$), 3.4 (s, 3H, NMe), 7.1–7.8 (m, 3H, Ar-H); IR: 1765, 1690, 1640, 1620, 1600 cm$^{-1}$.

B. In like manner, but replacing the 2-(methylamino)-5-methyl-4H-3,1-benzoxazin-4-one with other 2-alkylamino-4H-3,1-benzoxazin-4-ones, the following compounds of Formula IB-1 were prepared:
2-(N-methylacetylamino)-8-methyl-4H-3,1-benzoxazin-4-one, m.p. 113°14 115° C., $^1$H NMR (delta CDCl$_3$): 2.4 (s, 3H, COCH$_3$), 2.7 (s, 3H, CH$_3$), 3.4 (s, 3H, N—CH$_3$), 7.3, 7.6, 8.0 (3m, 3H, ArH), IR: 1770, 1169, 1630, 1610 cm$^{31}$ $^1$.
2-(N-n-butylacetylamino)-8-methyl-4H-3,1-benzoxazin-4-one, m.p. 48°–49° C., $^1$H NMR (delta CDCl$_3$): 1.0 (t, 3H, CH$_3$), 1.2–1.8 (overlapping peaks, 4H, CH$_2$CH$_2$), 2.6 (s, 3H, COCH$_3$), 4.0 (t, 2H, NCH$_2$), 7.2, 7.8, 8.2 (3m, 3H, ArH). IR: 1770, 1690, 1630, 1600 cm$^{-1}$.

C. Similarly, the following compounds of Formula IB-1 are prepared:
6-chloro-2-(N-ethylacetylamino)-4H-3,1-benzoxain-4-one;
2-(N-benzylacetylamino)-4H-3,1-benzoxazin-4-one;
2-(N-methylacetylamino)-5-methyl-4H-3,1-benzoxazin-4-one;
2-(N-isopropylacetylamino)-8-methyl-4H-3,1-benzoxazin-4-one;
2-(N-isopropylacetylamino)-5-methyl-4H-3,1-benzoxazin-4-one;
2-(N-n-butylacetylamino)-5-methoxy-4H-3,1-benzoxazin-4-one;
2-(N-n-butylacetylamino)-5-methyl-4H-3,1-benzoxazin-4-one;

2-(N-allyl-acetamido)-4H-3,1-benzoxazin-4-one;
2-(N-propargyl-benzamido)-4H-3,1-benzoxazin-4-one;
2-(N-methyl-dodecanamido)-4H-3,1-benzoxazin-4-one; and
2-(N-cyclopropylmethyl-3-methylbutanamido)-4H-3,1-benzoxazin-4-one.

EXAMPLE IV

A. Synthesis of 2-(3-n-Butyl-1-methylureido)-4H-3,1-Benzoxazin-4-One and Related Compounds of Formula IB-2.

To a solution of 200 mg of 2-methylamino-4H-3,1-benzoxazin-4-one, prepared as described in Example II, above, in 50 ml dry toluene, was added 1 ml of n-butyl isocyanate. The solution was refluxed for 4 hours, and the solvent was then removed by evaporation under reduced pressure. Petroleum ether (30°-60° C.) was added. The resulting white precipitate was isolated by filtration to give the title compound of Formula IB-2. Additional amounts of the final product was isolated from the mother liquor by repeated recrystallization from ether: petroleum ether, (30°-60° C.). The 2-(3-n-butyl-1-methylureido)-4H-3,1-benzoxazin-4-one was characterized as follows: m.p. 74°-75° C., 'H NMR (delta acetone-$d_6$): 1.0 (m, 3H, $CH_3$), 1.6 (m, 4H, $CH_2CH_2$), 3.4 (m+s, 5H, $CH_2N+N$—Me), 7.4, 7.6, 7.8 (3m, 4H, Ar—H); IR: 3240, 1770, 1780, 1605 $cm^{-1}$.

B. In a similar manner, but replacing the 2-methylamino-4H-3,1-benzoxazin-4-one with other appropriate 2-alkylamino-4H-3,1-benzoxazin-4-ones prepared as described in Examples I and II, and replacing the n-butyl isocyanate with other corresponding isocyanates of Formula IX and Formula XIV prepared as described in Preparation III and Preparation XI above, the following compounds of Formula IB-2 and IB-3 were prepared:

2-(3-n-butyl-1-ethylureido)-4H-3,1-benzoxazin-4-one, m.p. 47°-50° C., 'H NMR (delta $CDCl_3$): 1.0 (t, 6H, $2CH_3$), 1.5 (m, 4H, $CH_2CH_2$), 3.4 (q, 2H, $CH_2N$), 4.0 (q, 2H, $CH_2N$), 7.2, 7.7, 8.2 (3m, 4H, ArH). IR: 3200, 1770, 1700, 1600 $cm^{-1}$.

5-N-(4H-3,1-benzoxazin-4-on-2-yl)-2-isobutyl-5-N-propylhydantoic acid methyl ester, m.p. 77°-80° C., 'H NMR (delta $CDCl_3$): 1.0 (d, 6H, $2CH_3$), 1.3 (t, 3H, $CH_3$), 1.8 (m, 4H, $CH_2CH_2$), 3.8 (s, 3H, $OCH_3$), 4.2 (q, 2H, $CH_2N$), 4.5 (q, 1H, CHN), 7.4, 7.8, 8.2 (3m, 3H, ArH). IR: 3180, 1750, 1730, 1710, 1620 $cm^{-1}$.

2-(3-isopropyl-1-propylureido)-4H-3,1-benzoxazin-4-one, m.p. 114°-115° C., 'H NMR (delta $CDCl_3$): 1.3 (overlapping peaks, 11H, $CH_3CH_2$, $[CH_3]_2C$), 3.8 (q, 3H, $NCH_2$, NCH), 7.4, 7.9 (2m, 4H, ArH). IR: 3200, 2960, 1770, 1690 $cm^{-1}$.

C. In a similar manner, the following compounds of Formula IB-2 are prepared:

2-(3-cyclohexyl-1-ethylureido)-4H-3,1-benzoxazin-4-one;
2-(3-n-butyl-1-n-butylureido)-4H-3,1-benzoxazin-4-one;
2-[3-(2-phenylethyl)-1-ethylureido]-4H-3,1-benzoxazin-4-one;
2-[3-(3-phenylpropyl)-1-cyclohexylureido]-4H-3,1-benzoxazin-4-one;
2-[3-(4-phenylbutyl)-1-hexylureido]-4H-3,1-benzoxazin-4-one;
2-(3-n-butyl-1-propylureido)-4H-3,1-benzoxazin-4-one;
2-(3-methyl-1-sec-butylureido)-4H-3,1-benzoxazin-4-one;
2-(3-ethyl-1-ethylureido)-4H-3,1-benzoxazin-4-one;
2-(3-n-propyl-1-pentylureido)-4H-3,1-benzoxazin-4-one;
2-(3-hexyl-1-cyclopropylureido)-5-methoxy-4H-3,1-benzoxazin-4-one; and
2-(1-allyl-3-isopropylureido)-6-n-butyl-4H-3,1-benzoxazin-4-one.

EXAMPLE V

A. Preparation of N-(4H-3,1-benzoxazin-4-on-2-yl)-L-prolyl-L-leucyl glycinamide and related compounds of Formula IC.

To a solution of 70 mg of 1-N-(2-carboxyphenyl)-carbamoyl-L-prolyl-L-leucyl glycinamide prepared as described in Preparation X above, in 200 ml of dry tetrahydrofuran was added 46 mg of 1-(3-dimethylaminopropyl)-3-ethyl-carbodiimide, followed by stirring for 46 hours at room temperature. After evaporation of the solvent under reduced pressure, the residue was partitioned between ethyl acetate and water. The ethyl acetate extract was dried over magnesium sulfate and then evaporated to a white solid that was recrystallized from ethyl acetate to yield 26 mg of N-(4H-3,1-benzoxazin-4-on-2-yl)-L-prolyl-L-leucyl-glycinamide, m.p. 199°-201° C.; 'H NMR (delta $CDCl_3$); 1.84 (d, 3H, $CH_3$); 1.91 (d, 3H, $CH_3$), 1.42-1.03 (m, 3H, CH—$CH_2$—$CH[CH_3]_2$); 1.8-2.50 (m, 4H, [Pro] $CH_2$—$CH_2$), 3.58-3.89 (m, 5H, [Pro]N—$CH_2$, [Leu]N—CH, [Gly]—N—$CH_2$); 4.25-4.51 (m, 1H, [Pro]N—CH); 6.27 (br, 2H, $CONH_2$; 6.8 (br, 1H, CONH); 7.01-8.03 (m, 4H, Ar—H); IR: 3320 $cm^{-1}$ (br), 1759 $cm^{-1}$.

B. Similarly, but replacing the 1-N-(2-carboxyphenyl)-carbamoyl-L-prolyl-L-leucyl-glycinamide with other amino acid amides and peptidyl amides prepared according to the method of Preparation X, above, the following compounds of Formula IC were prepared:

N-(4H-3,1-benzoxazin-4-on-2-yl)-L-prolinamide; m.p. 174°-176° C., 'H NMR (delta DMSO-$d_6$): 2.0 (m, 4H, $CH_2CH_2$), 3.6 (m, 2H, $CH_2$), 4.4 (m, 1H, CH), 7.2, 7.4, 7.8 (3m, 4H, ArH). IR: 3520, 3380, 3200, 1770, 1750, 1680, 1630 $cm^{-1}$.

N-(4H-3,1-benzoxazin-4-on-2-yl)-L-prolyl-L-phenylalaninamide; m.p. 226°-227° C., 'H NMR (delta DMSO-$d_6$): 1.8 (m, 4H, $CH_2CH_2$), 3.0 (m, 2H, $CH_2Ph$), 3.6 (m, 2H, $CH_2$), 4.4 (m, 2H, 2CH). IR: (max)=3200, 3280, 3200-3400(br), 1770, 1650, 1600 $cm^{-1}$.

N-(4H-3,1-benzoxazin-4-on-2-yl)-L-prolyl-L-leucinamide m.p. 205°-208° C.; NMR (delta $CDCl_3$): 0.78-0.92 (m, 6H, $2CH_3$), 1.21-1.88 (m, 3H, $CH_2CH[CH_3]_2$), 1.95-2.49 (m, 4H, $CH_2CH_2$), 3.64-3.90 (m, 2H, $NCH_2$), 4.33-4.71 (m, 2H, NCH, NCH), 7.08-8.2 (m, 4H, ArH), IR: 3400, 3281, 2950, 1768, 1651, 1621 $cm^{-1}$.

N-(4H-3,1-benzoxazin-4-on-2-yl)-N-methyl-L-leucyl-L-leucinamide m.p. 102°-105° C.; NMR (delta $CDCl_3$): 0.66-1.05 (m, 12H, $4 \times CH_3$), 1.15-1.92 (m, 6H, $2CH_2CH$), 3.08 (s, 3H, N—$CH_3$), 4.32-4.55 (t, 1H, NCH of Leu), 5.01-5.22 (t, 1H, NCH of Me—Leu), 7.08-8.2 (m, 4H, ArH), IR: 3260(br), 2950, 1765, 1670, 1596 $cm^{-1}$.

C. Similarly, but starting with other glycinamides prepared according to Preparation X, the following compounds are prepared:

N-(4H-3,1-benzoxazin-4-on-2-yl)-N-methyl-L-leucyl-L-prolyl-L-leucyl-glycinamide;

N-(4H-3,1-benzoxazin-4-on-2-yl)-N-methyl-L-leucyl-L-alaninyl-L-prolyl-L-leucyl-glycinamide.

EXAMPLE VI

A. Preparation of N-(4H-3,1-Benzoxazin-4-2-yl)-Phenylalaninamide and Related Compounds of Formula IC.

5 ml of concentrated sulfuric acid was added to 400 mg of 1-N-(2-carbomethoxyphenyl)-carbamoyl-phenylalanine amide (Preparation IX). The mixture was stirred for 3 hours and poured onto a mixture of ethyl acetate and ice-cold sodium bicarbonate solution. The mixture was extracted with ethyl acetate after neutralization. The organic extract, dried over magnesium sulfate, was evaporated to a solid. Recrystallization from ethyl acetate-hexane yielded 250 mg of N-(4H-3,1-benzoxazin-4-on-2-yl)-phenylalaninamide; m.p. 215°–216° C. $^1$H NMR 3.0 (m, 2H, PhCH$_2$), 4.5 (m, 1H, NCH), 7.8–8.2 (overlapping peaks, 9H, ArH). IR: 3380, 3180, 1750, 1730, 1660, 1640 cm$^{-1}$.

B. In like manner, other 1-N-2-(carbomethoxyphenyl)-carbamoyl amino acid or peptidyl amides prepared according to the methods described in Preparation IX, above, were converted to the following compounds of Formula IC:

N-(4H-3,1-benzoxazin-4-on-2-yl)-DL-prolinamide, m.p. 193°–194° C.; NMR (delta DMSO-d$_6$): 2.0 (m, 4H, CH$_2$CH$_2$), 3.6 (m, 2H, CH$_2$), 4.4 (m, 1H, CH), 7.2, 7.4, 7.8 (3m, 4H, PhH). IR 3400, 3200, 1775, 1761, 1750, 1680, 1630, 1630, 1600 cm$^{-1}$.

N-(4H-3,1-benzoxazin-4-on-2-yl)-leucinamide, m.p. 163°–165° C., NMR (delta DMSO-d$_6$), 0.9 (d, 6H, 2CH$_3$), 1.6 (m, 3H, CH$_2$CH), 4.2 (m, 1H, NCH), 7.2, 7.6, 7.8 (3m, 4H, PhH); IR: 3180–3420 (br), 1750, 1660, 1640, 1600 cm$^{-1}$.

C. Similarly, the following compounds of Formula IC are prepared:

N-(4H-3,1-benzoxazin-4-on-2-yl)-tyrosinamide;
N-(5-ethyl-4H-3,1-benzoxazin-4-one)-valine amide;
N-(8-methyl-4H-3,1-benzoxazin-4-on-2-yl)-alanine amide; and
N-(6-methyl-4H-3,1-benzoxazin-4-on-2-yl)-glycinamide.

EXAMPLE VII

Synthesis of N-(4H-3,1-benzoxazin-4-on-2-yl)-L-isoleucine methyl ester and Related Compounds of Formula ID.

120 mg of 1-N-(2-carbomethoxyphenyl)carbamoyl-L-isoleucine methyl ester, prepared as described in Preparation XIII above, was dissolved in 2 ml of concentrated sulfuric acid and stirred for 2 hours. The reaction mixture was poured into a beaker of ethyl acetate (200 ml) containing about 50 gm of ice. Saturated sodium bicarbonate solution was added rapidly to neutralize the excess acid. The mixture was poured into a separatory funnel and extracted with ethyl acetate. The organic extract was dried over magnesium sulfate, filtered and then evaporated to a solid which was recrystallized from ethyl acetate and petroleum ether (83 mg) to give the title compound: m.p. 86°–87° C.; $^1$H NMR(delta CDCl$_3$): 1.0 (d & t overlapping, 6H, 2CH$_3$); 1.5, 2.0 (2m, 3H, CH$_2$CH); 3.8 (s, 3H, OCH$_3$), 4.4 (m, 1H, CHCO$_2$CH$_3$); 5.4 (broad s, 1H, NH); 7.2, 7.6, 8.0 (3m 4H, ArH); IR: 3320, 1740, 1630, 1600 cm$^{-1}$.

B. In like manner, but substituting for 1-N-(2-carbomethoxyphenyl)-carbamoyl-L-isoleucine methyl ester, other 1-N-(2-carbomethoxyphenyl)-carbamoyl derivatives prepared according to the methods of Preparations XII and XIII, the following compounds of Formula ID were prepared:

N-(4H-3,1-benzoxazin-4-on-2-yl)-phenylalanine ethyl ester, as an oil, IR: 3340, 1740–1760, 1635, 1605 cm$^{-1}$; $^1$H NMR(delta CDCl$_3$): 1.3 (t, 3H, OCH$_2$CH$_3$); 3.2 (m, 2H, PhCH$_2$); 4.2 (q, 2H, OCH$_2$CH$_3$); 4.8 (t, 1H, NCH); 5.3 (broad s, 1H, NH); 7.2, 7.6, 8.0 (3m, 9H, ArH);

N-(4H-3,1-benzoxazin-4-on-2-yl)-alanine ethyl ester: m.p. 132°–134° C.; IR: 3340, 1760, 1720, 1630, 1600 cm$^{-1}$; $^1$H NMR(delta CDCL$_3$); 1.3 (t, 3H, CO$_2$CH$_2$CH$_3$); 1.55 (d, 3H, CH$_3$); 4.2 (q, 2H, CO$_2$CH$_2$CH$_3$): 4.6 (p, 1H, NCH); 5.4, (m, 1H, CONHCH); 7.2, 7.6, 8.1 (3m, 4H, ArH);

N-(4H-3,1-benzoxazin-4-on-2-yl)-glycine ethyl ester: m.p. 147°–148° C; IR: 3360, 1770, 1720, 1630, 1600 cm$^{-1}$; $^1$H NMR(delta CDCl$_3$): 1.3 (t, 3H, CO$_2$CH$_2$CH$_3$); 4.2 (d, 2H, CH$_2$); 4.25 (q, 2H, CO$_2$CH$_2$CH$_3$); 7.2, 7.6, 8.1 (3m, 4H, ArH);

Ethyl N-(4-H-3,1-benzoxazin-4-on-2-yl)-4-amino butyrate: m.p. 126°–127° C.; IR: 3320, 1760, 1700, 1630, 1600 cm$^{-1}$; $^1$H NMR(delta CDCl$_3$); 1.3 (t, 3H, CO$_2$CH$_2$CH$_3$); 2.0 (m, 2H, CH$_2$); 2.4 (m, 2H, CH$_2$CO$_2$Et); 3.4 (m, 2H, N—CH$_2$); 4.2 (q, 2H, OCH$_2$CH$_3$); 5.2, (m, 1H, NH); 7.2, 7.6 8.0 (3m, 4H, ArH);

N-(4H-3,1-benzoxazin-4-on-2-yl)-DL-leucine methyl ester; m.p. 90°–92° C.; IR: 3300, 1740, 1630, 1600 cm$^{-1}$; $^1$H NMR(delta CDCL$_3$); 1.0 (d, 6H, 2CH$_3$); 1.8 (m, 3H, CH$_2$CH); 3.8 (s, 3H, OCH$_3$); 4.4 (m, 1H, CHCO$_2$CH$_3$); 5.3 (m, 1H, NH); 7.2, 7.6, 8.1 (3m, 4H, ArH); and N-(4H-3,1-benzoxazin-4-on-2-yl)-valine methyl ester as an oil, IR: 3320, 1750, 1630, 1600 cm$^{-1}$; $^1$H NMR(delta CDCl$_3$): 1.0 (dd, 6H, 2CH$_3$); 2.1 (m, 1H, CH); 3.8, (s, 3H, CO$_2$Me); 4.5 (m, 1H, N—CH); 5.3 (broad s, 1H, NH); 7.2, 7.6, 8.0 (3m, 4H, ArH).

N-(4H-3,1-benzoxazin-4-on-2-yl)-D-phenylglycine methyl ester, m.p. 95° C.;

N-(4H-3,1-benzoxazin-4-on-2-yl)-DL-phenylglycine methyl ester, m.p. 100°–101° C.;

2-(3-carboxypropylamino)-4H-3,1-benzoxazin-4-one, m.p. 144°–146° C.; and

N-(4H-3,1-benzoxazin-4-on-2-yl)-D-leucine, methyl ester, m.p. 82°–83° C.

C. In like manner, but substituting for 1-N-(2-carbomethoxyphenyl)-carbamoyl-L-leucine methyl ester with other ureidobenzoates of Preparation XIII-C, the following compounds are obtained:

N-(4H-3,1-benzoxazin-4-on-2-yl)-N-benzyl glycine ethyl ester;

N-(4H-3,1-benzoxazin-4-on-2-yl)-beta-alanine ethyl ester;

N-(5-methyl-4H-3,1-benzoxazin-4-on-2-yl)-arginine methyl ester;

N-(5-methyl-4H-3,1-benzoxazin-4-on-2-yl)-glutamic acid diethyl ester; and

N-(8-methyl-4H-3,1-benzoxazin-4-on-2-yl)-tyrosine methyl ester.

EXAMPLE VIII

A. Preparation of N-(5-methyl-4H-3,1-benzoxazin-4-on-2-yl)-L-leucine methyl ester and Related Compounds of Formula ID.

To a solution of 130 mg of L-leucine methyl ester hydrochloride in 300 ml of dry methylene chloride, was added 0.1 ml of dry triethylamine. The mixture was stirred for 30 minutes whereupon a solution of 200 mg of 2-(1-benzotriazolyl)-5-methyl-4H-3,1-benzoxazin-4-one in 150 ml of dry methylene chloride was added. The reaction mixture was stirred at room temperature for 16 hours, concentrated and partitioned between ethyl acetate and water. The ethyl acetate layer was dried and evaporated to a solid that was purified by thick layer chromatography (Whatman 1000 micron plates) (20% ethyl acetate: toluene, $R_f$=0.8). Recrystallization from pentane gave 40 mg of N-(5-methyl-4H,3,1-benzoxazin-4-on-2-yl)-L-leucine methyl ester, (evaporation of the mother liquor gave 40 mg of crude product): m.p. 127°–128° C.; $^1$H NMR: (delta CDCl$_3$): 1.0 (d, 6H, 2CH$_3$); 1.7 (m, 3H, CH$_2$CH); 2.7 (s, 3H, Ar—CH$_3$); 3.8 (s, 3H, OCH$_3$); 4.7 (m, 1H, CHCO$_2$Me); 5.1 (m, 1H, NH); 6.9–7.6 (m, 3H, ArH); IR: 3300, 2960, 1750, 1730, 1640, 1595 cm$^{-1}$.

B. Proceeding in the same manner, but substituting for 2-(1-benzotriazolyl)-5-methyl-4H-3,1-benzoxazin-4-one other ring substituted 2-(1-benzotriazolyl)-4H-3,1-benzoxazin-4-ones, there were prepared:

N-(4H-3,1-benzoxazin-4-on-2-yl)-L-leucine methyl ester: m.p. 82°–83° C.; IR: 3300, 1760, 1740, 1630, 1600, 1570 cm$^{-1}$; $^1$H NMR: (delta CDCl$_3$): 1.0 (d, 6H, 2CH$_3$); 1.5 (m, 3H, CH$_2$CH); 3.8 (s, 3H, OCH$_3$); 4.7 (m, 1H, CHCO$_2$CH$_3$); 5.2 (d, 1H, NH); 7.2, 7.6, 8.0 (3m, 4H, ArH).

N-(5-ethyl-4H-3,1-benzoxazin-4-on-2-yl)-L-leucine methyl ester: m.p. 74°–75° C.; IR: 3280, 1730–1750, 1640, 1595, 1570 cm$^{-1}$; $^1$H NMR: (delta CDCl$_3$): 1.0 (d, 6H, 2CH$_3$); 1.25 (t, 3H, CH$_3$); 1.7 (m, 3H, CH$_2$CH); 3.2 (q, 2H, CH$_2$Ph); 3.8 (s, 3H, OCH$_3$); 4.7 (m, 1H, CHCO$_2$CH$_3$); 5.2 (d, 1H, NH); 7.2 (2m, 2H, ArH); 7.5 (dd, 1H, ArH).

C. Preparation of N-(4H-3,1-benzoxazin-4-on-2-yl)-N-methyl-L-leucyl-L-phenylalanine amide and related compounds of Formula IC.

To a solution of 220 mg of 2-(1-benzotriazolyl)-4H-3,1-benzoxazin-4-one in 50 ml dry methylene chloride, was added 245 mg of N-methyl-leucyl-phenylalanine amide. After 8 hours of stirring at room temperature, the solvent was evaporated and the residue purified by thick layer chromatography on silica gel plate (50% ethyl acetate-toluene). The spot at $R_f$=0.28 was isolated to give the title compound. Recrystallization was from ethyl acetate-pentane, yield 30 mg., m.p. 74°–76° C., $^1$H NMR (delta DMSO-d$_6$): 0.9 (t, 6H, 2CH$_3$), 1.6 (m, 3H, CH$_2$CH), 2.8 (s, 3H, N—CH$_3$), 3.0 (m, 2H, CH$_2$Ar), IR: 3200–3400 (br), 1740–1760 (br), 1660–1680 (br), 1590 cm$^{-1}$.

D. Proceeding in a similar manner, but replacing N-methyl-leucyl-phenylalanine amide by other dipeptides of Preparation VIII, the following compounds are prepared:

N-(4H-3,1-benzoxazin-4-on-2-yl)-L-leucyl-L-leucinamide; and

N-(4H-3,1-benzoxazin-4-on-2-yl)-N-methyl-L-leucyl-L-leucinamide.

EXAMPLE IX

A. Preparation of 2-(3-Carboxypropyl-amino)-4H-3,1-benzoxazin-4-one and Related Compounds of Formula ID.

350 mg of 1-N-(2-carbomethoxyphenyl)-carbamoyl-4-amino-butyric acid, prepared as described in Preparation XV above, was dissolved in concentrated sulfuric acid. The solution was stirred at room temperature for 2 hours. The reaction mixture was poured rapidly into 200 ml of ethyl acetate and 100 gm of ice in a 500 ml flask. The contents of the flask were rapidly swirled while saturated sodium bicarbonate solution was added to adjust the aqueous later to pH 4. The two layers were immediately separated and the aqueous layer was further extracted with 100 ml of ethyl acetate. The combined ethyl acetate extract was dried over magnesium sulfate and evaporated to a solid. This solid was recrystallized from ethyl acetate to yield 2-(3-carboxypropyl-amino)-4H-3,1-benzoxazin-4-one, m.p. 147°–148° C.

B. Proceeding in like manner, the following compounds are prepared:

2-(6-carboxyhexanyl-amino)-4H-3,1-benzoxazin-4-one;

2-(7-carboxy-2-methyl-ethylamino)-4H-3,1-benzoxazin-4-one; and

N-(4H-3,1-benzoxazin-4-on-2-yl)-L-leucyl-4-aminobutyric acid.

EXAMPLE X

Preparation of 4H-3,1-benzoxazin-4-ones of Formula XXI (IA or ID)

A. 5,7-dimethyl-2-isopropylamino-4H-3,1-benzoxazinone

To a solution of thallium trifluoroacetate (2.28 gm) in a 2 ml trifluoroacetic acid and 10 ml of dry tetrahydrofuran, was added a solution of 3,5-dimethyl-2-(3-isopropylureido)-benzene (0.99 gm) prepared according to Preparation XVI-A, above, in 10 ml of tetrahydrofuran. The solution was stirred in the dark for 16 hours and evaporated to dryness. The residual oil was azeotroped with 1,2-dichloroethane and evaporated to dryness. The residue was pumped dry for 1 hour to yield the corresponding compound of Formula XX.

To a suspension of lithium chloride (0.356 gm), palladium chloride (124 mg, 60% pure, Alfa Chemicals), and magnesium oxide (0.338 gm) in dry tetrahydrofuran (25 ml), was added a solution of the residue from above in tetrahydrofuran (20 ml). The flask and its content was flushed with carbon monoxide. The solution was stirred in the dark under 1 atmosphere of carbon monoxide for 16 hours. The reaction mixture filtered through celite, and evaporated to dryness. The residue was chromatographed on silica gel twice (20% ethyl acetate, petroleum ether, $R_f$=0.7). The product was recrystallized from ethyl acetate:hexane, m.p. 215°–218° C.

B. Proceeding in a similar manner, but replacing the 3,5-dimethyl-2-(3-isopropylureido)-benzene with other compounds of Formula XIX, prepared as described in Preparation XVI, A-C above, the following compounds of Formula XXI (IA or ID) were prepared:

[4H-3,1-benzoxazin-4-on-2-yl]-L-leucine methyl ester, m.p. 82°–84° C.;

2-n-butylamino-5,7-dimethyl-4H-3,1-benzoxazin-4-one, m.p. 144°–147° C.;

7,8-dimethyl-2-isopropylamino-4H-3,1-benzoxazin-4-one, m.p. 203°–206° C.;

5,8-dimethyl-2-isopropylamino-4H-3,1-benzoxazin-4-one, m.p. 206°–207° C.;

6,8-dimethyl-2-isopropylamino-4H-3,1-benzoxazin-4-one, m.p. 203°–206° C.;

5,7-dimethyl-2-isopropylamino-4H-3,1-benzoxazin-4-one, m.p. 215°–218° C.;

N-(5,7-dimethyl-4H-3,1-benzoxazin-4-on-2-yl)-L-leucine methyl ester, m,.p. 170°–172° C.; and 7-ethyl-2-isopropylamino-4H-3,1-benzoxazin-4-one, m.p. 149°–150° C.

C. Proceeding in a similar manner, but replacing the 3,5-dimethyl-(3-isopropylureido)-benzene with other appropriate compounds prepared as described in Preparation XVI-D, above, the following compounds of Formula XXI (ID) are prepared:

[7,8-dimethyl-4H-3,1-benzoxazin-4-on-2-yl]-L-leucine methyl ester;

[5,8-dimethyl-4H-3,1-benzoxazin-4-on-2-yl]-phenylalanine ethyl ester;

[5,7-dimethoxy-4H-3,1-benzoxazin-4-on-2-yl]-L-isoleucine methyl ester;

[7-methyl-4H-3,1-benzoxazin-4-on-2yl]-valine methyl ester;

[7-ethyl-4H-3,1-benzoxazin-4-on-2-yl]-glycine ethyl ester;

[7,8-dimethoxy-4H-3,1-benzoxazin-4-on-2-yl]-alanine ethyl ester; and

[5,7-dimethyl-4H-3,1-benzoxazin-4-on-2-yl]-L-leucyl-L-leucine methyl ester.

EXAMPLE XI

A. Preparation of 2-isopropylamino-7-(3-isopropylureido)-4H-3,1-benzoxazin-4-one and Related Compounds of Formula XXXII (IA, IC and ID)

A solution of methyl 4-(3-isopropylureido)-2-(3-isopropyl-ureido)-benzoate (150 mg) prepared as described in Preparation XX, above, in 5 ml concentrated sulphuric acid was stirred for 3 hours at room temperature. The solution was added, dropwise, to a rapidly stirred solution of ethyl acetate and saturated sodium bicarbonate solution (1:1, 60 ml ea.). The solution was extracted after neutralization. The ethyl acetate layer was dried over magnesium sulphate and evaporated to a solid. The solid was recrystallized from ethyl acetate:-hexane to yield 2-isopropylamino-7-(3-isopropylureido)-4H-3,1-benzoxin-4-one, m.p. 238°–240° C.

B. Proceeding in a similar manner, the following compound was prepared:

2-isopropylamino-7-(pyrrolidino-carbamoylamino)-4H-3,1-benzoxazin-4-one, m.p. 203.5°–204.5° C.

C. In a similar manner, but replacing the methyl-4-amino-2-(3-isopropylureido)-benzoate with other appropriate compounds of Formula XXXI or Formula 14, the following compounds of Formula XXXII are prepared:

7-(3-propylureido)-2-isopropylamino-4H-3,1-benzoxazin-4-one;

2-n-butylamino-7-(3-diethylureido)-4H-3,1-benzoxazin-4-one;

2-isopropylamino-7-(3-isopropylureido)-5-methyl-4H-3,1-benzoxazin-4-one; and 2-n-butylamino-5-ethyl-7-(3-isopropylureido)-4H-3,1-benzoxazin-4-one.

EXAMPLE XII

A. Preparation of 7-amino-2-isopropylamino-4H-3,1-benzoxazin-4-one, and related compounds of Formula XXVIII and XXX (IA, IC and ID).

A solution of methyl-4-amino-2-(3-isopropylureido)-benzoate (200 mg) prepared as described in Preparation XVIII, above, in 3 ml concentrated sulphuric acid was stirred at room temperature for 3 hours. The solution was added, dropwise, to a rapidly stirred solution of ethyl acetate and saturated sodium bicarbonate at 0° C. After neutralization, the solution was extracted. The ethyl acetate layer was dried over magnesium sulphate and evaporated to a solid. The solid was recrystallized from ether (m.p. 144°–145° C.).

B. Proceeding in the same manner, the following compound was prepared:

7-acetylamino-2-isopropylamino-4-H-3,1-benzoxazin-4-one, m.p. 137°–238° C.

C. In a similar manner, but starting with other appropriate compounds of Formula XXIX, prepared as described in Preparation XIX, above, the following compounds of Formula XXX are prepared:

7-benzamido-2-isopropylamino-4H-3,1-benzoxazin-4-one; and 7-butanamido-2-isopropylamino-4H-3,1-benzoxazin-4-one.

D. In a similar manner, but starting with other appropriate compounds of Formula XXVII and Formula 14, the following compounds are prepared:

7-amino-5-ethyl-2-isopropylamino-4H-3,1-benzoxazin-4-one;

7-amino-5-methyl-2-isopropylamino-4H-3,1-benzoxazin-4-one.

EXAMPLE XIII

Preparation of 2-alkylamino-5-alkyl-7-alkoxy-4H-3,1-benzoxazin-4-one

A. Zinc chloride (1 gm) was added to triethylamine (154 ml). The solution was stirred at room temperature for 30 minutes. A solution of 2,4-penta-2,4-dione (25 ml) in benzene (300 ml) was added, followed by chlorotrimethylsilane (186 ml). The solution was stirred at 40° C. overnight.

The solution was cooled, diluted with ether (2 liters) and filtered. The filtrate was evaporated in vacuo to give a brown residue. The residue was distilled at high vacuum to give (E) and (Z)-2,4-bis(trimethylsiloxy)-penta-1,3-diene (b.p. 72°–74° C., 1.5 mmHg.).

B. A solution of (E)- and (Z)-2,4-di(trimethylsiloxy)-penta-1,3-diene (622 gm) and diethyl acetylene dicarboxylate (6.5 gm) in toluene (20 ml) was refluxed for 16 hours. The solvent was removed by evaporation. The residual oil was diluted with 75 ml tetrahydrofuran and 75 ml 3% hydrochloric acid solution. The mixture was stirred for 3 days. The tetrahydrofuran was removed under reduced pressure. The aqueous residue was extracted with ethyl acetate. The ethyl acetate layer was dried over magnesium sulphate and evaporated to an oil. This oil was purified by column chromatography (silica gel, 20% ethyl acetate:petroleum ether). The spot corresponding to $R_f=0.29$ (20% ethyl acetate:petroleum ether) was determined to be diethyl 3-methyl-5-hydroxyphthalate.

C. Sodium hydride (380 mg. 50% oil) was added portionwise to a solution of diethyl 3-methyl-5-hydroxyphthalate (2 gm) in dry tetrahydrofuran (50 ml). The solution was stirred for 30 minutes. Methyl iodide (2 ml), tetra-n-butylammonium iodide (45 mg) and HMPA (5 ml) was added. The solution was stirred at room temperature for 2½ hours at refluxed at 60° C. for 1 hour. The solvent was removed under reduced pressure. The oil was partitioned between ethyl acetate and 5% hydrochloric acid solution. The ethyl acetate layer was washed with brine solution and dried over magnesium sulphate. Solvent evaporation gave an oil which was chromatographed (20% ethyl acetate:petroleum ether) to give diethyl 3-methyl-5-methoxy-phthalate.

IR: 2980, 1720, 1600 cm$^{-1}$.

By following this procedure but substituting ethyl iodide, n-propyl iodide or n-butyl iodide for methyl iodide, one obtains:
diethyl 3-methyl-5-ethoxy-phthalate,
diethyl 3-methyl-5-n-propoxy-phthalate, and
diethyl 3-methyl-5-n-butoxy-phthalate, respectively.

D. A solution of diethyl 3-methyl-5-methoxy phthalate (1 gm) in ethanol (10 ml) and sodium hydroxide (2%, 10 ml) was stirred for 3 hours at room temperature. Ethanol was removed by evaporation. The residue was acidified to pH=1 with 6M hydrochloric acid. The solution was extracted with ethyl acetate. The ethyl acetate layer was processed in the standard way to give 2-carboethoxy-3-methyl-5-methoxy-benzoic acid (380 mg), m.p. 142°–143° C.

By following this procedure but substituting the other phthalates prepared in Example XIII, Part C for 3-methyl-5-methoxy-phthalate, one obtains:
2-carboethoxy-3-methyl-5-ethoxy-benzoic acid,
2-carboethoxy-3-methyl-5-n-propoxy-benzoic acid, and
2-carboethoxy-3-methyl-5-n-butoxy-benzoic acid, respectively.

E. A solution of 2-carboethoxy-3-methyl-5-methoxybenzoic acid (60 mg) and 1,1-carbonyldiimidazole (40.8 mg) in tetrahydrofuran (8 ml) was stirred at room temperature for one half hour. Trimethylsilylazide (0.2 ml, Aldrich) was added and the solution was refluxed for 2 hours and left at room temperature for 40 minutes. The solvent was removed by evaporation. Toluene (5 ml, anhydrous) was added and the solution was refluxed for 16 hours. The solution was cooled to room temperature. Isopropylamine (1 ml) was added. The solution was stirred for 30 minutes and evaporated under reduced pressure to an oil. The residual oil was partitioned between ethyl acetate and 3% HCl. The ethyl acetate layer was washed with brine solution and dried over magnesium sulphate. Solvent evaporation gave an oil which was further purified by thick layer chromatography (20% ethyl acetate:petroleum ether), to give ethyl 2-(3-isopropylureido)-4-methoxy-6-methyl benzoate $R_f=0.3$, 44 mg, m.p. 148°–149° C.

By following this procedure but substituting the other benzoic acids prepared in Example XIII, Part D for 2-carboethoxy-3-methyl-5-methoxy-benzoic acid, one obtains:
ethyl-2-(3-isopropylureido)-6-methyl-4-ethoxybenzoate,
ethyl-2-(3-isopropylureido)-6-methyl-4-n-propoxybenzoate, and
ethyl-2-(3-isopropylureido)-4-n-butoxy-6-methyl benzoate, respectively.

F. A solution of ethyl 2-(3-isopropylureido)-4-methoxy-6-methyl benzoate (40 mg) in concentrated sulphuric acid (3 ml) was stirred for 3 hours at room temperature. The solution was then added dropwise to a mixture of saturated sodium bicarbonate solution and ethyl acetate at 0° C. After neutralization and extraction, the ethyl acetate layer was washed with brine solution, dried over magnesium sulphate and evaporated to a solid. The solid was further purified by thick layer chromatography (20% ethyl acetate:petroleum ether) to give 2-isopropylamino-5-methyl-7-methoxy-4H-3,1-benzoxaxin-4-one.
IR: 3430, 1740, 1600, 1630, 1560 cm$^{-1}$.

By following this procedure but substituting the other ethyl benzoates prepared in Example XIII, Part E for ethyl 2-(3-isopropylureido)-4-methoxy-6-methyl benzoate, one obtains:
2-isopropylamino-5-methyl-7-ethoxy-4H-3,1-benzoxazin-4-one;
2-isopropylamino-5-methyl-7-n-propoxy-4H-3,1-benzoxazin-4-one; and
2-isopropylamino-5-methyl-7-n-butyl-4H-3,1-benzoxazin-4-one, respectively.

EXAMPLE XIV

Conversion of Free Base to Acid Addition Salt

A twofold stoichiometric excess of 3% hydrogen chloride in dioxane is added to a solution of 1.0 g. of 2-isopropylamino-5-methyl-4H-3,1-benzoxazin-4-one in 20 ml dioxane. Diethyl ether is added until precipitation is complete. The product is filtered, washed with ether, air dried and recrystallized to give 2-isopropylamino-5-methyl-4H-3,1-benzoxazin-4-one hydrochloride.

In a similar manner, other compounds of Formula I in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE XV

Conversion of Salt to Free Base 1.0 g of 2-isopropylamino-5-methyl-4H-3,1-benzoxazin-4-one HCl suspended in 50 ml of ether is stirred with a twofold stoichiometric excess of dilute aqueous potassium carbonate solution until the salt is completely dissolved. The organic layer is then separated, washed twice with water, dried over magnesium sulfate and evaporated to yield 2-isopropylamino-5-methyl-4H-3,1-benzoxazin-4-one as the free base.

EXAMPLE XVI

Direct interchange of acid addition salts 2-n-butylamino-5-ethyl-4H-3,1-benzoxazin-4-one acetate (1.0 g) is dissolved in 50 ml water containing a stoichiometric equivalent of sulfuric acid, and the solution evaporated to dryness. The product is suspended in ether and filtered, air dried and recrystallized from methanol/acetone to yield 2-n-butylamino-5-ethyl-4H-3,1-benzoxazin-4-one sulfate.

In Examples XIII through XX, the active ingredient is N-(4H-3,1-benzoxazin-4-on-2-yl)-L-prolyl-L-leucyl-glycinamide. Other compounds of Formula I and the pharmaceutically acceptable salts thereof may be substituted therein.

EXAMPLE XVII

Preparation of 2-(3-carbomethoxy-propylamino)-4H-3,1-benzoxazin-4-one.

A solution of diazomethane in ether is added dropwise to a solution of 2-(3-carboxy-propylamino)-4H-3,1-benzoxazin-4-one in ether. The reaction is monitored by thin layer chromatography (silica gel, 10% ethylacetate in petroleum ether) until completion. A small amount of silica gel is added to the solution. The solution is allowed to stand for 3 hours, then filtered. The filtrate is evaporated to give 2-(3-carbomethoxypropylamino)-4H-3,1-benzoxazin-4-one.

In like manner, but substituting for the 2-(3-carboxypropylamino)-4H-3,1-benzoxazin-4-one other appropriate compounds of formula (I), esters of compounds of formula (I) are prepared.

EXAMPLE XVIII

Preparation of salts of compounds of Formula (I).

Triethylamine is added dropwise to a solution of 2-(3-carboxy-propylamino)-4H-3,1-benzoxazin-4-one in ethyl acetate. The reaction is monitored by thin layer chromatography (silica gel, 10% ethyl acetate in petroleum ether) until completion. The solution is evaporated under reduced pressure to give the triethylammonium salt of 2-(3-carboxy-propylamino)-4H-3,1-benzoxazin-4-one.

In a similar manner, other appropriate compounds of Formula I are prepared.

EXAMPLE XIX

Preparation of Free Compounds of Formula (I) from their Pharmaceutically Acceptable Esters.

2-(3-carbomethoxy-propylamino)-4H-3,1-benzoxazin-4-one is added to a solution of 1% sodium hydroxide. The solution is stirred for 3 hours at ambient temperature, then acidified to pH1 with 6N HCl. The solution is extracted with ethyl acetate, which is dried over magnesium sulfate, and dried to a solid.

The solid is added to concentrated sulfuric acid, stirred at ambient temperature for 3 hours, then poured into a rapidly stirring mixture of ethyl acetate and saturated aqueous sodium bicarbonate at 0° C. After extraction, the ethyl acetate phase is dried over magnesium sulfate and dried to give 2-(3-carboxypropylamino)-4H-3,1-benzoxazin-4-one.

In a similar manner, other appropriate compounds of formula (I) may be prepared from their pharmaceutically acceptable esters.

EXAMPLE XX

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE XXI

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE XXII

| Ingredients | Quantity per tablet, mgs. |
|---|---|
| Active ingredient | 200 |
| cornstarch | 50 |
| lactose | 145 |
| magnesium stearate | 5 |

The above ingredients are mixed intimately and pressed into single scored tablets.

EXAMPLE XXIII

| Ingredients | Quantity per tablet, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE XXIV

| Ingredients | Quantity per tablet, mgs. |
|---|---|
| Active ingredient | 150 |
| lactose | 92 |

The above ingredients are mixed and introduced into a hard-shell gelatin capsule.

EXAMPLE XXV

An injectable preparation buffered to a pH of 7 is prepared having the following composition:

| Ingredients | |
|---|---|
| Active ingredient | 0.2 g |
| KH$_2$PO$_4$ buffer (0.4 M solution) | 2 ml |
| KOH (1 N) | q.s. to pH 7 |
| water (distilled, sterile) | q.s. to 20 ml |

EXAMPLE XXVI

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE XXVII

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE XVIII

Human Leukocyte Elastase Inhibition Assay

1. Enzyme
    References: Barrett, A. J. (1981), *Methods in Enzymology*, 80C, 581–588. Engelbrecht, et al., (1982), Z. *Physiol. Chem.*, 363, 305–315.
    Fresh human leukocytes were obtained from a healthy donor, frozen and kept at −75° C. until use. Enzyme preparation followed the above referenced methods: cells were washed in saline, homogenized in the presence of 1M NaCl and 0.1% Brij 35 (Sigma Chemical C., No. P-1254). After centrifugation and concentration by dialysis against polyethylene glycol (MM 20,000), the material was chromatographed on Sephacryl S-300 (Pharmacia). Active fractions were combined, concentrated as before, and chromatographed on an affinity gel of bovine lung trypsin inhibitor attached to Sepharose CL-4B. Active fractions were combined, concentrated as before to approximately 0.3 micromolar in active elastase, and frozen in 1 ml aliquots at −75° C. until use.
2. Substrate
    Methoxysuccinyl-L-alanyl-L-alanyl-L-prolyl-L-valyl-N-m ethyl- coumarinamide was obtained from Peninsula Laboratories, San Carlos, Calif. Solutions of 1 mM in dimethylsulfoxide were made and kept at 4° C. until use.
3. Inhibitors
    The compounds of Formula I to be assayed were dissolved in dimethylsulfoxide to give 5, 10, or 20 mM stock solutions, which may be further diluted as required.
4. Assay Buffer
    The buffer consisted of 25 mM N-2-hydroxyethylpiperazine-N-2-ethane sulfonic acid, 1M sodium chloride, 0.1% w/v Brij 35, pH 7.8.
5. Procedure
    A Perkin-Elmer Model 650-40 fluorescence spectrophotometer is set up as follows: ratio mode, excitation 370 nm, emission 460 nm, full scale output 1, 5, or 10 units, cell compartment thermostatted at 25° C. For those compounds of Formula I which are themselves fluorescent, the excitation wavelength may be optionally 390 nm to minimize interference. To 2.0 ml of assay buffer in a fluorescence cuvette is added 5 microliters substrate and 20 microliters enzyme, with mixing. The change in fluorescence is recorded on a strip chart recorder to measure the initial, uninhibited rate, typically 0.8 units per minute. After approximately two minutes of such recording, inhibitor (between 0.5 and 20 microliters of the stock solution) is added with mixing, and recording continued. The reaction is recorded until a new constant rate is achieved. This procedure is repeated for several (4–6) inhibitor concentrations. The data—a table of substrate concentration, inhibitor concentration, and observed reaction velocities—are fit to the appropriate equation by non-linear least squares multiple regression.

EXAMPLE XXIX

Human Thrombin Inhibition Assay

1. Enzyme
    Human thrombin number T-885 was obtained from Sigma Chemical Company, St. Louis, Missouri, and reconstituted with water to approximately 2.5 NIH units/ml.
2. Substrate
    BOC-L-Valyl-L-propyl-L-arginyl-N-methyl-coumarinamide was obtained from Peninsula Laboratories, San Carlos, Calif. Solutions were made to 1 mM in dimethyl sulfoxide.
3. Inhibitors
    As Example XXI.
4. Assay Buffer
    The assay buffer consisted of 25 mM N-2-hydroxy ethylpiperazine-N-2-ethane sulfonic acid, 0.5M sodium chloride, 0.1% w/v polyethylene glycol 8000, pH 7.8.
5. Procedure
    The procedure was as in Example XXI, except that 5 microliters of substrate and 2.5 microliters enzyme solution were used.

EXAMPLE XXX

Human Urokinase Inhibition Assay

1. Enzyme
    Human Urokinase was obtained from Leo Laboratories, Pickering, Ontario, and made to approximately 2.5 mg/ml in 0.10M sodium citrate, 50 mM sodium chloride, pH 3.
2. Substrate
    Glutaryl-glycyl-L-arginyl-methyl coumarin amide (Peninsula Laboratories, vide supra) was made to approximately 1 mM in 1:1 water:dimethylsulfoxide.
3. Inhibitors
    As Example XXI.
4. Assay Buffer
    The assay buffer consisted of 50 mM tris(hydroxymethyl)amino methane, 0.10M sodium chloride, 10 mM calcium chloride, pH 8.0.
5. Procedure
    The procedure was as in Example XXI, with 5 microliters enzyme used.

EXAMPLE XXXI

Bovine Chymotrypsin Inhibition Assay

1. Enzyme
    Chymotrypsin type II was obtained from Sigma Chemical Company and made to 0.25 mg/ml in 1 mM hydrochloric acid and kept at 4° C. until use.
2. Substrate
    7-(Glutaryl-L-phenylalaninamido)-4-methyl coumarin was obtained from Sigma and made to 10 mM in 1:1 acetonitrile:dimethylsulfoxide.

3. Inhibitors

As Example XXI.

4. Assay Buffer

The assay buffer consisted of 25 mM N-2-hydroxy ethyl piperazine-N-2-ethane sulfonic acid, 0.1M potassium chloride, pH 7.8.

5. Procedure

As Example XXI.

EXAMPLE XXXII

Boar Acrosin Inhibition Assay

1. Enzyme

Boar acrosin was a gift of Professor W. Muller-Esterl, as purified in Muller-Esterl, et al., *Hoppe-Seyler's Z. Physiol. Chem.*, 361, 1811–1821, 1980, and was made to approximately 0.1 mg/ml in 1 mM HCl and kept at 4° C. until use.

2. Substrate 7-(N-benzoyl-L-argininamido)-4-methyl coumarin HCl was obtained from Sigma Chemical Company and made up to 2 mM in dimethyl sulfoxide.

3. Inhibitors

As Example XXI.

4. Assay Buffer

The assay buffer consisted of 0.10M N-2-hydroxy ethylpiperazine-N-2-ethane sulfonic acid, 50 mM calcium chloride, 0.01% v/v Triton X-100, pH 7.8.

5. Procedure

The procedure was as Example XXI, with 5 microliters substrate and 2.5 to 15 microliters enzyme as required to obtain approximately 0.5 fluorescent unit/minute uninhibited rate.

EXAMPLE XXXIII

Assay for Stability of Compounds in Whole Plasma

Whole, citrated human plasma was obtained from a local blook bank and kept frozen at −70° C. until use. Benzoxazinone (from a 10 mM stock solution in dimethylsulfoxide) was added to plasma at 37° C. to a final concentration of 50 mM, and incubation was continued at 37°. At various times thereafter, aliquots were withdrawn and diluted 5-fold into 20 mM potassium phosphate, 0.14 M sodium chloride, 3% w/v Brij 35 (Sigma Chemical Company), pH 7.4, and the fluorescence of this solution was monitored at 345 nm (excitation) and 429 nm (emission). The fluorescence intensity is proportional to the concentration of benzoaxazinone remaining. These data were fit by interative non-linear techniques to first-order exponentials to obtain the half-times in plasma.

Alternatively, for benzoxazininones which are weakly or non-fluorescent, high pressure liquid chromatography (HPLC) was used. From plasma incubations as above, aliquots were withdrawn and diluted 1:1 (v/v) with acetonitrile, mixed on a vortex stirrer, and centrifuged. Ten microliters of the supernatant was injected into the HPLC and chromatographed on a 5 micron RP-18 (reverse phase) column, in 9% acetonitrile, 10% water (v/v), with detection by absorbance at 340 nm. Retention times and concentrations were determined by comparison to standards. The integrated areas of the benzoxazinone peaks vs. incubation time were treated as above to obtain half-times.

What we claim is:

1. A compound of the formula:

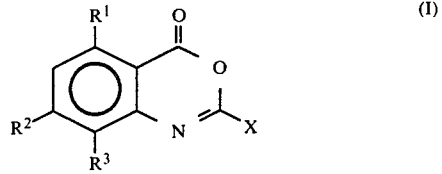

or a pharmaceutically acceptable ester or salt thereof, wherein:

$R^1$ is hydrogen or lower alkyl;

$R^2$ and $R^3$ are each independently hydrogen, lower alkyl, hydroxy, lower alkoxy, lower thioalkyl, $-NO_2$, $-N(R')_2$, $-NR'COR'$, $-NHCON(R')_2$ or NHCOOR', with the proviso that at least one of $R^1$, $R^2$ and $R^3$ is not hydrogen when X is NHR or NR'COR''; and X is a radical chosen from the group consisting of:

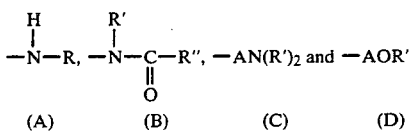

in which:

R is ethyl, n-propyl, isopropyl, n-butyl, isobutyl, tert-butyl, sec-butyl, pentyl, hexyl, octyl, lower alkenyl, lower alknyl, a saturated hydrocarbon ring of 3 to 6 carbon atoms, either unsubstituted, or substituted with 1 to 5 substituents selected independently from the group consisting of lower alkyl, lower alkenyl, lower alkoxy, amino, halo, nitro, lower alkyl amino, or lower dialkylamino; or a phenyl ring attached to an alkyl chain of one to six carbon atoms, wherein the phenyl ring is either unsubstituted, or substituted with one to three substituents selected independently from the group consisting of lower akyl, lower alkenyl, lower alkoxy, amino, halo, nitro, lower alkyl amino, or lower dialkylamino;

each R' is independently hydrogen or lower alkyl, or lower alkenyl or lower alkynyl where the unsaturated bond is at least one carbon removed from the O or N atom;

each R'' is independently R, lower alkoxy, NHR' or AOR'; and

A is an amino acid residue, or a peptide of 2 to 3 amino acid residues.

2. A compound of claim 1, or a pharmaceutically acceptable salt thereof, in which at least one of $R^1$, $R^2$ and $R^3$ is not hydrogen.

3. The compound of claim 2 wherein X is NHR, $R^1$ is lower alkyl and R is ethyl, n-propyl, isopropyl, n-butyl, isobutyl, tert-butyl or sec-butyl.

4. A compound of claim 2, or a pharmaceutically acceptable salt or ester thereof, in which $R^2$ is not hydrogen.

5. A compound of claim 2, or a pharmaceutically acceptable salt or ester thereof, in which $R^2$ is lower alkyl, lower alkoxy, hydroxy, lower thioalkyl, or $-N(R')_2$.

6. A compound of claim 1 or a pharmaceutically acceptable salt or ester thereof, in which $R^1$ is lower alkyl and $R^2$ is lower alkyl, lower alkoxy, hydroxy, lower thioalkyl or $-N(R')_2$.

7. A compound of claim 1, or a pharmaceutically acceptable salt thereof, in which X is —NHR.

8. The compound of claim 7 in which R is -isopropyl, R¹ is methyl, and R² and R³ are each hydrogen, namely 2-isopropylamino-5-methyl-4H-3,1-benzoxazin-4-one, or a pharmaceutically acceptable salt thereof.

9. The compound of claim 7 in which R is -isopropyl, R¹ is ethyl, and R² and R³ are each hydrogen, namely 2-isopropylamino-5-ethyl-4H-3,1-benzoxazin-4-one, or a pharmaceutically acceptable salt thereof.

10. The compound of claim 7 in which R is -n-butyl, R¹ is methyl, and R² and R³ are each hydrogen, namely 2-n-butylamino-5-methyl-4H-3,1-benzoxazin-4-one, or a pharmaceutically acceptable salt thereof.

11. The compound of claim 7 in which R is -n-butyl, R¹ is ethyl, and R² and R³ are each hydrogen, namely 2-n-butylamino-5-ethyl-4H-3,1-benzoxazin-4-one, or a pharmaceutically acceptable salt thereof.

12. The compound of claim 7 in which R is -isopropyl, R² is -ethyl, and R¹ and R³ are each hydrogen, namely 7-ethyl-2-isopropylamino-4H-3,1-benzoxazin-4-one, or a pharmaceutically acceptable salt thereof.

13. A compound of claim 7 in which R is isopropyl, R² is -amino, and R¹ and R³ are each hydrogen, namely 7-amino-2-isopropylamino-4H-3,1-benzoxazin-4-one, or a pharmaceutically acceptable salt thereof.

14. A compound of claim 7 in which R is -isopropyl, R² and R³ are methyl, and R¹ is hydrogen, namely 7,8-dimethyl-2-isopropylamino-4H-3,1-benzoxazin-4-one, or a pharmaceutically acceptable salt thereof.

15. A compound of claim 7 in which R is -isopropyl, R¹ and R² are methyl, and R³ is hydrogen, namely 5,7-dimethyl-2-isopropylamino-4H-3,1-benzoxazin-4-one, or a pharmaceutically acceptable salt thereof.

16. A compound of claim 1, or a pharmaceutically acceptable ester or salt thereof, in which X is —AOR'.

17. The compound of claim 16 in which R¹ is ethyl, R² and R³ are each hydrogen, A is -L-leucine and R' is -methyl, namely N-(5-ethyl-4H-3,1-benzoxazin-4-on-2-yl)-L-leucine methyl ester, or a pharmaceutically acceptable salt thereof.

18. A compound of claim 16 in which R¹ is methyl, R² and R³ are each hydrogen, A is -L-leucine and R' is methyl, namely N-(5-methyl-4H-3,1-benzoxazin-4-on-2-yl)-L-leucine methyl ester, or a pharmaceutically acceptable salt thereof.

19. A compound of claim 16 in which R¹ and R² are each methyl, R³ is hydrogen, A is L-leucine, and R' is methyl, namely N-(5,7-dimethyl-4H-3,1-benzoxazin-4-on-2-yl)-L-leucine methyl ester, or a pharmaceutically acceptable salt thereof.

20. A compound of claim 1, or a pharmaceutically acceptable ester or salt thereof, in which X is —AN(R')₂.

21. A compound of claim 1, or a pharmaceutically acceptable salt thereof, in which X is —NR'COR".

22. A compound of claim 21, or a pharmaceutically acceptable salt or ester thereof, in which R is chosen from the group consisting of lower alkyl and a saturated hydrocarbon ring of 3 to 6 carbon atoms, either unsubstituted, or substituted with 1 to 5 substituents selected independently from the group consisting of lower alkyl, lower alkenyl, lower alkoxy, amino, halo, nitro, lower alkyl amino, or lower dialkylamino.

23. A compound of the formula:

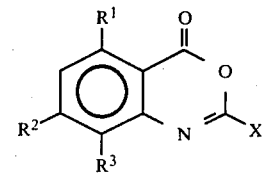

or a pharmaceutically acceptable ester or salt thereof, wherein:

R¹ is hydrogen or lower alkyl;

R² and R³ are each independently hydrogen, halo, lower alkyl, hydroxy, lower alkoxy, lower thioalkyl, —NO₂, —N(R')₂, —NR'COR', —NHCON(R')₂ or —NHCOOR', with the proviso that at least one of R¹, R² and R³ is not hydrogen when X is NHR or NR'COR";

X is a radical chosen from the group consisting of:

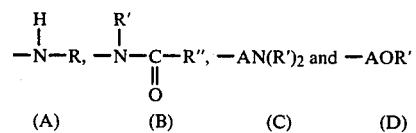

in which:

R is lower alkenyl, lower alkynyl, a saturated hydrocarbon ring of 3 to 6 carbon atoms, either unsubstituted, or substituted with 1 to 5 substituents selected independently from the group consisting of lower alkyl, lower alkenyl, lower alkoxy, amino, halo, nitro, lower alkyl amino, or lower dialkylamino; or a phenyl ring attached to an alkyl chain of one to six carbon atoms, wherein the phenyl ring is either unsubstituted, or substituted with one to three substituents selected independently from the group consisting of lower alkyl, lower alkenyl, lower alkoxy, amino, halo, nitro, lower akyl amino, or lower dialkylamino;

each R' is independently hydrogen or lower alkyl, or lower alkenyl or lower alkynyl where the unsaturated bond is at least one carbon removed from the O or N atom;

each R" is independently R, lower alkoxy, NHR' or AOR'; and

A is an amino acid residue, or a peptide of 2 to 3 amino acid residues.

24. A compound of the formula:

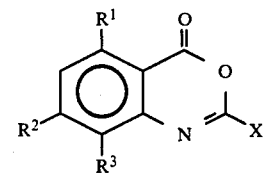

or a pharmaceutically acceptable ester or salt thereof, wherein:

R¹ is lower alkyl;

R² and R³ are each independently hydrogen, halo, lower alkyl, hydroxy, lower alkoxy, lower thioalkyl, —NO₂, —N(R')₂, —NR'COR', —NHCON(R')₂ or —NHCOOR'; and X is a radical chosen from the group consisting of:

$$-\underset{(A)}{\overset{H}{N}-R,} \quad -\underset{(B)}{\overset{R'}{N}-\underset{\underset{O}{\|}}{C}-R''}, \quad -\underset{(C)}{AN(R')_2} \text{ and } -\underset{(D)}{AOR'}$$

in which:
  R is ethyl, n-propyl, isopropyl, n-butyl, isobutyl, tert-butyl, sec-butyl, lower alkenyl, lower alkynyl, a saturated hydrocarbon ring of 3 to 6 carbon atoms, either unsubstituted, or substituted with 1 to 5 substituents selected independently from the group consisting of lower alkyl, lower alkenyl, lower alkoxy, amino, halo, nitro, lower alkyl amino, or lower dialkylamino; or a phenyl ring attached to an alkyl chain of one to six carbon atoms, wherein the phenyl ring is either unsubstituted, or substituted with one to three substituents selected independently from the group consisting of lower alkyl, lower alkenyl, lower alkoxy, amino, halo, nitro, lower alkyl amino, or lower dialkylamino;
  each R' is independently hydrogen or lower alkyl, or lower alkenyl or lower alkynyl where the unsaturated bond is at least one carbon removed from the O or N atom;
  each R'' is independently R, lower alkoxy, NHR' or AOR'; and
  A is an amino acid residue, or a peptide of 2 to 3 amino acid residues.

25. The compound of claim 24 wherein R³ is hydrogen, and R¹ and R² are not hydrogen.

26. The compound of claim 25 wherein X is NHR and R is ethyl, n-propyl, isopropyl, n-butyl, isobutyl, tert-butyl, or sec-butyl.

27. A compound of the formula:

(I)

or a pharmaceutically acceptable ester or salt thereof, wherein:
  R¹ is lower alkyl;
  R² and R³ are each independently hydrogen, halo, lower alkyl, hydroxy, lower alkoxy, lower thioalkyl, —NO₂, —N(R')₂, —NR'COR', —NHCON(R')₂ or —NHCOOR';
  X is NHR in which R is ethyl, n-propyl, isopropyl, n-butyl, isobutyl, tert-butyl, sec-butyl; and
  each R' is independently hydrogen or lower alkyl, or lower alkenyl or lower alkynyl where the unsaturated bond is at least one carbon removed from the O or N atom.

28. A compound of the formula:

(I)

or a pharmaceutically acceptable ester or salt thereof, wherein:
  R¹ is lower alkyl;
  R² is halo, lower alkyl, hydroxy, lower alkoxy, lower thioalkyl, —NO₂, —N(R')₂, —NR'COR', —NHCON(R')₂ or —NHCOOR';
  R³ is hydrogen;
  X is a radical chosen from the group consisting of:

$$-\underset{(A)}{\overset{H}{N}-R,} \quad -\underset{(B)}{\overset{R'}{N}-\underset{\underset{O}{\|}}{C}-R''}, \quad -\underset{(C)}{AN(R')_2} \text{ and } -\underset{(D)}{AOR'}$$

in which:
  R is ethyl, n-propyl, isopropyl, n-butyl, isobutyl, tert-butyl, sec-butyl, lower alkenyl, lower alkynyl, optionally substituted lower cycloalkyl, optionally substituted phenyl lower alkyl;
  each R' is independently hydrogen or lower alkyl, or lower alkenyl or lower alkynyl where the unsaturated bond is at least one carbon removed from the O or N atom;
  each R'' is independently R, lower alkoxy, NHR' or AOR'; and
  A is an amino acid residue, or a peptide of 2 to 3 amino acid residues.

29. A compound of the formula:

(I)

or a pharmaceutically acceptable ester or salt thereof, wherein:
  R¹ is hydrogen or lower alkyl;
  R² is hydrogen, lower alkyl, hydroxy, lower alkoxy, lower thioalkyl, —NO₂, —N(R')₂, —NR'COR', —NHCON(R')₂ or —NHCOOR',
  with the proviso that at least one of R¹ and R² is not hydrogen;
  R³ is hydrogen; and
  X is a radical chosen from the group consisting of:

$$-\underset{(A)}{\overset{H}{N}-R,} \quad -\underset{(B)}{\overset{R'}{N}-\underset{\underset{O}{\|}}{C}-R''}, \quad -\underset{(C)}{AN(R')_2} \text{ and } -\underset{(D)}{AOR'}$$

in which:
  R is ethyl, n-propyl, isopropyl, n-butyl, isobutyl, tert-butyl, sec-butyl, lower alkenyl, lower alkynyl, a saturated hydrocarbon ring of 3 to 6 carbon atoms, either unsubstituted, or substituted with 1 to 5 substituents selected independently from the group consisting of lower alkyl, lower alkenyl, lower alkoxy, amino, halo, nitro, lower alkyl amino, or lower dialkylamino; or a phenyl ring attached to an alkyl chain of one to six carbon atoms, wherein the phenyl ring is either unsubstituted, or substituted with one to three substituents selected independently from the group consisting of lower alkyl, lower alkenyl, lower alkoxy, amino, halo, nitro, lower alkyl amino, or lower dialkylamino;

each $R^1$ is independently hydrogen or lower alkyl, or lower alkenyl or lower alkynyl where the unsaturated bond is at least one carbon removed from the O or N atom;

each R" is independently R, lower alkoxy, NHR' or AOR'; and

A is an amino acid residue, or a peptide of 2 to 3 amino acid residues.

30. The compound of claim 28, or a pharmaceutically acceptable ester or salt thereof, in which X is NHR and R is ethyl, isopropyl or n-butyl.

31. The compound of claim 30, or a pharmaceutically acceptable ester or salt thereof, in which $R^1$ is methyl or ethyl.

32. The compound of claim 31, or a pharmaceutically acceptable ester or salt thereof, in which $R^2$ is $NH_2$, lower alkyl, or lower alkoxy.

33. The compound of claim 32, or a pharmaceutically acceptable ester or salt thereof, in which R is isopropyl or n-butyl; $R^1$ is methyl or ethyl; and $R^2$ is $NH_2$, methyl, or methoxy.

34. The compound of claim 33, or a pharmaceutically acceptable ester or salt thereof, in which R is isopropyl; $R^1$ is ethyl; and $R^2$ is $NH_2$.

35. A pharmaceutical composition for inhibiting serine proteases in animals which comprises a therapeutically effective amount of a compound of claim 1 or a pharmaceutically acceptable non-toxic ester or salt thereof in admixture with a pharmaceutically acceptable excipient.

36. A method of inhibiting serine proteases in animals which method comprises administering to a subject in need of such treatment a therapeutically effective amount of, or a pharmaceutically composition containing a therapeutically effective amount of, the compound of claim 1 or a pharmaceutically acceptable acid addition salt thereof.

37. The method of claim 36 in which the serine protease is human leukocyte elastase.

38. The method of claim 36 in which the serine protease is trypsin.

39. A method for treating inflammation comprising the step of administering a therapeutically effective amount of a compound of the formula:

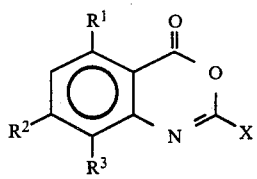

(I)

or a pharmaceutically acceptable ester or salt thereof, wherein:

$R^1$ is hydrogen or lower alkyl;

$R^2$ and $R^3$ are each independently hydrogen, halo, lower alkyl, hydroxy, lower alkoxy, lower thioalkyl, $-NO_2$, $-N(R')_2$, $-NR'COR'$, $-NHCON(R')_2$ or $-NHCOOR'$, with the proviso that at least one of $R^1$, $R^2$ and $R^3$ is not hydrogen when X is NHR or NR'COR"; and X is a radical chosen from the group consisting of:

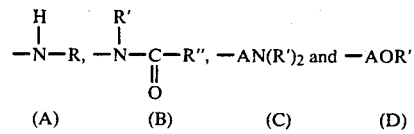

in which:

R is lower alkyl, lower alkenyl, lower alkynyl, a saturated hydrocarbon ring of 3 to 6 carbon atoms, either unsubstituted, or substituted with 1 to 5 substituents selected independently from the group consisting of lower alkyl, lower alkenyl, lower alkoxy, amino, halo, nitro, lower alkyl amino, or lower dialkylamino; or a phenyl ring attached to an alkyl chain of one to six carbon atoms, wherein the phenyl ring is either unsubstituted, or substituted with one to three substituents selected independently from the group consisting of lower alkyl, lower alkenyl, lower alkoxy, amino, halo, nitro, lower alkyl amino, or lower dialkylamino;

each R' is independently hydrogen or lower alkyl, or lower alkenyl or lower alkynyl where the unsaturated bond is at least one carbon removed from the O or N atom;

each R" is independently R, lower alkoxy, NHR' or AOR'; and

A is an amino acid residue, or a peptide of 2 to 3 amino acid residues.

40. A method for inhibiting serine proteases comprising the step of administering a therapeutically effective amount of a compound of the formula:

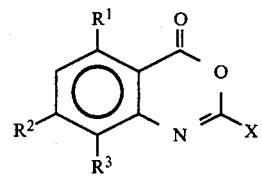

(I)

or a pharmaceutically acceptable ester or salt thereof, wherein:

$R^1$ is hydrogen or lower alkyl;

$R^2$ and $R^3$ are each independently hydrogen, halo, lower alkyl, hydroxy, lower alkoxy, lower thioalkyl, $-NO_2$, $-N(R')_2$, $-NR'COR'$, $-NHCON(R')_2$ or $-NHCOOR'$, with the proviso that at least one of $R^1$, $R^2$ and $R^3$ is not hydrogen when X is NHR or NR'COR"; and X is a radical chosen from the group consisting of:

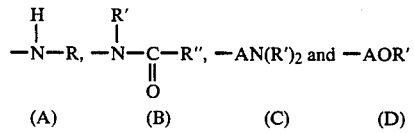

in which:

R is lower alkyl, lower alkenyl, lower alkynyl, a saturated hydrocarbon ring of 3 to 6 carbon atoms, either unsubstituted, or substituted with 1 to 5 substituents selected independently from the group consisting of lower alkyl, lower alkenyl, lower alkoxy, amino, halo, nitro, lower alkyl amino, or lower dialkylamino; or a phenyl ring attached to an alkyl chain of one to six carbon atoms, wherein the phenyl ring is either unsubstituted, or substituted with one to three substituents selected independently from the group consisting of lower alkyl, lower alkenyl, lower alkoxy, amino, halo, nitro, lower alkyl amino, or lower dialkylamino;

each R' is independently hydrogen or lower alkyl, or lower alkenyl or lower alkynyl where the unsaturated bond is at least one carbon removed from the O or N atom;

each R" is independently R, lower alkoxy, NHR' or AOR'; and

A is an amino acid residue, or a peptide of 2 to 3 amino acid residues.

* * * * *